United States Patent
Nelson et al.

(10) Patent No.: US 11,248,036 B2
(45) Date of Patent: **\*Feb. 15, 2022**

(54) MUTANT TUMOR NECROSIS FACTOR RECEPTOR SUPERFAMILY (TNFSFR) LIGANDS AND METHODS OF MAKING AND USING SAME

(71) Applicant: Washington University, St. Louis, MO (US)

(72) Inventors: Christopher Nelson, St. Louis, MO (US); Steven Teitelbaum, St. Louis, MO (US); Daved Fremont, St. Louis, MO (US); Julia T. Warren, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/717,373

(22) Filed: Dec. 17, 2019

(65) Prior Publication Data
US 2020/0199196 A1    Jun. 25, 2020

Related U.S. Application Data

(63) Continuation of application No. 15/894,502, filed on Feb. 12, 2018, now Pat. No. 10,550,169, which is a continuation of application No. 14/796,827, filed on Jul. 10, 2015, now Pat. No. 9,914,761.

(60) Provisional application No. 62/023,117, filed on Jul. 10, 2014.

(51) Int. Cl.
| C07K 14/705 | (2006.01) |
| C12N 15/12 | (2006.01) |
| C12N 15/63 | (2006.01) |
| A61K 38/00 | (2006.01) |

(52) U.S. Cl.
CPC ........ *C07K 14/70575* (2013.01); *A61K 38/00* (2013.01); *C07K 2319/00* (2013.01); *C07K 2319/02* (2013.01); *C07K 2319/21* (2013.01); *C07K 2319/23* (2013.01); *C07K 2319/30* (2013.01); *C07K 2319/50* (2013.01); *C07K 2319/74* (2013.01)

(58) Field of Classification Search
CPC ... C07K 14/70575; C12N 15/00; C12N 15/09
See application file for complete search history.

(56) References Cited

U.S. PATENT DOCUMENTS

| 6,740,739 B1 | 5/2004 | Ashkenazi et al. |
| 7,381,792 B2 | 6/2008 | Desjarlais et al. |
| 7,399,829 B2 | 7/2008 | Desjarlais et al. |
| 2003/0219864 A1 | 11/2003 | Desjarlais et al. |
| 2014/0178376 A1 | 6/2014 | Anderson et al. |
| 2015/0184244 A1 | 7/2015 | Li et al. |

FOREIGN PATENT DOCUMENTS

| WO | WO 2001/025277 | 4/2001 |
| WO | WO 2003/059281 | 7/2003 |

OTHER PUBLICATIONS

Meeting Program and Abstracts, ASCI/AAP Joint Meeting 2013, Apr. 26-28, 2013, 2 pages.
Ashkenazi, "Targeting Death and Decoy Receptors of the Tumour-Necrosis Factor Superfamily", Nature Reviews Cancer, Jun. 2002, pp. 420-430, vol. 2.
Blanco-Colio, "TWEAK/Fn14 Axis: A Promising Target for the Treatment of Cardiovascular Diseases", Jan. 20, 2014, pp. 1-13, vol. 5, Art. 3.
Bosman et al., "Decreased Affinity of Recombinant Human Tumor Necrosis Factor-Related Apoptosis-Inducing Ligand {rhTRAIL) D269H/E195R to Osteoprotegerin (OPG) Overcomes TRAIL Resistance Mediated by the Bone Microenvironment", The Journal of Biological Chemistry, Jan. 10, 2014, pp. 1071-1078, vol. 289, No. 2.
Bossen et al., "Interactions of Tumor Necrosis Factor (TNF) and TNF Receptor Family Members in the Mouse and Human", The Journal of Biochemistry, May 19, 2006, pp. 13964-13971, vol. 281, No. 20.
Boyce et al., "Biology of RANK, RANKL, and Osteoprotegerin", Arthritis Research & Therapy, Jun. 29, 2007, 7 pages, vol. 9, Suppl. 1.
Hauwermeiren et al., "Treatment of TNF Mediated Diseases by Selective Inhibition of Soluble TNF or TNFR1", Cytokine & Growth Factor Reviews, 2011, pp. 311-319, vol. 22.
Kripner-Heidenreich et al., "Single-Chain TNF, a TNF Derivative with Enhanced Stability and Antitumoral Activity", The Journal of Immunology, 2008, pp. 8176-8183, vol. 180.
Lam et al., "Crystal Structure of the TRANCE/RAN KL Cytokine Reveals Determinants of Receptor-Ligand Specificity", The Journal of Clinical Investigation, Oct. 2001, pp. 971-979, vol. 108, No. 7.
Liu et al., "Structural and Functional Insights of RAN KL-RANK Interaction and Signaling", The Journal of Immunology, May 14, 2010, pp. 1-10.

(Continued)

Primary Examiner — Prema M Mertz

(57) ABSTRACT

Methods for constructing efficient inhibitors of target TNF superfamily receptors, single chain target TNF superfamily ligands that inhibit of target TNF superfamily receptors while failing to engage or inhibit non-target TNF superfamily receptors, and methods of their use to treat diseases are provided. Single chain RANKL, TNF, and TRAIL ligands that effectively inhibit their target receptors while failing to inhibit non-target TNF superfamily receptors are also provided.

Figure 1A:
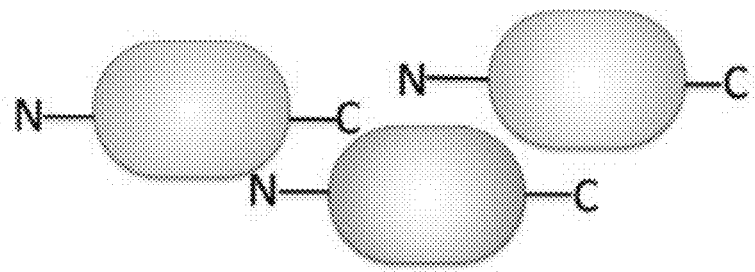
Figure 1A:
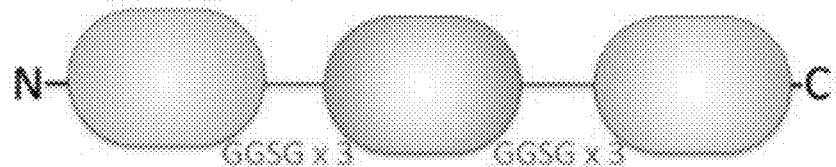

5 Claims, 43 Drawing Sheets
Specification includes a Sequence Listing.

(56) References Cited

OTHER PUBLICATIONS

Luan et al., "Crystal Structure of Human RANKL Complexed with Its Decoy Receptor Osteoprotegerin", The Journal of Immunology, 2012, pp. 245-252, vol. 189.
Merkel et al., "Tumor Necrosis Factor-a Mediates Orthopedic Implant Osteolysis", American Journal to Pathology, Jan. 1999, pp. 203-210, vol. 154, No. 1.
Nelson et al., "RAN KL Employs Distinct Binding Modes to Engage RANK and the OPG Decoy Receptor", National Institute of Health, Nov. 7, 2012, pp. 1971-1982, vol. 20, No. 11.
Schneider et al., "Potent Antitumoral Activity of TRAIL Through Generation of Tumor-Targeted Single-Chain Fusion Proteins", Cell Death and Disease, 2010, pp. 1-10, vol. 1, No. e68.
Spitzer et al., "A Genetically Encoded Multifunctional TRAIL Trimer Facilitates Cell-Specific Targeting and Tumor Cell Killing", Molecular Cancer Therapeutics, Jul. 2010, pp. 2142-2151, vol. 9, No. 7.
Warren et al., "Correlating RANK Ligand/RANK Binding Kinetics with Osteoclast Formation and Function", Journal of Cellular Biochemistry, 2015, pp. 2476-2483, vol. 116.
Warren et al., "Manipulation of RANK Monomer Assembly as a Novel Anti-Resorptive Strategy", ASBMR 2013 Annual Meeting, Aug. 2013, 3 pages.
Warren et al., "Manipulation of Receptor Oligomerization as a Strategy to Inhibit Signaling by TNF Superfamily Members", Pharmacology, Aug. 19, 2014, pp. 1-20, vol. 7, Issue 339.
Warren, "Single-Chain RAN KL Provides Insights into RANK Receptor Oligomerization and a Novel Approach to Osteoclast Inhibition", Washington University in St Louis Division of Biology and Biomedical Sciences Immunology, May 2015, pp. 1-111.
Warren, "Single-chain RANKL Provides Insights into RANK Receptor Oligomerization and a Novel Approach to Osteoclast; Inhibition", Arts and Sciences Electronic Thesis and Dissertations, May 15, 2015, Paper 466.

| Residue number | 194 | 236 | 269 | 270 | YSD Approximated $K_D$ (nM) | |
|---|---|---|---|---|---|---|
| | | | | | RANK | OPG |
| WT htRANKL | K | Q | F | H | ND * | 32.8 |
| K194E | E | | | | ND | 71.7 |
| Q236H | | H | | | 346.5 | ND |
| F269Y | | | Y | | ND | 33.3 |
| H270Y | | | | Y | 464.7 | 275.9 |
| K/Q | E | H | | | 69.7 | ND |
| K/Q/F | E | H | Y | | 23.6 | ND |
| K/Q/F/H | E | H | Y | Y | 1.4 | ND |

FIGURE 3B

| | | $K_D$ (RANK-Fc)* | $K_D$ (OPG-Fc)* |
|---|---|---|---|
| WT | | 5.24E-10 | 1.96E-11 |
| Mut1 | R190G | 6.79E-09 | 4.53E-10 |
| Mut2 | G191D | 7.31E-09 | 7.05E-10 |
| Mut3 | AA'-1 WYHDggsRGW | 1.32E-08 | 8.77E-10 |
| Mut4 | AA'-2 WYHDssRGW | 1.05E-08 | 3.89E-10 |
| Mut5 | AA'-3 WYHDsRGW | 1.22E-08 | 1.48E-10 |
| Mut6 | AA'-4 WYHDsRsGW | 2.17E-08 | 9.40E-10 |
| Mut7 | AA'-5 WYssHDRGW | 1.36E-08 | 3.84E-10 |
| Mut8 | AA'-6 WYsHDRGW | 1.43E-08 | 1.85E-11 |
| Mut9 | R222A | 1.35E-08 | 1.09E-09 |
| Mut10 | R222Y | 2.34E-09 | 5.30E-10 |
| Mut11 | E268Y | 1.12E-08 | 1.61E-10 |
| Mut12 | E268Yggs | 9.16E-09 | 2.40E-12 |
| Mut13 | R222Y/E268Y | 6.59E-09 | 1.48E-09 |
| Mut14 | H224E | 2.07E-08 | 4.73E-11 |
| Mut15 | E225R | 1.53E-06 | 9.35E-12 |
| Mut16 | CD-1 FRggsHHET | Not Detectable | 6.10E-11 |
| Mut17 | CD-2 FRhggsHHET | Not Detectable | 3.56E-12 |
| Mut21 | E225R/E268Y | 1.14E-08 | 1.02E-11 |
| Mut22 | AA'-1/CD-1 | Not Detectable | 1.07E-09 |
| Mut23 | AA'-1/CD-2 | Not Detectable | 2.20E-09 |
| Mut24 | AA'-2/CD-1 | Not Detectable | 9.78E-10 |
| Mut25 | AA'2/CD-2 | Not Detectable | 1.39E-09 |
| Mut28 | R222A/E268A | 1.85E-08 | 1.48E-09 |

CDins RANKL: ggs inserted after R222 (Mut16)

FIGURE 7A

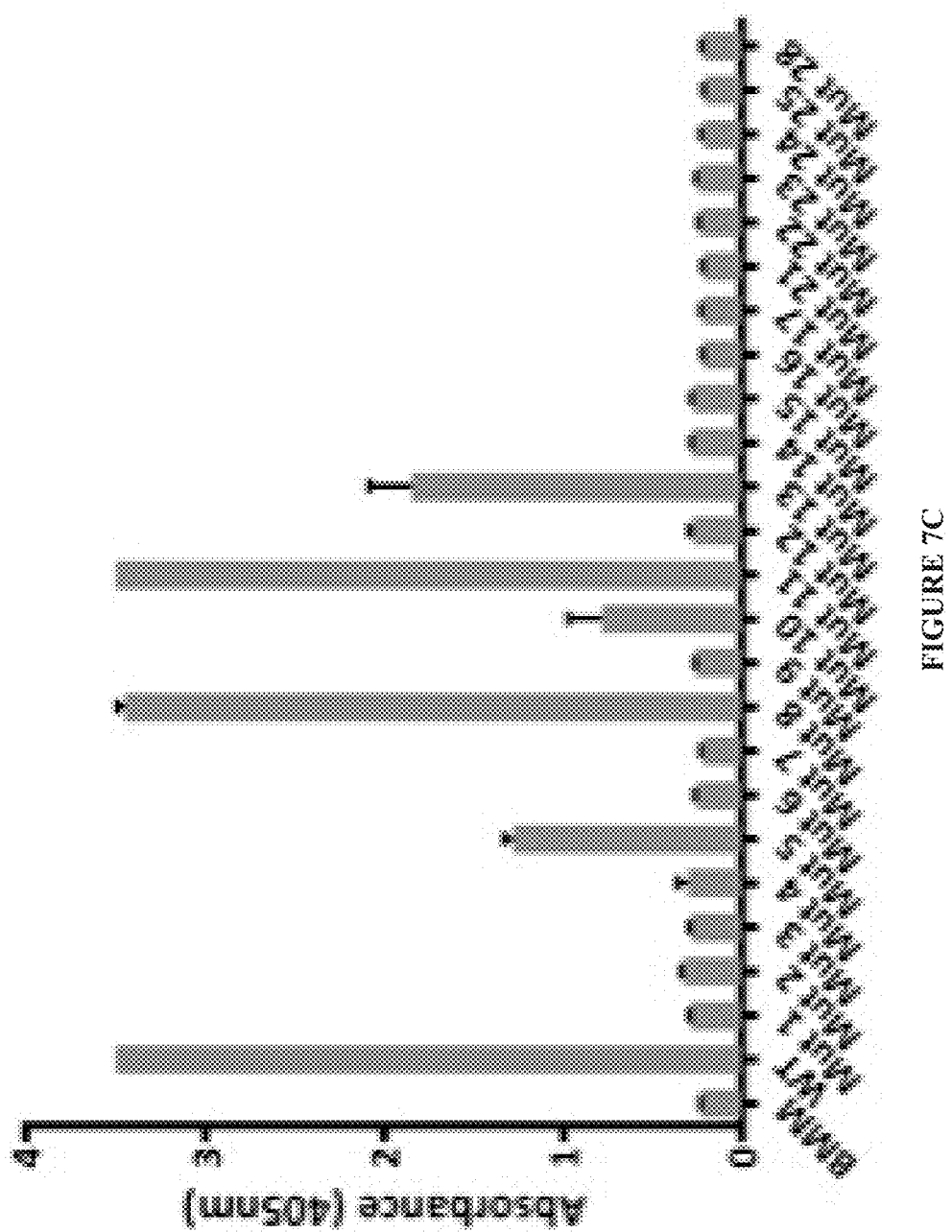

*CDins/WT or CDins/Q = Block;   KFH/Q = High affinity

SEQUENCE LISTING

<160> NUMBER OF SEQ ID NOS: 44

<210> SEQ ID NO 1
<211> LENGTH: 316
<212> TYPE: PRT
<213> ORGANISM: Mus musculus

<400> SEQUENCE: 1

Met Arg Arg Ala Ser Arg Asp Tyr Gly Lys Tyr Leu Arg Ser Ser Glu
1               5                   10                  15

Glu Met Gly Ser Gly Pro Gly Val Pro His Glu Gly Pro Leu His Pro
            20                  25                  30

Ala Pro Ser Ala Pro Ala Pro Pro Pro Ala Ala Ser Arg Ser
        35                  40                  45

Met Phe Leu Ala Leu Leu Gly Leu Gly Leu Gly Gln Val Val Cys Ser
    50                  55                  60

Ile Ala Leu Phe Leu Tyr Phe Arg Ala Gln Met Asp Pro Asn Arg Ile
65                  70                  75                  80

Ser Glu Asp Ser Thr His Cys Phe Tyr Arg Ile Leu Arg Leu His Glu
                85                  90                  95

Asn Ala Asp Leu Gln Asp Ser Thr Leu Glu Ser Glu Asp Thr Leu Pro
            100                 105                 110

Asp Ser Cys Arg Arg Met Lys Gln Ala Phe Gln Gly Ala Val Gln Lys
        115                 120                 125

Glu Leu Gln His Ile Val Gly Pro Gln Arg Phe Ser Gly Ala Pro Ala
130                 135                 140

Met Met Glu Gly Ser Trp Leu Asp Val Ala Gln Arg Gly Lys Pro Glu
145                 150                 155                 160

Ala Gln Pro Phe Ala His Leu Thr Ile Asn Ala Ala Ser Ile Pro Ser
                165                 170                 175

Gly Ser His Lys Val Thr Leu Ser Ser Trp Tyr His Asp Arg Gly Trp
            180                 185                 190

Ala Lys Ile Ser Asn Met Thr Leu Ser Asn Gly Lys Leu Arg Val Asn
        195                 200                 205

Gln Asp Gly Phe Tyr Tyr Leu Tyr Ala Asn Ile Cys Phe Arg His His
    210                 215                 220

Glu Thr Ser Gly Ser Val Pro Thr Asp Tyr Leu Gln Leu Met Val Tyr
225                 230                 235                 240

Val Val Lys Thr Ser Ile Lys Ile Pro Ser Ser His Asn Leu Met Lys
                245                 250                 255

Gly Gly Ser Thr Lys Asn Trp Ser Gly Asn Ser Glu Phe His Phe Tyr
            260                 265                 270

Ser Ile Asn Val Gly Gly Phe Phe Lys Leu Arg Ala Gly Glu Glu Ile
        275                 280                 285

Ser Ile Gln Val Ser Asn Pro Ser Leu Leu Asp Pro Asp Gln Asp Ala
    290                 295                 300

Thr Tyr Phe Gly Ala Phe Lys Val Gln Asp Ile Asp
305                 310                 315

<210> SEQ ID NO 2
<211> LENGTH: 317
<212> TYPE: PRT
<213> ORGANISM: Homo sapiens

<400> SEQUENCE: 2

Met Arg Arg Ala Ser Arg Asp Tyr Thr Lys Tyr Leu Arg Gly Ser Glu

```
1               5                    10                   15
Glu Met Gly Gly Gly Pro Gly Ala Pro His Glu Gly Pro Leu His Ala
             20                   25                   30

Pro Pro Pro Ala Pro His Gln Pro Ala Ala Ser Arg Ser Met
         35                   40                   45

Phe Val Ala Leu Leu Gly Leu Gly Leu Gly Gln Val Val Cys Ser Val
         50                   55                   60

Ala Leu Phe Phe Tyr Phe Arg Ala Gln Met Asp Pro Asn Arg Ile Ser
65                   70                   75                   80

Glu Asp Gly Thr His Cys Ile Tyr Arg Ile Leu Arg Leu His Glu Asn
                 85                   90                   95

Ala Asp Phe Gln Asp Thr Thr Leu Glu Ser Gln Asp Thr Lys Leu Ile
                 100                  105                  110

Pro Asp Ser Cys Arg Arg Ile Lys Gln Ala Phe Gln Gly Ala Val Gln
                 115                  120                  125

Lys Glu Leu Gln His Ile Val Gly Ser Gln His Ile Arg Ala Glu Lys
         130                  135                  140

Ala Met Val Asp Gly Ser Trp Leu Asp Leu Ala Lys Arg Ser Lys Leu
145                  150                  155                  160

Glu Ala Gln Pro Phe Ala His Leu Thr Ile Asn Ala Thr Asp Ile Pro
                 165                  170                  175

Ser Gly Ser His Lys Val Ser Leu Ser Ser Trp Tyr His Asp Arg Gly
                 180                  185                  190

Trp Ala Lys Ile Ser Asn Met Thr Phe Ser Asn Gly Lys Leu Ile Val
         195                  200                  205

Asn Gln Asp Gly Phe Tyr Tyr Leu Tyr Ala Asn Ile Cys Phe Arg His
         210                  215                  220

His Glu Thr Ser Gly Asp Leu Ala Thr Glu Tyr Leu Gln Leu Met Val
225                  230                  235                  240

Tyr Val Thr Lys Thr Ser Ile Lys Ile Pro Ser Ser His Thr Leu Met
                 245                  250                  255

Lys Gly Gly Ser Thr Lys Tyr Trp Ser Gly Asn Ser Glu Phe His Phe
                 260                  265                  270

Tyr Ser Ile Asn Val Gly Gly Phe Lys Leu Arg Ser Gly Glu Glu
                 275                  280                  285

Ile Ser Ile Glu Val Ser Asn Pro Ser Leu Leu Asp Pro Asp Gln Asp
                 290                  295                  300

Ala Thr Tyr Phe Gly Ala Phe Lys Val Arg Asp Ile Asp
305                  310                  315

<210> SEQ ID NO 3
<211> LENGTH: 235
<212> TYPE: PRT
<213> ORGANISM: Mus musculus

<400> SEQUENCE: 3

Met Ser Thr Glu Ser Met Ile Arg Asp Val Glu Leu Ala Glu Glu Ala
1               5                    10                   15

Leu Pro Gln Lys Met Gly Gly Phe Gln Asn Ser Arg Arg Cys Leu Cys
             20                   25                   30

Leu Ser Leu Phe Ser Phe Leu Leu Val Ala Gly Ala Thr Thr Leu Phe
             35                   40                   45

Cys Leu Leu Asn Phe Gly Val Ile Gly Pro Gln Arg Asp Glu Lys Phe
         50                   55                   60
```

```
Pro Asn Gly Leu Pro Leu Ile Ser Ser Met Ala Gln Thr Leu Thr Leu
 65                  70                  75                  80

Arg Ser Ser Ser Gln Asn Ser Ser Asp Lys Pro Val Ala His Val Val
                 85                  90                  95

Ala Asn His Gln Val Glu Glu Gln Leu Glu Trp Leu Ser Gln Arg Ala
            100                 105                 110

Asn Ala Leu Leu Ala Asn Gly Met Asp Leu Lys Asp Asn Gln Leu Val
        115                 120                 125

Val Pro Ala Asp Gly Leu Tyr Leu Val Tyr Ser Gln Val Leu Phe Lys
130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Asn Leu Leu Ser Ala Val Lys
                165                 170                 175

Ser Pro Cys Pro Lys Asp Thr Pro Glu Gly Ala Glu Leu Lys Pro Trp
            180                 185                 190

Tyr Glu Pro Ile Tyr Leu Gly Gly Val Phe Gln Leu Glu Lys Gly Asp
        195                 200                 205

Gln Leu Ser Ala Glu Val Asn Leu Pro Lys Tyr Leu Asp Phe Ala Glu
210                 215                 220

Ser Gly Gln Val Tyr Phe Gly Val Ile Ala Leu
225                 230                 235

<210> SEQ ID NO 4
<211> LENGTH: 233
<212> TYPE: PRT
<213> ORGANISM: Homo sapiens

<400> SEQUENCE: 4

Met Ser Thr Glu Ser Met Ile Arg Asp Val Glu Leu Ala Glu Glu Ala
  1               5                  10                  15

Leu Pro Lys Lys Thr Gly Gly Pro Gln Gly Ser Arg Arg Cys Leu Phe
                 20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
 50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
                 85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205
```

```
Ser Ala Glu Ile Asn Arg Pro Asp Tyr Leu Asp Phe Ala Glu Ser Gly
    210                 215                 220
Gln Val Tyr Phe Gly Ile Ile Ala Leu
225                 230

<210> SEQ ID NO 5
<211> LENGTH: 291
<212> TYPE: PRT
<213> ORGANISM: Mus musculus

<400> SEQUENCE: 5

Met Pro Ser Ser Gly Ala Leu Lys Asp Leu Ser Phe Ser Gln His Phe
1               5                   10                  15

Arg Met Met Val Ile Cys Ile Val Leu Leu Gln Val Leu Leu Gln Ala
                20                  25                  30

Val Ser Val Ala Val Thr Tyr Met Tyr Phe Thr Asn Glu Met Lys Gln
            35                  40                  45

Leu Gln Asp Asn Tyr Ser Lys Ile Gly Leu Ala Cys Phe Ser Lys Thr
    50                  55                  60

Asp Glu Asp Phe Trp Asp Ser Thr Asp Gly Glu Ile Leu Asn Arg Pro
65                  70                  75                  80

Cys Leu Gln Val Lys Arg Gln Leu Tyr Gln Leu Ile Glu Glu Val Thr
                85                  90                  95

Leu Arg Thr Phe Gln Asp Thr Ile Ser Thr Val Pro Glu Lys Gln Leu
                100                 105                 110

Ser Thr Pro Pro Leu Pro Arg Gly Gly Arg Pro Gln Lys Val Ala Ala
            115                 120                 125

His Ile Thr Gly Ile Thr Arg Arg Ser Asn Ser Ala Leu Ile Pro Ile
    130                 135                 140

Ser Lys Asp Gly Lys Thr Leu Gly Gln Lys Ile Glu Ser Trp Glu Ser
145                 150                 155                 160

Ser Arg Lys Gly His Ser Phe Leu Asn His Val Leu Phe Arg Asn Gly
                165                 170                 175

Glu Leu Val Ile Glu Gln Glu Gly Leu Tyr Tyr Ile Tyr Ser Gln Thr
                180                 185                 190

Tyr Phe Arg Phe Gln Glu Ala Glu Asp Ala Ser Lys Met Val Ser Lys
            195                 200                 205

Asp Lys Val Arg Thr Lys Gln Leu Val Gln Tyr Ile Tyr Lys Tyr Thr
    210                 215                 220

Ser Tyr Pro Asp Pro Ile Val Leu Met Lys Ser Ala Arg Asn Ser Cys
225                 230                 235                 240

Trp Ser Arg Asp Ala Glu Tyr Gly Leu Tyr Ser Ile Tyr Gln Gly Gly
                245                 250                 255

Leu Phe Glu Leu Lys Lys Asn Asp Arg Ile Phe Val Ser Val Thr Asn
                260                 265                 270

Glu His Leu Met Asp Leu Asp Gln Glu Ala Ser Phe Phe Gly Ala Phe
            275                 280                 285

Leu Ile Asn
    290

<210> SEQ ID NO 6
<211> LENGTH: 281
<212> TYPE: PRT
<213> ORGANISM: Homo sapiens

<400> SEQUENCE: 6
```

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
                100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
                180                 185                 190

Gln Glu Glu Ile Lys Glu Asn Thr Lys Asn Asp Lys Gln Met Val Gln
                195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
                260                 265                 270

Ser Phe Phe Gly Ala Phe Leu Val Gly
                275                 280

<210> SEQ ID NO 7
<211> LENGTH: 499
<212> TYPE: PRT
<213> ORGANISM: Artificial
<220> FEATURE:
<223> OTHER INFORMATION: synthetic

<400> SEQUENCE: 7

Gln Pro Phe Ala His Leu Thr Ile Asn Ala Ala Ser Ile Pro Ser Gly
1               5                   10                  15

Ser His Lys Val Thr Leu Ser Ser Trp Tyr His Asp Arg Gly Trp Ala
            20                  25                  30

Lys Ile Ser Asn Met Thr Leu Ser Asn Gly Lys Leu Arg Val Asn Gln
            35                  40                  45

Asp Gly Phe Tyr Tyr Leu Tyr Ala Asn Ile Ser Phe Arg His His Glu
    50                  55                  60

Thr Ser Gly Ser Val Pro Thr Asp Tyr Leu Gln Leu Met Val Tyr Val
65                  70                  75                  80

```
Val Lys Thr Ser Glu Lys Ile Pro Ser Ser His Asn Leu Met Lys Gly
                85                  90                  95

Gly Ser Thr Lys Asn Trp Ser Gly Asn Ser Glu Phe His Phe Tyr Ser
               100                 105                 110

Ile Asn Val Gly Gly Phe Phe Lys Leu Arg Ala Gly Glu Glu Ile Ser
               115                 120                 125

Ile Gln Val Ser Asn Pro Ser Leu Leu Asp Pro Asp Gln Asp Ala Thr
130                 135                 140

Tyr Phe Gly Ala Phe Lys Val Gln Asp Ile Asp Gly Ser Gly Gly
145                 150                 155                 160

Gly Ser Gly Gly Gly Ser Gly Gln Pro Phe Ala His Leu Thr Ile Asn
               165                 170                 175

Ala Ala Ser Ile Pro Ser Gly Ser His Lys Val Thr Leu Ser Ser Trp
               180                 185                 190

Tyr His Asp Arg Gly Trp Ala Lys Ile Ser Asn Met Thr Leu Ser Asn
               195                 200                 205

Gly Lys Leu Arg Val Asn Gln Asp Gly Phe Tyr Tyr Leu Tyr Ala Asn
               210                 215                 220

Ile Ser Phe Arg His His Glu Thr Ser Gly Ser Val Pro Thr Asp Tyr
225                 230                 235                 240

Leu Gln Leu Met Val Tyr Val Val Lys Thr Ser Glu Lys Ile Pro Ser
               245                 250                 255

Ser His Asn Leu Met Lys Gly Gly Ser Thr Lys Asn Trp Ser Gly Asn
               260                 265                 270

Ser Glu Phe His Phe Tyr Ser Ile Asn Val Gly Gly Phe Phe Lys Leu
               275                 280                 285

Arg Ala Gly Glu Glu Ile Ser Ile Gln Val Ser Asn Pro Ser Leu Leu
               290                 295                 300

Asp Pro Asp Gln Asp Ala Thr Tyr Phe Gly Ala Phe Lys Val Gln Asp
305                 310                 315                 320

Ile Asp Gly Gly Ser Gly Gly Gly Ser Gly Gly Gly Ser Gly Gln Pro
               325                 330                 335

Phe Ala His Leu Thr Ile Asn Ala Ala Ser Ile Pro Ser Gly Ser His
               340                 345                 350

Lys Val Thr Leu Ser Ser Trp Tyr His Asp Arg Gly Trp Ala Lys Ile
               355                 360                 365

Ser Asn Met Thr Leu Ser Asn Gly Lys Leu Arg Val Asn Gln Asp Gly
               370                 375                 380

Phe Tyr Tyr Leu Tyr Ala Asn Ile Ser Phe Arg His His Glu Thr Ser
385                 390                 395                 400

Gly Ser Val Pro Thr Asp Tyr Leu Gln Leu Met Val Tyr Val Val Lys
               405                 410                 415

Thr Ser Glu Lys Ile Pro Ser Ser His Asn Leu Met Lys Gly Gly Ser
               420                 425                 430

Thr Lys Asn Trp Ser Gly Asn Ser Glu Phe His Phe Tyr Ser Ile Asn
               435                 440                 445

Val Gly Gly Phe Phe Lys Leu Arg Ala Gly Glu Glu Ile Ser Ile Gln
               450                 455                 460

Val Ser Asn Pro Ser Leu Leu Asp Pro Asp Gln Asp Ala Thr Tyr Phe
465                 470                 475                 480

Gly Ala Phe Lys Val Gln Asp Ile Asp Ser Ser Gly Arg Glu Asn Leu
               485                 490                 495
```

Tyr Phe Gln

<210> SEQ ID NO 8
<211> LENGTH: 499
<212> TYPE: PRT
<213> ORGANISM: Artificial
<220> FEATURE:
<223> OTHER INFORMATION: synthetic

<400> SEQUENCE: 8

Gln Pro Phe Ala His Leu Thr Ile Asn Ala Ala Ser Ile Pro Ser Gly
1               5                   10                  15

Ser His Lys Val Thr Leu Ser Ser Trp Tyr His Asp Arg Gly Trp Ala
            20                  25                  30

Lys Ile Ser Asn Met Thr Leu Ser Asn Gly Lys Leu Arg Val Asn Gln
        35                  40                  45

Asp Gly Phe Tyr Tyr Leu Tyr Ala Asn Ile Ser Phe Arg His Asn Glu
    50                  55                  60

Thr Ser Gly Ser Val Pro Thr Asp Tyr Leu Gln Leu Met Val Tyr Val
65                  70                  75                  80

Val Lys Thr Ser Glu Lys Ile Pro Ser Ser His Asn Leu Met Lys Gly
                85                  90                  95

Gly Ser Thr Lys Asn Trp Ser Gly Asn Ser Glu Phe His Phe Tyr Ser
            100                 105                 110

Ile Asn Val Gly Gly Phe Phe Lys Leu Arg Ala Gly Glu Glu Ile Ser
        115                 120                 125

Ile Gln Val Ser Asn Pro Ser Leu Leu Asp Pro Asp Gln Asp Ala Thr
    130                 135                 140

Tyr Phe Gly Ala Phe Lys Val Gln Asp Ile Asp Gly Gly Ser Gly Gly
145                 150                 155                 160

Gly Ser Gly Gly Gly Ser Gly Gln Pro Phe Ala His Leu Thr Ile Asn
            165                 170                 175

Arg Ala Ser Ile Pro Ser Gly Ser His Lys Val Thr Leu Ser Ser Trp
            180                 185                 190

Tyr His Asp Arg Ala Trp Ala Lys Ile Ser Asn Met Thr Leu Ser Asn
            195                 200                 205

Gly Lys Leu Arg Val Asn Gln Asp Gly Phe Tyr Tyr Leu Tyr Ala Asn
        210                 215                 220

Ile Ser Phe Arg His His Glu Thr Ser Gly Ser Val Pro Thr Asp Tyr
225                 230                 235                 240

Leu Gln Leu Met Val Tyr Val Val Lys Thr Ser Glu Lys Ile Pro Ser
                245                 250                 255

Ser His Asn Leu Met Lys Gly Gly Ser Thr Lys Asn Trp Ser Gly Asn
            260                 265                 270

Ser Glu Phe His Phe Tyr Ser Ile Asn Val Gly Gly Phe Phe Lys Leu
        275                 280                 285

Arg Ala Gly Glu Glu Ile Ser Ile Gln Val Ser Asn Pro Ser Leu Leu
    290                 295                 300

Asp Pro Asp Gln Asp Ala Thr Tyr Phe Gly Ala Phe Lys Val Gln Asp
305                 310                 315                 320

Ile Asp Gly Gly Ser Gly Gly Gly Ser Gly Gly Gly Ser Gly Gln Pro
                325                 330                 335

Phe Ala His Leu Thr Ile Asn Arg Ala Ser Ile Pro Ser Gly Ser His
            340                 345                 350

Lys Val Thr Leu Ser Ser Trp Tyr His Asp Arg Ala Trp Ala Lys Ile

| | | 355 | | | | 360 | | | | 365 | | |
|---|---|---|---|---|---|---|---|---|---|---|---|---|

Ser Asn Met Thr Leu Ser Asn Gly Lys Leu Arg Val Asn Gln Asp Gly
370 375 380

Phe Tyr Tyr Leu Tyr Ala Asn Ile Ser Phe Arg His His Glu Thr Ser
385 390 395 400

Gly Ser Val Pro Thr Asp Tyr Leu Gln Leu Met Val Tyr Val Lys
405 410 415

Thr Ser Glu Lys Arg Pro Ser Ser His Asn Leu Met Lys Gly Gly Ser
420 425 430

Thr Lys Asn Trp Ser Gly Asn Ser Glu Phe His Phe Tyr Ser Ile Asn
435 440 445

Val Gly Gly Phe Phe Lys Leu Arg Ala Gly Glu Glu Ile Ser Ile Gln
450 455 460

Val Ser Asn Pro Ser Leu Leu Asp Pro Asp Gln Asp Ala Thr Tyr Phe
465 470 475 480

Gly Ala Phe Lys Val Gln Asp Ile Asp Ser Ser Gly Arg Glu Asn Leu
485 490 495

Tyr Phe Gln

<210> SEQ ID NO 9
<211> LENGTH: 332
<212> TYPE: PRT
<213> ORGANISM: Artificial
<220> FEATURE:
<223> OTHER INFORMATION: synthetic

<400> SEQUENCE: 9

Gln Pro Phe Ala His Leu Thr Ile Asn Arg Ala Ser Ile Pro Ser Gly
1 5 10 15

Ser His Lys Val Thr Leu Ser Ser Trp Tyr His Asp Arg Ala Trp Ala
20 25 30

Lys Ile Ser Asn Met Thr Leu Ser Asn Gly Lys Leu Arg Val Asn Gln
35 40 45

Asp Gly Phe Tyr Tyr Leu Tyr Ala Asn Ile Ser Phe Arg His His Glu
50 55 60

Thr Ser Gly Ser Val Pro Thr Asp Tyr Leu Gln Leu Met Val Tyr Val
65 70 75 80

Val Lys Thr Ser Glu Lys Ile Arg Ser Ser His Asn Leu Met Lys Gly
85 90 95

Gly Ser Thr Lys Asn Trp Ser Gly Asn Ser Glu Phe His Phe Tyr Ser
100 105 110

Ile Asn Val Gly Gly Phe Phe Lys Leu Arg Ala Gly Glu Glu Ile Ser
115 120 125

Ile Gln Val Ser Asn Pro Ser Leu Leu Asp Pro Asp Gln Asp Ala Thr
130 135 140

Tyr Phe Gly Ala Phe Lys Val Gln Asp Ile Asp Gly Ser Gly Gly
145 150 155 160

Gly Ser Gly Gly Gly Ser Gly Gln Pro Phe Ala His Leu Thr Ile Asn
165 170 175

Ala Ala Ser Ile Pro Ser Gly Ser His Lys Val Thr Leu Ser Ser Trp
180 185 190

Tyr His Asp Arg Gly Trp Ala Lys Ile Ser Asn Met Thr Leu Ser Asn
195 200 205

Gly Lys Leu Arg Val Asn Gln Asp Gly Phe Tyr Tyr Leu Tyr Ala Asn
210 215 220

```
Ile Ser Phe Arg His Asn Glu Thr Ser Gly Ser Val Pro Thr Asp Tyr
225                 230                 235                 240

Leu Gln Leu Met Val Tyr Val Val Lys Thr Ser Glu Lys Arg Pro Ser
                245                 250                 255

Ser His Asn Leu Met Lys Gly Gly Ser Thr Lys Asn Trp Ser Gly Asn
            260                 265                 270

Ser Glu Phe His Phe Tyr Ser Ile Asn Val Gly Gly Phe Phe Lys Leu
        275                 280                 285

Arg Ala Gly Glu Glu Ile Ser Ile Gln Val Ser Asn Pro Ser Leu Leu
    290                 295                 300

Asp Pro Asp Gln Asp Ala Thr Tyr Phe Gly Ala Phe Lys Val Gln Asp
305                 310                 315                 320

Ile Asp Ser Ser Gly Arg Glu Asn Leu Tyr Phe Gln
                325                 330

<210> SEQ ID NO 10
<211> LENGTH: 502
<212> TYPE: PRT
<213> ORGANISM: Artificial
<220> FEATURE:
<223> OTHER INFORMATION: synthetic

<400> SEQUENCE: 10

Gln Pro Phe Ala His Leu Thr Ile Asn Ala Ala Ser Ile Pro Ser Gly
1               5                   10                  15

Ser His Lys Val Thr Leu Ser Ser Trp Tyr His Asp Arg Gly Trp Ala
            20                  25                  30

Lys Ile Ser Asn Met Thr Leu Ser Asn Gly Lys Leu Arg Val Asn Gln
        35                  40                  45

Asp Gly Phe Tyr Tyr Leu Tyr Ala Asn Ile Ser Phe Arg Gly Gly Ser
    50                  55                  60

His His Glu Thr Ser Gly Ser Val Pro Thr Asp Tyr Leu His Leu Met
65                  70                  75                  80

Val Tyr Val Val Lys Thr Ser Glu Lys Ile Pro Ser Ser His Asn Leu
                85                  90                  95

Met Lys Gly Gly Ser Thr Lys Asn Trp Ser Gly Asn Ser Glu Phe His
            100                 105                 110

Phe Tyr Ser Ile Asn Val Gly Gly Phe Phe Lys Leu Arg Ala Gly Glu
        115                 120                 125

Glu Ile Ser Ile Gln Val Ser Asn Pro Ser Leu Leu Asp Pro Asp Gln
    130                 135                 140

Asp Ala Thr Tyr Phe Gly Ala Phe Lys Val Gln Asp Ile Asp Gly Gly
145                 150                 155                 160

Ser Gly Gly Gly Ser Gly Gly Ser Gly Gln Pro Phe Ala His Leu
                165                 170                 175

Thr Ile Asn Ala Ala Ser Ile Pro Ser Gly Ser His Lys Val Thr Leu
            180                 185                 190

Ser Ser Trp Tyr His Asp Arg Gly Trp Ala Glu Ile Ser Asn Met Thr
        195                 200                 205

Leu Ser Asn Gly Lys Leu Arg Val Asn Gln Asp Gly Phe Tyr Tyr Leu
    210                 215                 220

Tyr Ala Asn Ile Ser Phe Arg His His Glu Thr Ser Gly Ser Val Pro
225                 230                 235                 240

Thr Asp Tyr Leu His Leu Met Val Tyr Val Val Lys Thr Ser Glu Lys
                245                 250                 255
```

Ile Pro Ser Ser His Asn Leu Met Lys Gly Gly Ser Thr Lys Asn Trp
            260                 265                 270

Ser Gly Asn Ser Glu Tyr Tyr Phe Tyr Ser Ile Asn Val Gly Gly Phe
            275                 280                 285

Phe Lys Leu Arg Ala Gly Glu Glu Ile Ser Ile Gln Val Ser Asn Pro
            290                 295                 300

Ser Leu Leu Asp Pro Asp Gln Asp Ala Thr Tyr Phe Gly Ala Phe Lys
305                 310                 315                 320

Val Gln Asp Ile Asp Gly Gly Ser Gly Gly Ser Gly Gly Gly Gly Ser
            325                 330                 335

Gly Gln Pro Phe Ala His Leu Thr Ile Asn Ala Ala Ser Ile Pro Ser
            340                 345                 350

Gly Ser His Lys Val Thr Leu Ser Ser Trp Tyr His Asp Arg Gly Trp
            355                 360                 365

Ala Glu Ile Ser Asn Met Thr Leu Ser Asn Gly Lys Leu Arg Val Asn
            370                 375                 380

Gln Asp Gly Phe Tyr Tyr Leu Tyr Ala Asn Ile Ser Phe Arg His His
385                 390                 395                 400

Glu Thr Ser Gly Ser Val Pro Thr Asp Tyr Leu His Leu Met Val Tyr
            405                 410                 415

Val Val Lys Thr Ser Glu Lys Ile Pro Ser Ser His Asn Leu Met Lys
            420                 425                 430

Gly Gly Ser Thr Lys Asn Trp Ser Gly Asn Ser Glu Tyr Tyr Phe Tyr
            435                 440                 445

Ser Ile Asn Val Gly Gly Phe Phe Lys Leu Arg Ala Gly Glu Glu Ile
            450                 455                 460

Ser Ile Gln Val Ser Asn Pro Ser Leu Leu Asp Pro Asp Gln Asp Ala
465                 470                 475                 480

Thr Tyr Phe Gly Ala Phe Lys Val Gln Asp Ile Asp Ser Ser Gly Arg
            485                 490                 495

Glu Asn Leu Tyr Phe Gln
            500

<210> SEQ ID NO 11
<211> LENGTH: 505
<212> TYPE: PRT
<213> ORGANISM: Artificial
<220> FEATURE:
<223> OTHER INFORMATION: synthetic

<400> SEQUENCE: 11

Gln Pro Phe Ala His Leu Thr Ile Asn Ala Ala Ser Ile Pro Ser Gly
1               5                   10                  15

Ser His Lys Val Thr Leu Ser Ser Trp Tyr His Asp Arg Gly Trp Ala
            20                  25                  30

Lys Ile Ser Asn Met Thr Leu Ser Asn Gly Lys Leu Arg Val Asn Gln
            35                  40                  45

Asp Gly Phe Tyr Tyr Leu Tyr Ala Asn Ile Ser Phe Arg Gly Gly Ser
            50                  55                  60

His His Glu Thr Ser Gly Ser Val Pro Thr Asp Tyr Leu His Leu Met
65                  70                  75                  80

Val Tyr Val Val Lys Thr Ser Glu Lys Ile Pro Ser Ser His Asn Leu
            85                  90                  95

Met Lys Gly Gly Ser Thr Lys Asn Trp Ser Gly Asn Ser Glu Phe His
            100                 105                 110

Phe Tyr Ser Ile Asn Val Gly Gly Phe Phe Lys Leu Arg Ala Gly Glu
            115                 120                 125

Glu Ile Ser Ile Gln Val Ser Asn Pro Ser Leu Leu Asp Pro Asp Gln
        130                 135                 140

Asp Ala Thr Tyr Phe Gly Ala Phe Lys Val Gln Asp Ile Asp Gly Gly
145                 150                 155                 160

Ser Gly Gly Gly Ser Gly Gly Ser Gly Gln Pro Phe Ala His Leu
                165                 170                 175

Thr Ile Asn Ala Ala Ser Ile Pro Ser Gly Ser His Lys Val Thr Leu
                180                 185                 190

Ser Ser Trp Tyr His Asp Arg Gly Trp Ala Lys Ile Ser Asn Met Thr
        195                 200                 205

Leu Ser Asn Gly Lys Leu Arg Val Asn Gln Asp Gly Phe Tyr Tyr Leu
        210                 215                 220

Tyr Ala Asn Ile Ser Phe Arg Gly Gly Ser His His Glu Thr Ser Gly
225                 230                 235                 240

Ser Val Pro Thr Asp Tyr Leu His Leu Met Val Tyr Val Lys Thr
                245                 250                 255

Ser Glu Lys Ile Pro Ser Ser His Asn Leu Met Lys Gly Gly Ser Thr
        260                 265                 270

Lys Asn Trp Ser Gly Asn Ser Glu Phe His Phe Tyr Ser Ile Asn Val
        275                 280                 285

Gly Gly Phe Phe Lys Leu Arg Ala Gly Glu Glu Ile Ser Ile Gln Val
        290                 295                 300

Ser Asn Pro Ser Leu Leu Asp Pro Asp Gln Asp Ala Thr Tyr Phe Gly
305                 310                 315                 320

Ala Phe Lys Val Gln Asp Ile Asp Gly Gly Ser Gly Gly Gly Ser Gly
                325                 330                 335

Gly Gly Ser Gly Gln Pro Phe Ala His Leu Thr Ile Asn Ala Ala Ser
        340                 345                 350

Ile Pro Ser Gly Ser His Lys Val Thr Leu Ser Ser Trp Tyr His Asp
        355                 360                 365

Arg Gly Trp Ala Glu Ile Ser Asn Met Thr Leu Ser Asn Gly Lys Leu
        370                 375                 380

Arg Val Asn Gln Asp Gly Phe Tyr Tyr Leu Tyr Ala Asn Ile Ser Phe
385                 390                 395                 400

Arg His His Glu Thr Ser Gly Ser Val Pro Thr Asp Tyr Leu His Leu
                405                 410                 415

Met Val Tyr Val Val Lys Thr Ser Glu Lys Ile Pro Ser Ser His Asn
                420                 425                 430

Leu Met Lys Gly Gly Ser Thr Lys Asn Trp Ser Gly Asn Ser Glu Tyr
        435                 440                 445

Tyr Phe Tyr Ser Ile Asn Val Gly Gly Phe Phe Lys Leu Arg Ala Gly
        450                 455                 460

Glu Glu Ile Ser Ile Gln Val Ser Asn Pro Ser Leu Leu Asp Pro Asp
465                 470                 475                 480

Gln Asp Ala Thr Tyr Phe Gly Ala Phe Lys Val Gln Asp Ile Asp Ser
                485                 490                 495

Ser Gly Arg Glu Asn Leu Tyr Phe Gln
                500                 505

<210> SEQ ID NO 12
<211> LENGTH: 492

<212> TYPE: PRT
<213> ORGANISM: Artificial
<220> FEATURE:
<223> OTHER INFORMATION: synthetic

<400> SEQUENCE: 12

```
Ala Gln Pro Phe Ala His Leu Thr Ile Asn Ala Thr Asp Ile Pro Ser
1               5                   10                  15

Gly Ser His Lys Val Ser Leu Ser Ser Trp Tyr His Asp Arg Gly Trp
            20                  25                  30

Ala Lys Ile Ser Asn Met Thr Phe Ser Asn Gly Lys Leu Ile Val Asn
        35                  40                  45

Gln Asp Gly Phe Tyr Tyr Leu Tyr Ala Asn Ile Ser Phe Arg His His
    50                  55                  60

Glu Thr Ser Gly Asp Leu Ala Thr Glu Tyr Leu Gln Leu Met Val Tyr
65                  70                  75                  80

Val Thr Lys Thr Ser Glu Lys Ile Pro Ser Ser His Thr Leu Met Lys
                85                  90                  95

Gly Gly Ser Thr Lys Tyr Trp Ser Gly Asn Ser Glu Phe His Phe Tyr
            100                 105                 110

Ser Ile Asn Val Gly Gly Phe Phe Lys Leu Arg Ser Gly Glu Glu Ile
        115                 120                 125

Ser Ile Glu Val Ser Asn Pro Ser Leu Leu Asp Pro Asp Gln Asp Ala
    130                 135                 140

Thr Tyr Phe Gly Ala Phe Lys Val Arg Asp Ile Asp Gly Gly Ser Gly
145                 150                 155                 160

Gly Gly Ser Gly Gly Gly Ser Gly Ala Gln Pro Phe Ala His Leu Thr
                165                 170                 175

Ile Asn Ala Thr Asp Ile Pro Ser Gly Ser His Lys Val Ser Leu Ser
            180                 185                 190

Ser Trp Tyr His Asp Arg Gly Trp Ala Lys Ile Ser Asn Met Thr Phe
        195                 200                 205

Ser Asn Gly Lys Leu Ile Val Asn Gln Asp Gly Phe Tyr Tyr Leu Tyr
    210                 215                 220

Ala Asn Ile Ser Phe Arg His His Glu Thr Ser Gly Asp Leu Ala Thr
225                 230                 235                 240

Glu Tyr Leu Gln Leu Met Val Tyr Val Thr Lys Thr Ser Glu Lys Ile
                245                 250                 255

Pro Ser Ser His Thr Leu Met Lys Gly Gly Ser Thr Lys Tyr Trp Ser
            260                 265                 270

Gly Asn Ser Glu Phe His Phe Tyr Ser Ile Asn Val Gly Gly Phe Phe
        275                 280                 285

Lys Leu Arg Ser Gly Glu Glu Ile Ser Ile Glu Val Ser Asn Pro Ser
    290                 295                 300

Leu Leu Asp Pro Asp Gln Asp Ala Thr Tyr Phe Gly Ala Phe Lys Val
305                 310                 315                 320

Arg Asp Ile Asp Gly Gly Ser Gly Gly Gly Ser Gly Gly Gly Ser Gly
                325                 330                 335

Ala Gln Pro Phe Ala His Leu Thr Ile Asn Ala Thr Asp Ile Pro Ser
            340                 345                 350

Gly Ser His Lys Val Ser Leu Ser Ser Trp Tyr His Asp Arg Gly Trp
        355                 360                 365

Ala Lys Ile Ser Asn Met Thr Phe Ser Asn Gly Lys Leu Ile Val Asn
    370                 375                 380
```

```
Gln Asp Gly Phe Tyr Tyr Leu Tyr Ala Asn Ile Ser Phe Arg His His
385                 390                 395                 400

Glu Thr Ser Gly Asp Leu Ala Thr Glu Tyr Leu Gln Leu Met Val Tyr
            405                 410                 415

Val Thr Lys Thr Ser Glu Lys Ile Pro Ser Ser His Thr Leu Met Lys
            420                 425                 430

Gly Gly Ser Thr Lys Tyr Trp Ser Gly Asn Ser Glu Phe His Phe Tyr
            435                 440                 445

Ser Ile Asn Val Gly Gly Phe Phe Lys Leu Arg Ser Gly Glu Glu Ile
        450                 455                 460

Ser Ile Glu Val Ser Asn Pro Ser Leu Leu Asp Pro Asp Gln Asp Ala
465                 470                 475                 480

Thr Tyr Phe Gly Ala Phe Lys Val Arg Asp Ile Asp
            485                 490

<210> SEQ ID NO 13
<211> LENGTH: 492
<212> TYPE: PRT
<213> ORGANISM: Artificial
<220> FEATURE:
<223> OTHER INFORMATION: synthetic

<400> SEQUENCE: 13

Ala Gln Pro Phe Ala His Leu Thr Ile Asn Ala Thr Asp Ile Pro Ser
1               5                   10                  15

Gly Ser His Lys Val Ser Leu Ser Ser Trp Tyr His Asp Arg Gly Trp
            20                  25                  30

Ala Lys Ile Ser Asn Met Thr Phe Ser Asn Gly Lys Leu Ile Val Asn
            35                  40                  45

Gln Asp Gly Phe Tyr Tyr Leu Tyr Ala Asn Ile Ser Phe Arg His Asn
        50                  55                  60

Glu Thr Ser Gly Asp Leu Ala Thr Glu Tyr Leu Gln Leu Met Val Tyr
65                  70                  75                  80

Val Thr Lys Thr Ser Glu Lys Ile Pro Ser Ser His Thr Leu Met Lys
            85                  90                  95

Gly Gly Ser Thr Lys Tyr Trp Ser Gly Asn Ser Glu Phe His Phe Tyr
            100                 105                 110

Ser Ile Asn Val Gly Gly Phe Phe Lys Leu Arg Ser Gly Glu Glu Ile
        115                 120                 125

Ser Ile Glu Val Ser Asn Pro Ser Leu Leu Asp Pro Asp Gln Asp Ala
    130                 135                 140

Thr Tyr Phe Gly Ala Phe Lys Val Arg Asp Ile Asp Gly Gly Ser Gly
145                 150                 155                 160

Gly Gly Ser Gly Gly Gly Ser Gly Ala Gln Pro Phe Ala His Leu Thr
            165                 170                 175

Ile Asn Arg Thr Asp Ile Pro Ser Gly Ser His Lys Val Ser Leu Ser
            180                 185                 190

Ser Trp Tyr His Asp Arg Ala Trp Ala Lys Ile Ser Asn Met Thr Phe
            195                 200                 205

Ser Asn Gly Lys Leu Ile Val Asn Gln Asp Gly Phe Tyr Tyr Leu Tyr
        210                 215                 220

Ala Asn Ile Ser Phe Arg His His Glu Thr Ser Gly Asp Leu Ala Thr
225                 230                 235                 240

Glu Tyr Leu Gln Leu Met Val Tyr Val Thr Lys Thr Ser Glu Lys Ile
            245                 250                 255
```

```
Pro Ser Ser His Thr Leu Met Lys Gly Ser Thr Lys Tyr Trp Ser
            260                 265                 270

Gly Asn Ser Glu Phe His Phe Tyr Ser Ile Asn Val Gly Gly Phe Phe
            275                 280                 285

Lys Leu Arg Ser Gly Glu Glu Ile Ser Ile Glu Val Ser Asn Pro Ser
            290                 295                 300

Leu Leu Asp Pro Asp Gln Asp Ala Thr Tyr Phe Gly Ala Phe Lys Val
305                 310                 315                 320

Arg Asp Ile Asp Gly Gly Ser Gly Gly Ser Gly Gly Gly Ser Gly
                325                 330                 335

Ala Gln Pro Phe Ala His Leu Thr Ile Asn Arg Thr Asp Ile Pro Ser
            340                 345                 350

Gly Ser His Lys Val Ser Leu Ser Ser Trp Tyr His Asp Arg Ala Trp
            355                 360                 365

Ala Lys Ile Ser Asn Met Thr Phe Ser Asn Gly Lys Leu Ile Val Asn
            370                 375                 380

Gln Asp Gly Phe Tyr Tyr Leu Tyr Ala Asn Ile Ser Phe Arg His His
385                 390                 395                 400

Glu Thr Ser Gly Asp Leu Ala Thr Glu Tyr Leu Gln Leu Met Val Tyr
            405                 410                 415

Val Thr Lys Thr Ser Glu Lys Arg Pro Ser Ser His Thr Leu Met Lys
            420                 425                 430

Gly Gly Ser Thr Lys Tyr Trp Ser Gly Asn Ser Glu Phe His Phe Tyr
            435                 440                 445

Ser Ile Asn Val Gly Gly Phe Phe Lys Leu Arg Ser Gly Glu Glu Ile
450                 455                 460

Ser Ile Glu Val Ser Asn Pro Ser Leu Leu Asp Pro Asp Gln Asp Ala
465                 470                 475                 480

Thr Tyr Phe Gly Ala Phe Lys Val Arg Asp Ile Asp
                485                 490

<210> SEQ ID NO 14
<211> LENGTH: 492
<212> TYPE: PRT
<213> ORGANISM: Artificial
<220> FEATURE:
<223> OTHER INFORMATION: synthetic

<400> SEQUENCE: 14

Ala Gln Pro Phe Ala His Leu Thr Ile Asn Ala Thr Asp Ile Pro Ser
1               5                   10                  15

Gly Ser His Lys Val Ser Leu Ser Ser Trp Tyr His Asp Arg Gly Trp
            20                  25                  30

Ala Lys Ile Ser Asn Met Thr Phe Ser Asn Gly Lys Leu Ile Val Asn
            35                  40                  45

Gln Asp Gly Phe Tyr Tyr Leu Tyr Ala Asn Ile Ser Phe Arg His Asn
            50                  55                  60

Glu Thr Ser Gly Asp Leu Ala Thr Glu Tyr Leu Gln Leu Met Val Tyr
65                  70                  75                  80

Val Thr Lys Thr Ser Glu Lys Arg Pro Ser His Thr Leu Met Lys
            85                  90                  95

Gly Gly Ser Thr Lys Tyr Trp Ser Gly Asn Ser Glu Phe His Phe Tyr
            100                 105                 110

Ser Ile Asn Val Gly Gly Phe Phe Lys Leu Arg Ser Gly Glu Glu Ile
            115                 120                 125
```

```
Ser Ile Glu Val Ser Asn Pro Ser Leu Leu Asp Pro Asp Gln Asp Ala
    130                 135                 140

Thr Tyr Phe Gly Ala Phe Lys Val Arg Asp Ile Asp Gly Gly Ser Gly
145                 150                 155                 160

Gly Gly Ser Gly Gly Ser Gly Ala Gln Pro Phe Ala His Leu Thr
                165                 170                 175

Ile Asn Arg Thr Asp Ile Pro Ser Gly Ser His Lys Val Ser Leu Ser
            180                 185                 190

Ser Trp Tyr His Asp Arg Gly Trp Ala Lys Ile Ser Asn Met Thr Phe
        195                 200                 205

Ser Asn Gly Lys Leu Ile Val Asn Gln Asp Gly Phe Tyr Tyr Leu Tyr
    210                 215                 220

Ala Asn Ile Ser Phe Arg His Asn Glu Thr Ser Gly Asp Leu Ala Thr
225                 230                 235                 240

Glu Tyr Leu Gln Leu Met Val Tyr Val Thr Lys Thr Ser Glu Lys Ile
                245                 250                 255

Pro Ser Ser His Thr Leu Met Lys Gly Gly Ser Thr Lys Tyr Trp Ser
            260                 265                 270

Gly Asn Ser Glu Phe His Phe Tyr Ser Ile Asn Val Gly Gly Phe Phe
        275                 280                 285

Lys Leu Arg Ser Gly Glu Glu Ile Ser Ile Glu Val Ser Asn Pro Ser
    290                 295                 300

Leu Leu Asp Pro Asp Gln Asp Ala Thr Tyr Phe Gly Ala Phe Lys Val
305                 310                 315                 320

Arg Asp Ile Asp Gly Gly Ser Gly Gly Ser Gly Gly Gly Ser Gly
                325                 330                 335

Ala Gln Pro Phe Ala His Leu Thr Ile Asn Arg Thr Asp Ile Pro Ser
            340                 345                 350

Gly Ser His Lys Val Ser Leu Ser Ser Trp Tyr His Asp Arg Ala Trp
        355                 360                 365

Ala Lys Ile Ser Asn Met Thr Phe Ser Asn Gly Lys Leu Ile Val Asn
    370                 375                 380

Gln Asp Gly Phe Tyr Tyr Leu Tyr Ala Asn Ile Ser Phe Arg His His
385                 390                 395                 400

Glu Thr Ser Gly Asp Leu Ala Thr Glu Tyr Leu Gln Leu Met Val Tyr
                405                 410                 415

Val Thr Lys Thr Ser Glu Lys Arg Pro Ser Ser His Thr Leu Met Lys
            420                 425                 430

Gly Gly Ser Thr Lys Tyr Trp Ser Gly Asn Ser Glu Phe His Phe Tyr
        435                 440                 445

Ser Ile Asn Val Gly Gly Phe Phe Lys Leu Arg Ser Gly Glu Glu Ile
    450                 455                 460

Ser Ile Glu Val Ser Asn Pro Ser Leu Leu Asp Pro Asp Gln Asp Ala
465                 470                 475                 480

Thr Tyr Phe Gly Ala Phe Lys Val Arg Asp Ile Asp
                485                 490
```

<210> SEQ ID NO 15
<211> LENGTH: 495
<212> TYPE: PRT
<213> ORGANISM: Artificial
<220> FEATURE:
<223> OTHER INFORMATION: synthetic

<400> SEQUENCE: 15

```
Ala Gln Pro Phe Ala His Leu Thr Ile Asn Ala Thr Asp Ile Pro Ser
1               5                   10                  15

Gly Ser His Lys Val Ser Leu Ser Ser Trp Tyr His Asp Arg Gly Trp
            20                  25                  30

Ala Lys Ile Ser Asn Met Thr Phe Ser Asn Gly Lys Leu Ile Val Asn
            35                  40                  45

Gln Asp Gly Phe Tyr Tyr Leu Tyr Ala Asn Ile Ser Phe Arg Gly Gly
        50                  55                  60

Ser His His Glu Thr Ser Gly Asp Leu Ala Thr Glu Tyr Leu His Leu
65                  70                  75                  80

Met Val Tyr Val Thr Lys Thr Ser Glu Lys Ile Pro Ser Ser His Thr
                85                  90                  95

Leu Met Lys Gly Gly Ser Thr Lys Tyr Trp Ser Gly Asn Ser Glu Phe
                100                 105                 110

His Phe Tyr Ser Ile Asn Val Gly Gly Phe Phe Lys Leu Arg Ser Gly
            115                 120                 125

Glu Glu Ile Ser Ile Glu Val Ser Asn Pro Ser Leu Leu Asp Pro Asp
        130                 135                 140

Gln Asp Ala Thr Tyr Phe Gly Ala Phe Lys Val Arg Asp Ile Asp Gly
145                 150                 155                 160

Gly Ser Gly Gly Gly Ser Gly Gly Ser Gly Ala Gln Pro Phe Ala
                165                 170                 175

His Leu Thr Ile Asn Ala Thr Asp Ile Pro Ser Gly Ser His Lys Val
            180                 185                 190

Ser Leu Ser Ser Trp Tyr His Asp Arg Gly Trp Ala Glu Ile Ser Asn
        195                 200                 205

Met Thr Phe Ser Asn Gly Lys Leu Ile Val Asn Gln Asp Gly Phe Tyr
    210                 215                 220

Tyr Leu Tyr Ala Asn Ile Ser Phe Arg His His Glu Thr Ser Gly Asp
225                 230                 235                 240

Leu Ala Thr Glu Tyr Leu His Leu Met Val Tyr Val Thr Lys Thr Ser
                245                 250                 255

Glu Lys Ile Pro Ser Ser His Thr Leu Met Lys Gly Gly Ser Thr Lys
                260                 265                 270

Tyr Trp Ser Gly Asn Ser Glu Tyr Tyr Phe Tyr Ser Ile Asn Val Gly
        275                 280                 285

Gly Phe Phe Lys Leu Arg Ser Gly Glu Glu Ile Ser Ile Glu Val Ser
        290                 295                 300

Asn Pro Ser Leu Leu Asp Pro Asp Gln Asp Ala Thr Tyr Phe Gly Ala
305                 310                 315                 320

Phe Lys Val Arg Asp Ile Asp Gly Gly Ser Gly Gly Gly Ser Gly Gly
                325                 330                 335

Gly Ser Gly Ala Gln Pro Phe Ala His Leu Thr Ile Asn Ala Thr Asp
            340                 345                 350

Ile Pro Ser Gly Ser His Lys Val Ser Leu Ser Ser Trp Tyr His Asp
            355                 360                 365

Arg Gly Trp Ala Glu Ile Ser Asn Met Thr Phe Ser Asn Gly Lys Leu
        370                 375                 380

Ile Val Asn Gln Asp Gly Phe Tyr Tyr Leu Tyr Ala Asn Ile Ser Phe
385                 390                 395                 400

Arg His His Glu Thr Ser Gly Asp Leu Ala Thr Glu Tyr Leu His Leu
                405                 410                 415

Met Val Tyr Val Thr Lys Thr Ser Glu Lys Ile Pro Ser Ser His Thr
```

```
                    420                 425                 430
Leu Met Lys Gly Gly Ser Thr Lys Tyr Trp Ser Gly Asn Ser Glu Tyr
            435                 440                 445

Tyr Phe Tyr Ser Ile Asn Val Gly Gly Phe Phe Lys Leu Arg Ser Gly
            450                 455                 460

Glu Glu Ile Ser Ile Glu Val Ser Asn Pro Ser Leu Leu Asp Pro Asp
465                 470                 475                 480

Gln Asp Ala Thr Tyr Phe Gly Ala Phe Lys Val Arg Asp Ile Asp
            485                 490                 495

<210> SEQ ID NO 16
<211> LENGTH: 498
<212> TYPE: PRT
<213> ORGANISM: Artificial
<220> FEATURE:
<223> OTHER INFORMATION: synthetic

<400> SEQUENCE: 16

Ala Gln Pro Phe Ala His Leu Thr Ile Asn Ala Thr Asp Ile Pro Ser
1               5                   10                  15

Gly Ser His Lys Val Ser Leu Ser Ser Trp Tyr His Asp Arg Gly Trp
            20                  25                  30

Ala Lys Ile Ser Asn Met Thr Phe Ser Asn Gly Lys Leu Ile Val Asn
        35                  40                  45

Gln Asp Gly Phe Tyr Tyr Leu Tyr Ala Asn Ile Ser Phe Arg Gly Gly
    50                  55                  60

Ser His His Glu Thr Ser Gly Asp Leu Ala Thr Glu Tyr Leu His Leu
65                  70                  75                  80

Met Val Tyr Val Thr Lys Thr Ser Glu Lys Ile Pro Ser Ser His Thr
                85                  90                  95

Leu Met Lys Gly Gly Ser Thr Lys Tyr Trp Ser Gly Asn Ser Glu Phe
            100                 105                 110

His Phe Tyr Ser Ile Asn Val Gly Gly Phe Phe Lys Leu Arg Ser Gly
            115                 120                 125

Glu Glu Ile Ser Ile Glu Val Ser Asn Pro Ser Leu Leu Asp Pro Asp
130                 135                 140

Gln Asp Ala Thr Tyr Phe Gly Ala Phe Lys Val Arg Asp Ile Asp Gly
145                 150                 155                 160

Gly Ser Gly Gly Gly Ser Gly Gly Ser Gly Ala Gln Pro Phe Ala
            165                 170                 175

His Leu Thr Ile Asn Ala Thr Asp Ile Pro Ser Gly Ser His Lys Val
            180                 185                 190

Ser Leu Ser Ser Trp Tyr His Asp Arg Gly Trp Ala Lys Ile Ser Asn
            195                 200                 205

Met Thr Phe Ser Asn Gly Lys Leu Ile Val Asn Gln Asp Gly Phe Tyr
    210                 215                 220

Tyr Leu Tyr Ala Asn Ile Ser Phe Arg Gly Gly Ser His His Glu Thr
225                 230                 235                 240

Ser Gly Asp Leu Ala Thr Glu Tyr Leu His Leu Met Val Tyr Val Thr
            245                 250                 255

Lys Thr Ser Glu Lys Ile Pro Ser Ser His Thr Leu Met Lys Gly Gly
            260                 265                 270

Ser Thr Lys Tyr Trp Ser Gly Asn Ser Glu Phe His Phe Tyr Ser Ile
        275                 280                 285

Asn Val Gly Gly Phe Phe Lys Leu Arg Ser Gly Glu Glu Ile Ser Ile
```

```
                290                 295                 300
Glu Val Ser Asn Pro Ser Leu Leu Asp Pro Asp Gln Asp Ala Thr Tyr
305                 310                 315                 320

Phe Gly Ala Phe Lys Val Arg Asp Ile Asp Gly Gly Ser Gly Gly Gly
                325                 330                 335

Ser Gly Gly Gly Ser Gly Ala Gln Pro Phe Ala His Leu Thr Ile Asn
            340                 345                 350

Ala Thr Asp Ile Pro Ser Gly Ser His Lys Val Ser Leu Ser Ser Trp
        355                 360                 365

Tyr His Asp Arg Gly Trp Ala Glu Ile Ser Asn Met Thr Phe Ser Asn
    370                 375                 380

Gly Lys Leu Ile Val Asn Gln Asp Gly Phe Tyr Leu Tyr Ala Asn
385                 390                 395                 400

Ile Ser Phe Arg His His Glu Thr Ser Gly Asp Leu Ala Thr Glu Tyr
                405                 410                 415

Leu His Leu Met Val Tyr Val Thr Lys Thr Ser Glu Lys Ile Pro Ser
                420                 425                 430

Ser His Thr Leu Met Lys Gly Gly Ser Thr Lys Tyr Trp Ser Gly Asn
            435                 440                 445

Ser Glu Tyr Tyr Phe Tyr Ser Ile Asn Val Gly Gly Phe Phe Lys Leu
        450                 455                 460

Arg Ser Gly Glu Glu Ile Ser Ile Glu Val Ser Asn Pro Ser Leu Leu
465                 470                 475                 480

Asp Pro Asp Gln Asp Ala Thr Tyr Phe Gly Ala Phe Lys Val Arg Asp
                485                 490                 495

Ile Asp

<210> SEQ ID NO 17
<211> LENGTH: 471
<212> TYPE: PRT
<213> ORGANISM: Artificial
<220> FEATURE:
<223> OTHER INFORMATION: synthetic

<400> SEQUENCE: 17

Ser Asp Lys Pro Val Ala His Val Val Ala Asn Pro Gln Ala Glu Gly
1               5                   10                  15

Gln Leu Gln Trp Leu Asn Arg Arg Ala Asn Ala Leu Leu Ala Asn Gly
                20                  25                  30

Val Glu Leu Arg Asp Asn Gln Leu Val Val Pro Ser Glu Gly Leu Tyr
            35                  40                  45

Leu Ile Tyr Ser Gln Val Leu Phe Lys Gly Gln Gly Cys Pro Ser Thr
        50                  55                  60

His Val Leu Leu Thr His Thr Ile Ser Arg Ile Ala Val Ser Tyr Gln
65                  70                  75                  80

Thr Lys Val Asn Leu Leu Ser Ala Ile Lys Ser Pro Cys Gln Arg Glu
                85                  90                  95

Thr Pro Glu Gly Ala Glu Ala Lys Pro Trp Tyr Glu Pro Ile Tyr Leu
            100                 105                 110

Gly Gly Val Phe Gln Leu Glu Lys Gly Asp Arg Leu Ser Ala Glu Ile
        115                 120                 125

Asn Arg Pro Asp Tyr Leu Asp Phe Ala Glu Ser Gly Gln Val Tyr Phe
    130                 135                 140

Gly Ile Ile Ala Leu Gly Gly Ser Gly Gly Gly Ser Gly Gly Gly Ser
145                 150                 155                 160
```

Gly Ser Asp Lys Pro Val Ala His Val Val Ala Asn Pro Gln Ala Glu
165                 170                 175

Gly Gln Leu Gln Trp Leu Asn Arg Arg Ala Asn Ala Leu Leu Ala Asn
        180                 185                 190

Gly Val Glu Leu Arg Asp Asn Gln Leu Val Val Pro Ser Glu Gly Leu
    195                 200                 205

Tyr Leu Ile Tyr Ser Gln Val Leu Phe Lys Gly Gln Gly Cys Pro Ser
210                 215                 220

Thr His Val Leu Leu Thr His Thr Ile Ser Arg Ile Ala Val Ser Tyr
225                 230                 235                 240

Gln Thr Lys Val Asn Leu Leu Ser Ala Ile Lys Ser Pro Cys Gln Arg
                245                 250                 255

Glu Thr Pro Glu Gly Ala Glu Ala Lys Pro Trp Tyr Glu Pro Ile Tyr
            260                 265                 270

Leu Gly Gly Val Phe Gln Leu Glu Lys Gly Asp Arg Leu Ser Ala Glu
        275                 280                 285

Ile Asn Arg Pro Asp Tyr Leu Asp Phe Ala Glu Ser Gly Gln Val Tyr
    290                 295                 300

Phe Gly Ile Ile Ala Leu Gly Gly Ser Gly Gly Ser Gly Gly Gly Gly
305                 310                 315                 320

Ser Gly Ser Asp Lys Pro Val Ala His Val Val Ala Asn Pro Gln Ala
                325                 330                 335

Glu Gly Gln Leu Gln Trp Leu Asn Arg Arg Ala Asn Ala Leu Leu Ala
            340                 345                 350

Asn Gly Val Glu Leu Arg Asp Asn Gln Leu Val Val Pro Ser Glu Gly
        355                 360                 365

Leu Tyr Leu Ile Tyr Ser Gln Val Leu Phe Lys Gly Gln Gly Cys Pro
370                 375                 380

Ser Thr His Val Leu Leu Thr His Thr Ile Ser Arg Ile Ala Val Ser
385                 390                 395                 400

Tyr Gln Thr Lys Val Asn Leu Leu Ser Ala Ile Lys Ser Pro Cys Gln
                405                 410                 415

Arg Glu Thr Pro Glu Gly Ala Glu Ala Lys Pro Trp Tyr Glu Pro Ile
            420                 425                 430

Tyr Leu Gly Gly Val Phe Gln Leu Glu Lys Gly Asp Arg Leu Ser Ala
        435                 440                 445

Glu Ile Asn Arg Pro Asp Tyr Leu Asp Phe Ala Glu Ser Gly Gln Val
    450                 455                 460

Tyr Phe Gly Ile Ile Ala Leu
465                 470

<210> SEQ ID NO 18
<211> LENGTH: 471
<212> TYPE: PRT
<213> ORGANISM: Artificial
<220> FEATURE:
<223> OTHER INFORMATION: synthetic

<400> SEQUENCE: 18

Ser Asp Lys Pro Val Ala His Val Val Ala Asn Pro Gln Ala Glu Gly
1               5                   10                  15

Gln Leu Gln Trp Leu Asn Arg Arg Ala Asn Ala Leu Leu Ala Asn Gly
            20                  25                  30

Val Glu Leu Arg Asp Asn Gln Leu Val Val Pro Ser Glu Gly Leu Tyr
        35                  40                  45

```
Leu Ile Tyr Ser Gln Val Leu Phe Lys Gly Gln Gly Cys Pro Ser Thr
            50                  55                  60

His Val Leu Leu Thr His Thr Ile Ser Arg Ile Ala Val Ser Gln Gln
 65                  70                  75                  80

Thr Lys Val Asn Leu Leu Ser Ala Ile Lys Ser Pro Cys Gln Arg Glu
                 85                  90                  95

Thr Pro Glu Gly Ala Glu Ala Lys Pro Trp Tyr Glu Pro Ile Tyr Leu
            100                 105                 110

Gly Gly Val Phe Gln Leu Glu Lys Gly Asp Arg Leu Ser Ala Glu Ile
            115                 120                 125

Asn Arg Pro Asp Tyr Leu Asp Phe Ala Glu Ser Gly Gln Val Tyr Phe
            130                 135                 140

Gly Ile Ile Ala Leu Gly Gly Ser Gly Gly Ser Gly Gly Gly Gly Ser
145                 150                 155                 160

Gly Ser Asp Lys Pro Val Ala His Val Val Ala Asn Pro Gln Ala Glu
            165                 170                 175

Gly Gln Leu Gln Trp Leu Asn Arg Arg Ala Asn Ala Leu Leu Ala Asn
            180                 185                 190

Gly Val Glu Leu Arg Asp Asn Gln Leu Val Val Pro Ser Glu Gly Leu
            195                 200                 205

Tyr Leu Ile Tyr Ser Gln Val Leu Phe Lys Gly Gln Gly Cys Pro Ser
210                 215                 220

Thr His Val Leu Leu Thr His Thr Ile Ser Arg Ile Ala Val Thr Tyr
225                 230                 235                 240

Gln Thr Lys Val Asn Leu Leu Ser Ala Ile Lys Ser Pro Cys Gln Arg
                245                 250                 255

Glu Thr Pro Glu Gly Ala Glu Ala Lys Pro Trp Tyr Glu Pro Ile Tyr
            260                 265                 270

Leu Gly Gly Val Phe Gln Leu Glu Lys Gly Asp Arg Leu Ser Ala Glu
            275                 280                 285

Ile Asn Arg Pro Asp Tyr Leu Asp Phe Ala Glu Ser Gly Gln Val Tyr
290                 295                 300

Phe Gly Ile Ile Ala Leu Gly Gly Ser Gly Gly Gly Ser Gly Gly Gly
305                 310                 315                 320

Ser Gly Ser Asp Lys Pro Val Ala His Val Val Ala Asn Pro Gln Ala
            325                 330                 335

Glu Gly Gln Leu Gln Trp Leu Asn Arg Arg Ala Asn Ala Leu Leu Ala
            340                 345                 350

Asn Gly Val Glu Leu Arg Asp Asn Gln Leu Val Val Pro Ser Glu Gly
            355                 360                 365

Leu Tyr Leu Ile Tyr Ser Gln Val Leu Phe Lys Gly Gln Gly Cys Pro
            370                 375                 380

Ser Thr His Val Leu Leu Thr His Thr Ile Ser Arg Ile Ala Val Thr
385                 390                 395                 400

Tyr Gln Thr Lys Val Asn Leu Leu Ser Ala Ile Lys Ser Pro Cys Gln
                405                 410                 415

Arg Glu Thr Pro Glu Gly Ala Glu Ala Lys Pro Trp Tyr Glu Pro Ile
            420                 425                 430

Tyr Leu Gly Gly Val Phe Gln Leu Glu Lys Gly Asp Arg Leu Ser Ala
            435                 440                 445

Glu Ile Asn Arg Pro Asp Tyr Leu Asp Phe Ala Glu Ser Gly Gln Val
450                 455                 460
```

```
Tyr Phe Gly Ile Ile Ala Leu
465                 470

<210> SEQ ID NO 19
<211> LENGTH: 471
<212> TYPE: PRT
<213> ORGANISM: Artificial
<220> FEATURE:
<223> OTHER INFORMATION: synthetic

<400> SEQUENCE: 19

Ser Asp Lys Pro Val Ala His Val Val Ala Asn Pro Gln Ala Glu Gly
1               5                   10                  15

Gln Leu Gln Trp Leu Asn Arg Arg Ala Asn Ala Leu Leu Ala Asn Gly
            20                  25                  30

Val Glu Leu Arg Asp Asn Gln Leu Val Val Pro Ser Glu Gly Leu Tyr
        35                  40                  45

Leu Ile Tyr Ser Gln Val Leu Phe Lys Gly Gln Gly Cys Pro Ser Thr
    50                  55                  60

His Val Leu Leu Thr His Thr Ile Ser Arg Ile Ala Val Ser Gln Gln
65                  70                  75                  80

Thr Lys Val Asn Leu Leu Ser Ala Ile Lys Ser Pro Cys Gln Arg Glu
                85                  90                  95

Thr Pro Glu Gly Ala Glu Ala Lys Pro Trp Tyr Glu Pro Ile Tyr Leu
            100                 105                 110

Gly Gly Val Phe Gln Leu Glu Lys Gly Asp Arg Leu Ser Ala Glu Ile
        115                 120                 125

Asn Arg Pro Asp Tyr Leu Asp Phe Ala Glu Ser Gly Gln Val Tyr Phe
    130                 135                 140

Gly Ile Ile Ala Leu Gly Gly Ser Gly Gly Ser Gly Gly Gly Ser
145                 150                 155                 160

Gly Ser Asp Lys Pro Val Ala His Val Val Ala Asn Pro Gln Ala Glu
                165                 170                 175

Gly Gln Leu Gln Trp Leu Asn Arg Arg Ala Asn Ala Leu Leu Ala Asn
            180                 185                 190

Gly Val Glu Leu Arg Asp Asn Gln Leu Val Val Pro Ser Glu Gly Leu
        195                 200                 205

Tyr Leu Ile Tyr Ser Gln Val Leu Phe Lys Gly Gln Gly Cys Pro Ser
    210                 215                 220

Thr His Val Leu Leu Thr His Thr Ile Ser Arg Ile Ala Val Ser Gln
225                 230                 235                 240

Gln Thr Lys Val Asn Leu Leu Ser Ala Ile Lys Ser Pro Cys Gln Arg
                245                 250                 255

Glu Thr Pro Glu Gly Ala Glu Ala Lys Pro Trp Tyr Glu Pro Ile Tyr
            260                 265                 270

Leu Gly Gly Val Phe Gln Leu Glu Lys Gly Asp Arg Leu Ser Ala Glu
        275                 280                 285

Ile Asn Arg Pro Asp Tyr Leu Asp Phe Ala Glu Ser Gly Gln Val Tyr
    290                 295                 300

Phe Gly Ile Ile Ala Leu Gly Gly Ser Gly Gly Ser Gly Gly Gly
305                 310                 315                 320

Ser Gly Ser Asp Lys Pro Val Ala His Val Val Ala Asn Pro Gln Ala
                325                 330                 335

Glu Gly Gln Leu Gln Trp Thr Asn Arg Phe Ala Asn Ala Leu Leu Ala
            340                 345                 350
```

Asn Gly Val Glu Leu Arg Asp Asn Gln Leu Val Val Pro Ser Glu Gly
          355                 360                 365

Leu Tyr Leu Ile Tyr Ser Gln Val Leu Phe Lys Gly Gln Gly Cys Pro
370                 375                 380

Ser Thr His Val Leu Leu Thr His Thr Ile Ser Arg Ile Ala Val Thr
385                 390                 395                 400

Tyr Gln Thr Lys Val Asn Leu Leu Ser Ala Ile Lys Ser Pro Cys Gln
                405                 410                 415

Arg Glu Thr Pro Glu Gly Ala Glu Ala Lys Pro Trp Tyr Glu Pro Ile
            420                 425                 430

Tyr Leu Gly Gly Val Phe Gln Leu Glu Lys Gly Asp Arg Leu Ser Ala
        435                 440                 445

Glu Ile Asn Arg Pro Asp Tyr Leu Asp Phe Ala Glu Ser Gly Gln Val
450                 455                 460

Tyr Phe Gly Ile Ile Ala Leu
465                 470

<210> SEQ ID NO 20
<211> LENGTH: 471
<212> TYPE: PRT
<213> ORGANISM: Artificial
<220> FEATURE:
<223> OTHER INFORMATION: synthetic

<400> SEQUENCE: 20

Ser Asp Lys Pro Val Ala His Val Val Ala Asn Pro Gln Ala Glu Gly
1               5                   10                  15

Gln Leu Gln Trp Leu Asn Arg Arg Ala Asn Ala Leu Leu Ala Asn Gly
            20                  25                  30

Val Glu Leu Arg Asp Asn Gln Leu Val Val Pro Ser Glu Gly Leu Tyr
        35                  40                  45

Leu Ile Tyr Ser Gln Val Leu Phe Lys Gly Gln Gly Cys Pro Ser Thr
    50                  55                  60

His Val Leu Leu Thr His Thr Ile Ser Arg Ile Ala Val Ser Tyr Gln
65                  70                  75                  80

Thr Lys Val Asn Leu Leu Ser Ala Ile Lys Ser Pro Cys Gln Arg Glu
                85                  90                  95

Thr Pro Glu Gly Ala Glu Ala Lys Pro Trp Tyr Glu Pro Ile Tyr Leu
            100                 105                 110

Gly Gly Val Phe Gln Leu Glu Lys Gly Asp Arg Leu Ser Ala Glu Ile
        115                 120                 125

Asn Arg Pro Asp Tyr Leu Val Phe Ala Glu Ser Gly Gln Val Tyr Phe
    130                 135                 140

Gly Ile Ile Ala Leu Gly Gly Ser Gly Gly Ser Gly Gly Gly Ser
145                 150                 155                 160

Gly Ser Asp Lys Pro Val Ala His Val Val Ala Asn Pro Gln Ala Glu
                165                 170                 175

Gly Gln Leu Gln Trp Thr Asn Arg Phe Ala Asn Ala Leu Leu Ala Asn
            180                 185                 190

Gly Val Glu Leu Arg Asp Asn Gln Leu Val Val Pro Ser Glu Gly Leu
        195                 200                 205

Tyr Leu Ile Tyr Ser Gln Val Leu Phe Lys Gly Gln Gly Cys Pro Ser
    210                 215                 220

Thr His Val Leu Leu Thr His Thr Ile Ser Arg Ile Ala Val Ser Tyr
225                 230                 235                 240

Gln Thr Lys Val Asn Leu Leu Ser Ala Ile Lys Ser Pro Cys Gln Arg
            245                 250                 255

Glu Thr Pro Glu Gly Ala Glu Ala Lys Pro Trp Tyr Glu Pro Ile Tyr
        260                 265                 270

Leu Gly Gly Val Phe Gln Leu Glu Lys Gly Asp Arg Leu Ser Ala Glu
    275                 280                 285

Ile Asn Arg Pro Asp Tyr Leu Asp Phe Ala Glu Ser Gly Gln Val Tyr
290                 295                 300

Phe Gly Ile Ile Ala Leu Gly Gly Ser Gly Gly Ser Gly Gly Gly Gly
305                 310                 315                 320

Ser Gly Ser Asp Lys Pro Val Ala His Val Val Ala Asn Pro Gln Ala
            325                 330                 335

Glu Gly Gln Leu Gln Trp Thr Asn Arg Phe Ala Asn Ala Leu Leu Ala
        340                 345                 350

Asn Gly Val Glu Leu Arg Asp Asn Gln Leu Val Val Pro Ser Glu Gly
    355                 360                 365

Leu Tyr Leu Ile Tyr Ser Gln Val Leu Phe Lys Gly Gln Gly Cys Pro
370                 375                 380

Ser Thr His Val Leu Leu Thr His Thr Ile Ser Arg Ile Ala Val Ser
385                 390                 395                 400

Tyr Gln Thr Lys Val Asn Leu Leu Ser Ala Ile Lys Ser Pro Cys Gln
            405                 410                 415

Arg Glu Thr Pro Glu Gly Ala Glu Ala Lys Pro Trp Tyr Glu Pro Ile
        420                 425                 430

Tyr Leu Gly Gly Val Phe Gln Leu Glu Lys Gly Asp Arg Leu Ser Ala
    435                 440                 445

Glu Ile Asn Arg Pro Asp Tyr Leu Asp Phe Ala Glu Ser Gly Gln Val
450                 455                 460

Tyr Phe Gly Ile Ile Ala Leu
465                 470

<210> SEQ ID NO 21
<211> LENGTH: 470
<212> TYPE: PRT
<213> ORGANISM: Artificial
<220> FEATURE:
<223> OTHER INFORMATION: synthetic

<400> SEQUENCE: 21

Ser Asp Lys Pro Val Ala His Val Val Ala Asn Pro Gln Ala Glu Gly
1               5                   10                  15

Gln Leu Gln Trp Leu Asn Arg Arg Ala Asn Ala Leu Leu Ala Asn Gly
            20                  25                  30

Val Glu Leu Arg Asp Asn Gln Leu Val Val Pro Ser Glu Gly Leu Tyr
        35                  40                  45

Leu Ile Tyr Ser Gln Val Leu Phe Lys Gly Gln Gly Cys Pro Ser Thr
    50                  55                  60

His Val Leu Leu Thr His Thr Ile Ser Arg Ile Ala Val Ser Tyr Gln
65                  70                  75                  80

Thr Lys Val Asn Leu Leu Ser Ala Ile Lys Ser Pro Cys Gln Arg Glu
                85                  90                  95

Thr Pro Glu Gly Ala Glu Ala Lys Pro Trp Tyr Glu Pro Ile Tyr Leu
            100                 105                 110

Gly Gly Val Phe Gln Leu Glu Lys Gly Asp Arg Leu Ser Ala Glu Ile
        115                 120                 125

```
Asn Arg Pro Asp Tyr Leu Val Phe Ala Glu Ser Gly Gln Val Tyr Phe
    130                 135                 140

Gly Ile Ile Ala Leu Gly Gly Ser Gly Gly Ser Gly Gly Gly Ser
145                 150                 155                 160

Gly Ser Asp Lys Pro Val Ala His Val Val Ala Asn Pro Gln Ala Glu
                165                 170                 175

Gly Gln Leu Gln Trp Leu Asn Arg Arg Ala Asn Ala Leu Leu Ala Asn
                180                 185                 190

Gly Val Glu Leu Arg Asp Asn Gln Leu Val Val Pro Ser Glu Gly Leu
                195                 200                 205

Tyr Leu Ile Tyr Ser Gln Val Leu Phe Lys Gly Gln Gly Cys Pro Ser
                210                 215                 220

Thr His Val Leu Leu Thr His Thr Ile Ser Arg Ile Ala Val Ser Tyr
225                 230                 235                 240

Gln Thr Lys Val Asn Leu Leu Ser Ala Ile Lys Ser Pro Cys Gln Arg
                245                 250                 255

Glu Thr Pro Glu Gly Ala Glu Ala Lys Pro Trp Tyr Glu Pro Ile Tyr
                260                 265                 270

Leu Gly Gly Val Phe Gln Leu Glu Lys Gly Asp Arg Leu Ser Ala Glu
                275                 280                 285

Ile Asn Arg Pro Asp Tyr Leu Val Phe Ala Glu Ser Gly Gln Val Tyr
                290                 295                 300

Phe Gly Ile Ile Ala Leu Gly Gly Ser Gly Gly Ser Gly Gly Gly
305                 310                 315                 320

Ser Gly Asp Lys Pro Val Ala His Val Val Ala Asn Pro Gln Ala Glu
                325                 330                 335

Gly Gln Leu Gln Trp Thr Asn Arg Phe Ala Asn Ala Leu Leu Ala Asn
                340                 345                 350

Gly Val Glu Leu Arg Asp Asn Gln Leu Val Val Pro Ser Glu Gly Leu
                355                 360                 365

Tyr Leu Ile Tyr Ser Gln Val Leu Phe Lys Gly Gln Gly Cys Pro Ser
                370                 375                 380

Thr His Val Leu Leu Thr His Thr Ile Ser Arg Ile Ala Val Ser Tyr
385                 390                 395                 400

Gln Thr Lys Val Asn Leu Leu Ser Ala Ile Lys Ser Pro Cys Gln Arg
                405                 410                 415

Glu Thr Pro Glu Gly Ala Glu Ala Lys Pro Trp Tyr Glu Pro Ile Tyr
                420                 425                 430

Leu Gly Gly Val Phe Gln Leu Glu Lys Gly Asp Arg Leu Ser Ala Glu
                435                 440                 445

Ile Asn Arg Pro Asp Tyr Leu Asp Phe Ala Glu Ser Gly Gln Val Tyr
                450                 455                 460

Phe Gly Ile Ile Ala Leu
465                 470

<210> SEQ ID NO 22
<211> LENGTH: 513
<212> TYPE: PRT
<213> ORGANISM: Artificial
<220> FEATURE:
<223> OTHER INFORMATION: synthetic

<400> SEQUENCE: 22

Pro Gln Arg Val Ala Ala His Ile Thr Gly Thr Arg Gly Arg Ser Asn
1               5                   10                  15
```

```
Thr Leu Ser Ser Pro Asn Ser Lys Asn Glu Lys Ala Leu Gly Arg Lys
                 20                  25                  30

Ile Asn Ser Trp Glu Ser Ser Arg Ser Gly His Ser Phe Leu Ser Asn
             35                  40                  45

Leu His Leu Arg Asn Gly Glu Leu Val Ile His Glu Lys Gly Phe Tyr
         50                  55                  60

Tyr Ile Tyr Ser Gln Thr Tyr Phe Arg Phe Gln Glu Ile Lys Glu
 65                  70                  75                  80

Asn Thr Lys Asn Asp Lys Gln Met Val Gln Tyr Ile Tyr Lys Tyr Thr
                 85                  90                  95

Ser Tyr Pro Asp Pro Ile Leu Leu Met Lys Ser Ala Arg Asn Ser Cys
                100                 105                 110

Trp Ser Lys Asp Ala Glu Tyr Gly Leu Tyr Ser Ile Tyr Gln Gly Gly
            115                 120                 125

Ile Phe Glu Leu Lys Glu Asn Asp Arg Ile Phe Val Ser Val Thr Asn
        130                 135                 140

Glu His Leu Ile Asp Met Asp His Glu Ala Ser Phe Phe Gly Ala Phe
145                 150                 155                 160

Leu Val Gly Gly Gly Ser Gly Gly Gly Ser Gly Gly Gly Ser Gly Pro
                165                 170                 175

Gln Arg Val Ala Ala His Ile Thr Gly Thr Arg Gly Arg Ser Asn Thr
            180                 185                 190

Leu Ser Ser Pro Asn Ser Lys Asn Glu Lys Ala Leu Gly Arg Lys Ile
        195                 200                 205

Asn Ser Trp Glu Ser Ser Arg Ser Gly His Ser Phe Leu Ser Asn Leu
210                 215                 220

His Leu Arg Asn Gly Glu Leu Val Ile His Glu Lys Gly Phe Tyr Tyr
225                 230                 235                 240

Ile Tyr Ser Gln Thr Tyr Phe Arg Phe Gln Glu Ile Lys Glu Asn
            245                 250                 255

Thr Lys Asn Asp Lys Gln Met Val Gln Tyr Ile Tyr Lys Tyr Thr Ser
        260                 265                 270

Tyr Pro Asp Pro Ile Leu Leu Met Lys Ser Ala Arg Asn Ser Cys Trp
        275                 280                 285

Ser Lys Asp Ala Glu Tyr Gly Leu Tyr Ser Ile Tyr Gln Gly Gly Ile
        290                 295                 300

Phe Glu Leu Lys Glu Asn Asp Arg Ile Phe Val Ser Val Thr Asn Glu
305                 310                 315                 320

His Leu Ile Asp Met Asp His Glu Ala Ser Phe Phe Gly Ala Phe Leu
                325                 330                 335

Val Gly Gly Gly Ser Gly Gly Gly Ser Gly Gly Gly Ser Gly Pro Gln
            340                 345                 350

Arg Val Ala Ala His Ile Thr Gly Thr Arg Gly Arg Ser Asn Thr Leu
        355                 360                 365

Ser Ser Pro Asn Ser Lys Asn Glu Lys Ala Leu Gly Arg Lys Ile Asn
        370                 375                 380

Ser Trp Glu Ser Ser Arg Ser Gly His Ser Phe Leu Ser Asn Leu His
385                 390                 395                 400

Leu Arg Asn Gly Glu Leu Val Ile His Glu Lys Gly Phe Tyr Tyr Ile
                405                 410                 415

Tyr Ser Gln Thr Tyr Phe Arg Phe Gln Glu Ile Lys Glu Asn Thr
            420                 425                 430

Lys Asn Asp Lys Gln Met Val Gln Tyr Ile Tyr Lys Tyr Thr Ser Tyr
```

```
                    435                 440                 445
Pro Asp Pro Ile Leu Leu Met Lys Ser Ala Arg Asn Ser Cys Trp Ser
450                 455                 460

Lys Asp Ala Glu Tyr Gly Leu Tyr Ser Ile Tyr Gln Gly Gly Ile Phe
465                 470                 475                 480

Glu Leu Lys Glu Asn Asp Arg Ile Phe Val Ser Val Thr Asn Glu His
                    485                 490                 495

Leu Ile Asp Met Asp His Glu Ala Ser Phe Phe Gly Ala Phe Leu Val
                500                 505                 510

Gly

<210> SEQ ID NO 23
<211> LENGTH: 513
<212> TYPE: PRT
<213> ORGANISM: Artificial
<220> FEATURE:
<223> OTHER INFORMATION: synthetic

<400> SEQUENCE: 23

Pro Gln Arg Val Ala Ala His Ile Thr Gly Thr Arg Gly Arg Ser Asn
1               5                   10                  15

Thr Leu Ser Ser Pro Asn Ser Lys Asn Glu Lys Ala Leu Gly Arg Lys
                20                  25                  30

Ile Asn Ser Trp Glu Ser Ser Arg Ser Gly His Ser Phe Leu Ser Asn
            35                  40                  45

Leu His Leu Arg Asn Gly Glu Leu Val Ile His Glu Lys Gly Phe Tyr
        50                  55                  60

Tyr Ile Tyr Ser Gln Thr Ala Phe Arg Phe Ser Glu Glu Ile Lys Glu
65                  70                  75                  80

Asn Thr Lys Asn Asp Lys Gln Met Val Gln Tyr Ile Tyr Lys Tyr Thr
                85                  90                  95

Ser Tyr Pro Asp Pro Ile Leu Leu Met Lys Ser Ala Arg Asn Ser Cys
            100                 105                 110

Trp Ser Lys Asp Ala Glu Tyr Gly Leu Tyr Ser Ile Tyr Gln Gly Gly
        115                 120                 125

Ile Phe Glu Leu Lys Glu Asn Asp Arg Ile Phe Val Ser Val Thr Asn
130                 135                 140

Glu His Leu Ile Asp Met Asp His Glu Ala Ser Phe Phe Gly Ala Phe
145                 150                 155                 160

Leu Val Gly Gly Gly Ser Gly Gly Gly Ser Gly Gly Gly Ser Gly Pro
                165                 170                 175

Gln Arg Val Ala Ala His Ile Thr Gly Thr Arg Gly Arg Ser Asn Thr
            180                 185                 190

Leu Ser Ser Pro Asn Ser Lys Asn Glu Lys Ala Leu Gly Arg Lys Ile
        195                 200                 205

Asn Ser Trp Glu Ser Ser Arg Ser Gly His Ser Phe Leu Ser Asn Leu
    210                 215                 220

His Leu Arg Asn Gly Glu Leu Val Ile His Glu Lys Gly Phe Tyr Tyr
225                 230                 235                 240

Ile Tyr Ser Gln Thr Tyr Phe Arg Phe Gln Glu Glu Ile Lys Glu Asn
                245                 250                 255

Thr Lys Asn Asp Lys Gln Met Val Gln Tyr Ile Tyr Lys Tyr Thr Ser
            260                 265                 270

Tyr Pro Asp Pro Ile Leu Leu Met Lys Ser Ala Arg Asn Ser Cys Trp
        275                 280                 285
```

```
Ser Lys Asp Ala Glu Tyr Gly Leu Tyr Ser Ile Tyr Gln Gly Gly Ile
    290                 295                 300

Phe Glu Leu Lys Glu Asn Asp Arg Ile Phe Val Ser Val Thr Asn Glu
305                 310                 315                 320

His Leu Ile Asp Met His His Glu Ala Ser Phe Phe Gly Ala Phe Leu
                325                 330                 335

Val Gly Gly Gly Ser Gly Gly Gly Ser Gly Gly Gly Ser Gly Pro Gln
            340                 345                 350

Arg Val Ala Ala His Ile Thr Gly Thr Arg Gly Arg Ser Asn Thr Leu
            355                 360                 365

Ser Ser Pro Asn Ser Lys Asn Glu Lys Ala Leu Gly Arg Lys Ile Asn
    370                 375                 380

Ser Trp Glu Ser Ser Arg Ser Gly His Ser Phe Leu Ser Asn Leu His
385                 390                 395                 400

Leu Arg Asn Gly Glu Leu Val Ile His Glu Lys Gly Phe Tyr Tyr Ile
                405                 410                 415

Tyr Ser Gln Thr Tyr Phe Arg Phe Gln Glu Glu Ile Lys Glu Val Thr
            420                 425                 430

Arg Asn Asp Lys Gln Met Val Gln Tyr Ile Tyr Lys Trp Thr Asp Tyr
            435                 440                 445

Pro Asp Pro Ile Leu Leu Met Lys Ser Ala Arg Asn Ser Cys Trp Ser
450                 455                 460

Lys Asp Ala Glu Tyr Gly Leu Tyr Ser Ile Tyr Gln Gly Gly Ile Phe
465                 470                 475                 480

Glu Leu Lys Glu Asn Asp Arg Ile Phe Val Ser Val Thr Asn Glu His
                485                 490                 495

Leu Ile Asp Met His His Glu Ala Ser Phe Phe Gly Ala Phe Leu Val
            500                 505                 510

Gly

<210> SEQ ID NO 24
<211> LENGTH: 513
<212> TYPE: PRT
<213> ORGANISM: Artificial
<220> FEATURE:
<223> OTHER INFORMATION: synthetic

<400> SEQUENCE: 24

Pro Gln Arg Val Ala Ala His Ile Thr Gly Thr Arg Gly Arg Ser Asn
1               5                   10                  15

Thr Leu Ser Ser Pro Asn Ser Lys Asn Glu Lys Ala Leu Gly Arg Lys
            20                  25                  30

Ile Asn Ser Trp Glu Ser Ser Arg Ser Gly His Ser Phe Leu Ser Asn
        35                  40                  45

Leu His Leu Arg Asn Gly Glu Leu Val Ile His Glu Lys Gly Phe Tyr
    50                  55                  60

Tyr Ile Tyr Ser Gln Thr Ala Phe Arg Phe Ser Glu Glu Ile Lys Glu
65                  70                  75                  80

Asn Thr Lys Asn Asp Lys Gln Met Val Gln Tyr Ile Tyr Lys Tyr Thr
                85                  90                  95

Ser Tyr Pro Asp Pro Ile Leu Leu Met Lys Ser Ala Arg Asn Ser Cys
            100                 105                 110

Trp Ser Lys Asp Ala Glu Tyr Gly Leu Tyr Ser Ile Tyr Gln Gly Gly
        115                 120                 125
```

```
Ile Phe Glu Leu Lys Glu Asn Asp Arg Ile Phe Val Ser Val Thr Asn
    130                 135                 140
Glu His Leu Ile Asp Met Asp His Glu Ala Ser Phe Phe Gly Ala Phe
145                 150                 155                 160
Leu Val Gly Gly Gly Ser Gly Gly Gly Ser Gly Gly Gly Ser Gly Pro
                165                 170                 175
Gln Arg Val Ala Ala His Ile Thr Gly Thr Arg Gly Arg Ser Asn Thr
            180                 185                 190
Leu Ser Ser Pro Asn Ser Lys Asn Glu Lys Ala Leu Gly Arg Lys Ile
        195                 200                 205
Asn Ser Trp Glu Ser Ser Arg Ser Gly His Ser Phe Leu Ser Asn Leu
210                 215                 220
His Leu Arg Asn Gly Glu Leu Val Ile His Glu Lys Gly Phe Tyr Tyr
225                 230                 235                 240
Ile Tyr Ser Gln Thr Tyr Phe Arg Phe Gln Glu Glu Ile Lys Glu Val
                245                 250                 255
Thr Arg Asn Asp Lys Gln Met Val Gln Tyr Ile Tyr Lys Trp Thr Asp
            260                 265                 270
Tyr Pro Asp Pro Ile Leu Leu Met Lys Ser Ala Arg Asn Ser Cys Trp
        275                 280                 285
Ser Lys Asp Ala Glu Tyr Gly Leu Tyr Ser Ile Tyr Gln Gly Gly Ile
    290                 295                 300
Phe Glu Leu Lys Glu Asn Asp Arg Ile Phe Val Ser Val Thr Asn Glu
305                 310                 315                 320
His Leu Ile Asp Met His His Glu Ala Ser Phe Phe Gly Ala Phe Leu
                325                 330                 335
Val Gly Gly Gly Ser Gly Gly Gly Ser Gly Gly Gly Ser Gly Pro Gln
            340                 345                 350
Arg Val Ala Ala His Ile Thr Gly Thr Arg Gly Arg Ser Asn Thr Leu
        355                 360                 365
Ser Ser Pro Asn Ser Lys Asn Glu Lys Ala Leu Gly Arg Lys Ile Asn
    370                 375                 380
Ser Trp Glu Ser Ser Arg Ser Gly His Ser Phe Leu Ser Asn Leu His
385                 390                 395                 400
Leu Arg Asn Gly Glu Leu Val Ile His Glu Lys Gly Phe Tyr Tyr Ile
                405                 410                 415
Tyr Ser Gln Thr Ala Phe Arg Phe Ser Glu Glu Ile Lys Glu Val Thr
            420                 425                 430
Arg Asn Asp Lys Gln Met Val Gln Tyr Ile Tyr Lys Trp Thr Asp Tyr
        435                 440                 445
Pro Asp Pro Ile Leu Leu Met Lys Ser Ala Arg Asn Ser Cys Trp Ser
    450                 455                 460
Lys Asp Ala Glu Tyr Gly Leu Tyr Ser Ile Tyr Gln Gly Gly Ile Phe
465                 470                 475                 480
Glu Leu Lys Glu Asn Asp Arg Ile Phe Val Ser Val Thr Asn Glu His
                485                 490                 495
Leu Ile Asp Met Asp His Glu Ala Ser Phe Phe Gly Ala Phe Leu Val
            500                 505                 510
Gly

<210> SEQ ID NO 25
<211> LENGTH: 28
<212> TYPE: PRT
<213> ORGANISM: Artificial
```

```
<220> FEATURE:
<223> OTHER INFORMATION: synthetic

<400> SEQUENCE: 25

Met Gly Ile Leu Pro Ser Pro Gly Met Pro Ala Leu Leu Ser Leu Val
1               5                   10                  15
Ser Leu Leu Ser Val Leu Leu Met Gly Cys Val Ala
            20                  25

<210> SEQ ID NO 26
<211> LENGTH: 17
<212> TYPE: PRT
<213> ORGANISM: Artificial
<220> FEATURE:
<223> OTHER INFORMATION: synthetic

<400> SEQUENCE: 26

Ser Ser Gly Arg Glu Asn Leu Tyr Phe Gln Gly His His His His His
1               5                   10                  15
His

<210> SEQ ID NO 27
<211> LENGTH: 10
<212> TYPE: PRT
<213> ORGANISM: Artificial
<220> FEATURE:
<223> OTHER INFORMATION: synthetic

<400> SEQUENCE: 27

Ser Ser Gly Arg Glu Asn Leu Tyr Phe Gln
1               5                   10

<210> SEQ ID NO 28
<211> LENGTH: 22
<212> TYPE: DNA
<213> ORGANISM: Artificial
<220> FEATURE:
<223> OTHER INFORMATION: synthetic

<400> SEQUENCE: 28
atgtgggtgt tcaagtttct gc                                      22

<210> SEQ ID NO 29
<211> LENGTH: 20
<212> TYPE: DNA
<213> ORGANISM: Artificial
<220> FEATURE:
<223> OTHER INFORMATION: synthetic

<400> SEQUENCE: 29
ccacaagatt ctggggactc                                         20

<210> SEQ ID NO 30
<211> LENGTH: 20
<212> TYPE: DNA
<213> ORGANISM: Artificial
<220> FEATURE:
<223> OTHER INFORMATION: synthetic

<400> SEQUENCE: 30
cccgtcacat tctggtccat                                         20

<210> SEQ ID NO 31
<211> LENGTH: 23
<212> TYPE: DNA
```

```
<213> ORGANISM: Artificial
<220> FEATURE:
<223> OTHER INFORMATION: synthetic

<400> SEQUENCE: 31
caagtaaccg tgtagctgca caa                                           23

<210> SEQ ID NO 32
<211> LENGTH: 24
<212> TYPE: DNA
<213> ORGANISM: Artificial
<220> FEATURE:
<223> OTHER INFORMATION: synthetic

<400> SEQUENCE: 32
cagctcccta gaagatggat tcat                                          24

<210> SEQ ID NO 33
<211> LENGTH: 21
<212> TYPE: DNA
<213> ORGANISM: Artificial
<220> FEATURE:
<223> OTHER INFORMATION: synthetic

<400> SEQUENCE: 33
gtcaggagtg ggagccatat g                                             21

<210> SEQ ID NO 34
<211> LENGTH: 21
<212> TYPE: DNA
<213> ORGANISM: Artificial
<220> FEATURE:
<223> OTHER INFORMATION: synthetic

<400> SEQUENCE: 34
ttcgactacg gccagatgat t                                             21

<210> SEQ ID NO 35
<211> LENGTH: 23
<212> TYPE: DNA
<213> ORGANISM: Artificial
<220> FEATURE:
<223> OTHER INFORMATION: synthetic

<400> SEQUENCE: 35
ggagaaagac aggtccatca agt                                           23

<210> SEQ ID NO 36
<211> LENGTH: 20
<212> TYPE: DNA
<213> ORGANISM: Artificial
<220> FEATURE:
<223> OTHER INFORMATION: synthetic

<400> SEQUENCE: 36
agcatacagg tcctggcatc                                               20

<210> SEQ ID NO 37
<211> LENGTH: 20
<212> TYPE: DNA
<213> ORGANISM: Artificial
<220> FEATURE:
<223> OTHER INFORMATION: synthetic

<400> SEQUENCE: 37
ttcaccttcc caaagaccac                                               20
```

<210> SEQ ID NO 38
<211> LENGTH: 4
<212> TYPE: PRT
<213> ORGANISM: Artificial
<220> FEATURE:
<223> OTHER INFORMATION: synthetic

<400> SEQUENCE: 38

Gly Gly Ser Gly
1

<210> SEQ ID NO 39
<211> LENGTH: 4
<212> TYPE: PRT
<213> ORGANISM: Artificial
<220> FEATURE:
<223> OTHER INFORMATION: synthetic

<400> SEQUENCE: 39

Gly Gly Gly Ser
1

<210> SEQ ID NO 40
<211> LENGTH: 5
<212> TYPE: PRT
<213> ORGANISM: Artificial
<220> FEATURE:
<223> OTHER INFORMATION: synthetic

<400> SEQUENCE: 40

Gly Gly Gly Gly Ser
1               5

<210> SEQ ID NO 41
<211> LENGTH: 4
<212> TYPE: PRT
<213> ORGANISM: Artificial
<220> FEATURE:
<223> OTHER INFORMATION: synthetic

<400> SEQUENCE: 41

Gly Ser Ala Thr
1

<210> SEQ ID NO 42
<211> LENGTH: 513
<212> TYPE: PRT
<213> ORGANISM: Artificial
<220> FEATURE:
<223> OTHER INFORMATION: synthetic

<400> SEQUENCE: 42

Pro Gln Arg Val Ala Ala His Ile Thr Gly Thr Arg Gly Arg Ser Asn
1               5                   10                  15

Thr Leu Ser Ser Pro Asn Ser Lys Asn Glu Lys Ala Leu Gly Arg Lys
            20                  25                  30

Ile Asn Ser Trp Glu Ser Ser Arg Ser Gly His Ser Phe Leu Ser Asn
        35                  40                  45

Leu His Leu Arg Asn Gly Glu Leu Val Ile His Glu Lys Gly Phe Tyr
    50                  55                  60

Tyr Ile Tyr Ser Gln Thr Asn Phe Lys Phe Arg Glu Glu Ile Lys Glu
65                  70                  75                  80

Arg Thr His Asn Asp Lys Gln Met Val Gln Tyr Ile Tyr Lys Tyr Thr

-continued

```
                85                  90                  95
Asp Tyr Pro Asp Pro Ile Leu Leu Met Lys Ser Ala Arg Asn Ser Cys
            100                 105                 110

Trp Ser Lys Asp Ala Glu Tyr Gly Leu Tyr Ser Ile Tyr Gln Gly Gly
            115                 120                 125

Ile Phe Glu Leu Lys Glu Asn Asp Arg Ile Phe Val Ser Val Thr Asn
            130                 135                 140

Glu Arg Leu Leu Gln Met Asp His Glu Ala Ser Phe Phe Gly Ala Phe
145                 150                 155                 160

Leu Val Gly Gly Gly Ser Gly Gly Gly Ser Gly Gly Gly Ser Gly Pro
                165                 170                 175

Gln Arg Val Ala Ala His Ile Thr Gly Thr Arg Arg Arg Ser Asn Thr
            180                 185                 190

Leu Ser Ser Pro Asn Ser Lys Asn Glu Lys Ala Leu Gly Arg Lys Ile
            195                 200                 205

Asn Ser Trp Glu Ser Ser Arg Arg Gly His Ser Phe Leu Ser Asn Leu
            210                 215                 220

His Leu Arg Asn Gly Glu Leu Val Ile His Glu Lys Gly Phe Tyr Tyr
225                 230                 235                 240

Ile Tyr Ser Gln Thr Tyr Phe Arg Phe Gln Glu Ile Lys Glu Arg
            245                 250                 255

Thr His Asn Asp Lys Gln Met Val Gln Tyr Ile Tyr Lys Tyr Thr Asp
            260                 265                 270

Tyr Pro Asp Pro Ile Leu Leu Met Lys Ser Ala Arg Asn Ser Cys Trp
            275                 280                 285

Ser Lys Asp Ala Glu Tyr Gly Leu Tyr Ser Ile Tyr Gln Gly Gly Ile
            290                 295                 300

Phe Glu Leu Lys Glu Asn Asp Arg Ile Phe Val Ser Val Thr Asn Glu
305                 310                 315                 320

His Leu Ile Asp Met Asp His Glu Ala Ser Phe Phe Gly Ala Phe Leu
                325                 330                 335

Val Gly Gly Gly Ser Gly Gly Gly Ser Gly Gly Gly Ser Gly Pro Gln
            340                 345                 350

Arg Val Ala Ala His Ile Thr Gly Thr Arg Arg Arg Ser Asn Thr Leu
            355                 360                 365

Ser Ser Pro Asn Ser Lys Asn Glu Lys Ala Leu Gly Arg Lys Ile Asn
            370                 375                 380

Ser Trp Glu Ser Ser Arg Arg Gly His Ser Phe Leu Ser Asn Leu His
385                 390                 395                 400

Leu Arg Asn Gly Glu Leu Val Ile His Glu Lys Gly Phe Tyr Tyr Ile
                405                 410                 415

Tyr Ser Gln Thr Tyr Phe Arg Phe Gln Glu Ile Lys Glu Asn Thr
            420                 425                 430

Lys Asn Asp Lys Gln Met Val Gln Tyr Ile Tyr Lys Tyr Thr Ser Tyr
            435                 440                 445

Pro Asp Pro Ile Leu Leu Met Lys Ser Ala Arg Asn Ser Cys Trp Ser
            450                 455                 460

Lys Asp Ala Glu Tyr Gly Leu Tyr Ser Ile Tyr Gln Gly Gly Ile Phe
465                 470                 475                 480

Glu Leu Lys Glu Asn Asp Arg Ile Phe Val Ser Val Thr Asn Glu His
                485                 490                 495

Leu Ile Asp Met Asp His Glu Ala Ser Phe Phe Gly Ala Phe Leu Val
                500                 505                 510
```

Gly

<210> SEQ ID NO 43
<211> LENGTH: 509
<212> TYPE: PRT
<213> ORGANISM: Artificial
<220> FEATURE:
<223> OTHER INFORMATION: synthetic

<400> SEQUENCE: 43

```
Gln Arg Val Ala Ala His Ile Thr Gly Thr Arg Gly Arg Ser Asn Thr
1               5                   10                  15

Leu Ser Ser Pro Asn Ser Lys Asn Glu Lys Ala Leu Gly Arg Lys Ile
                20                  25                  30

Asn Ser Trp Glu Ser Ser Arg Ser Gly His Ser Phe Leu Ser Asn Leu
            35                  40                  45

His Leu Arg Asn Gly Glu Leu Val Ile His Glu Lys Gly Phe Tyr Tyr
        50                  55                  60

Ile Tyr Ser Gln Thr Asn Phe Lys Phe Arg Glu Glu Ile Lys Glu Arg
65                  70                  75                  80

Thr His Asn Asp Lys Gln Met Val Gln Tyr Ile Tyr Lys Tyr Thr Asp
                85                  90                  95

Tyr Pro Asp Pro Ile Leu Leu Met Lys Ser Ala Arg Asn Ser Cys Trp
            100                 105                 110

Ser Lys Asp Ala Glu Tyr Gly Leu Tyr Ser Ile Tyr Gln Gly Gly Ile
        115                 120                 125

Phe Glu Leu Lys Glu Asn Asp Arg Ile Phe Val Ser Val Thr Asn Glu
    130                 135                 140

Arg Leu Leu Gln Met Asp His Glu Ala Ser Phe Phe Gly Ala Phe Leu
145                 150                 155                 160

Val Gly Gly Gly Ser Gly Gly Ser Gly Gly Ser Gly Gln Arg
                165                 170                 175

Val Ala Ala His Ile Thr Gly Thr Arg Arg Arg Ser Asn Thr Leu Ser
                180                 185                 190

Ser Pro Asn Ser Lys Asn Glu Lys Ala Leu Gly Arg Lys Ile Asn Ser
            195                 200                 205

Trp Glu Ser Ser Arg Arg Gly His Ser Phe Leu Ser Asn Leu His Leu
210                 215                 220

Arg Asn Gly Glu Leu Val Ile His Glu Lys Gly Phe Tyr Tyr Ile Tyr
225                 230                 235                 240

Ser Gln Thr Tyr Phe Arg Phe Gln Glu Glu Ile Lys Glu Asn Thr Lys
                245                 250                 255

Asn Asp Lys Gln Met Val Gln Tyr Ile Tyr Lys Tyr Thr Ser Tyr Pro
            260                 265                 270

Asp Pro Ile Leu Leu Met Lys Ser Ala Arg Asn Ser Cys Trp Ser Lys
        275                 280                 285

Asp Ala Glu Tyr Gly Leu Tyr Ser Ile Tyr Gln Gly Gly Ile Phe Glu
    290                 295                 300

Leu Lys Glu Asn Asp Arg Ile Phe Val Ser Val Thr Asn Glu His Leu
305                 310                 315                 320

Ile Asp Met Asp His Glu Ala Ser Phe Phe Gly Ala Phe Leu Val Gly
                325                 330                 335

Gly Gly Ser Gly Gly Gly Ser Gly Gly Gly Ser Gly Gln Arg Val Ala
            340                 345                 350
```

-continued

```
Ala His Ile Thr Gly Thr Arg Gly Arg Ser Asn Thr Leu Ser Ser Pro
        355                 360                 365

Asn Ser Lys Asn Glu Lys Ala Leu Gly Arg Lys Ile Asn Ser Trp Glu
    370                 375                 380

Ser Ser Arg Ser Gly His Ser Phe Leu Ser Asn Leu His Leu Arg Asn
385                 390                 395                 400

Gly Glu Leu Val Ile His Glu Lys Gly Phe Tyr Tyr Ile Tyr Ser Gln
                405                 410                 415

Thr Asn Phe Lys Phe Arg Glu Glu Ile Lys Glu Asn Thr Lys Asn Asp
            420                 425                 430

Lys Gln Met Val Gln Tyr Ile Tyr Lys Tyr Thr Ser Tyr Pro Asp Pro
        435                 440                 445

Ile Leu Leu Met Lys Ser Ala Arg Asn Ser Cys Trp Ser Lys Asp Ala
    450                 455                 460

Glu Tyr Gly Leu Tyr Ser Ile Tyr Gln Gly Gly Ile Phe Glu Leu Lys
465                 470                 475                 480

Glu Asn Asp Arg Ile Phe Val Ser Val Thr Glu Arg Leu Leu Gln Met
                485                 490                 495

Asp His Glu Ala Ser Phe Phe Gly Ala Phe Leu Val Gly
            500                 505

<210> SEQ ID NO 44
<211> LENGTH: 9
<212> TYPE: PRT
<213> ORGANISM: Artificial
<220> FEATURE:
<223> OTHER INFORMATION: synthetic

<400> SEQUENCE: 44

Phe Arg Gly Gly Ser His His Glu Thr
1               5
```

MUTANT TUMOR NECROSIS FACTOR RECEPTOR SUPERFAMILY (TNFSFR) LIGANDS AND METHODS OF MAKING AND USING SAME

CROSS-REFERENCE TO RELATED APPLICATIONS

This is a continuation of Ser. No. 15/894,502 filed 12 Feb. 2018, which is a continuation of Ser. No. 14/796,827, now U.S. Pat. No. 9,914,761, filed 10 Jul. 2015, which claims the benefit of U.S. Provisional patent application Ser. No. 62/023,117, filed 10 Jul. 2014. Each of the above references is incorporated herein by reference in its entirety.

STATEMENT REGARDING FEDERALLY-SPONSORED RESEARCH AND DEVELOPMENT

This invention was made with government support under AR032788 and AG039896 awarded by the National Institutes of Health. The government has certain rights in the invention.

REFERENCE TO SEQUENCE LISTING SUBMITTED ELECTRONICALLY

The content of the electronically submitted sequence listing in ASCII text file (Name53047.144425_SEQ LISTING_ST25.txt; Size: 102,715 bytes (MS-DOS); and Date of Creation: Jul. 10, 2015) filed with the application is incorporated herein by reference in its entirety.

BACKGROUND

Excess activation of TNF superfamily (TNFsf) receptors can induce a myriad of pathological conditions (1, 2). While some biological agents have positively impacted the course of these diseases, each carries substantial complications (3). The TNFsf member RANKL is a cytokine that regulates osteoclast formation and function (4-7) and excess activation of its receptor, RANK, can promote many if not most forms of pathological bone loss. RANKL exists as a homotrimer in solution (8). Each of the three interfaces separating the monomers contains a binding groove accepting a single copy of RANK or the anti-osteoclastogenic decoy receptor, osteoprotegerin (OPG) (9-11). As each trimer assembles, loops and strands at the edges of apposed monomers combine to form the sides of the receptor-binding clefts. It is the shape of the binding clefts which determine receptor selectivity. For wild-type RANKL, each of the three identical receptor-binding clefts, spaced equally around the outside of the cytokine, can accept a single copy of RANK or the anti-osteoclastogenic decoy receptor, osteoprotegerin (OPG)

RANKL, a member of the TNF superfamily, binds to multiple receptors (RANK and OPG) with different biological effects. Within this superfamily, there are several examples of cytokines demonstrating receptor promiscuity (17). For example, TNFα, which recognizes TNFR1 and TNFR2, is central to the pathogenesis of disabling disorders such as rheumatoid arthritis and psoriasis (18). Treatment of these diseases has been greatly facilitated by global TNFα blockade using humanized antibodies or soluble receptor (19, 20). As effective as these drugs are, they carry major complications such as predisposition to malignancy and serious infections, including tuberculosis (21, 22). Current evidence indicates that the positive effects of anti-TNFα therapy reflects suppressed activation of TNFR1, while negative consequences are due to inhibition of the pro-immune properties of TNFR2 (23, 24). For example, the osteolysis responsible for orthopedic implant loosening appears to be solely mediated by TNFR1 (Merkel et al., 1999; Am. Journ. Pathol. 154(1):203-210). In fact activation of TNFR1 promotes osteoclastogenesis, leading to bond resorption, while activation of TNFR2 inhibits it. Further, TNFR1 activation inhibits pre-osteoblast differentiation, and so blunts bone formation, while activation of TNFR2 does not (Abbas et al., 2003; Cytokine 22(1-2): 33-41. Thus TNFR2 signaling inhibits bone remodeling, but not bone formation, and so displays protective properties in the context of inflammatory osteolysis. Nago et al, 2011, J. Bone Miner. Metab; 29(6): 671-681. and Hussain et al., 2008, J. Bone Miner. Metab; 26(5):p 469-477). The need for DR4 vs. DR5 specific TRAIL variants stems from the apparent DR4- or DR5-specific sensitivities of various tumors to selective receptor agonists. For example, acute myeloid leukemia appears to be more sensitive to a DR4-selective variant yet resistant to killing by a DR5-selective TRAIL variant (Szegezdi, Journal of Cellular and Molecular Medicine Volume 15, Issue 10, pages 2216-2231, October 2011). Additionally, it has been reported using several different chronic lymphocytic leukemia cell lines that an agonist antibody specific for DR4 induce apoptosis whereas an agonist antibody specific for DR5 fails to do so (Xiao, Leukemia and Lymphoma July 2011, Vol. 52, No. 7, Pages 1290-1301). Conversely, DR5-selective TRAIL variant was effective in killing a breast cancer cell line whereas a DR4-selective TRAIL variant was not despite similar expression of DR4 and DR5 in these cells (Kelley 2005 The Journal of Biological Chemistry, 280, 2205-2212). The sensitivity of various cancer types including primary cells and cell lines is reviewed extensively in van Roosmalen et al. (van Roosmalen Biochemical Pharmacology, Volume 91, Issue 4, 15 Oct. 2014, Pages 447-456). RANKL, TNF, and TRAIL interact with their receptors in a homologous fashion (9, 10, 25, 26).

"Novel variants of RANKL protein" WO2003059281 (PCT/US2003/000393) of Desjarlais, J. R., et al., and TNF Family Ligand Variants" US20140096274 A1 of Quax, W. J., et al. discuss RANKL variants. "Single-chain antagonist polypeptides" WO2001025277 of Andersen, K. V., et al. discusses modification of osteoprotegerin ligand. The articles "Crystal structure of the TRANCE/RANKL cytokine reveals determinants of receptor-ligand specificity" of Lam, J., Nelson, C. A., Ross, F. P., Teitelbaum, S. L., Fremont, D. H; J Clin Invest. 2001 October; 108(7):971-9 and "Structural and functional insights of RANKL-RANK interaction and signaling" of Liu, C., et al., J Immunol. 2010 Jun. 15; 184(12):6910-9 discuss structural features of RANKL.

The sole medically approved inhibitor of this pathway, denosumab, targets the cytokine itself but not its receptor and its effects last for 7-9 months (12). Given the profound suppression of bone remodeling accompanying cytokine removal or other anti-bone resorptive strategies, shorter acting agents are needed.

SUMMARY

The present inventors herein report a strategy for generating an effective inhibitor of RANK signaling and other members of the TNFsf. The inventors of the present teachings have developed RANKL variants that can inhibit RANK signaling. In various embodiments, a single chain RANK ligand of the present teachings can be an inhibitor of bone resorption. In various embodiments, a polypeptide of the present teachings can comprise or consist of three monomers of RANK ligand. In various embodiments, a RANK ligand trimer can comprise a combination of mutations which can recognize RANK ligand with high avidity but can fail to recognize osteoprotegrin. In some embodiments, a polypeptide of the present teachings can inhibit bone resorption in vivo, and can be used to treat or prevent bone loss diseases such as osteoporosis in a human or other mammalian subject. In some embodiments, a polypeptide of the present teachings can inhibit bone resorption in vitro.

In various embodiments, a single-chain RANKL, with a combination of blocked or high affinity RANK binding sites as disclosed herein, can arrest RANK signaling, and can thus function as an effective inhibitor of RANKL-mediated osteoclast formation and function.

In various embodiments, a RANKL polypeptide of the present teachings can combine high affinity and blocking mutations into a single-chain, and can serve as an effective inhibitor that can be receptor selective. In various configurations, this can provide a mechanism for blocking TNFR1 while sparing TNFR2, thereby reducing systemic complications. This strategy can be broadly applicable to all members of the pathologically relevant TNF superfamily.

Methods for constructing an inhibitor of a Tumor Necrosis Factor superfamily (TNFsf) member receptor comprising the step of combining in a single polypeptide chain: (i) at least one first mutated TNFsf monomer that comprises at least one first mutation that blocks binding of a TNFsf member comprising the first mutated monomer to its corresponding target Tumor Necrosis Factor superfamily receptor; and, (ii) at least one second mutated TNFsf monomer that comprises at least one second mutation that increases binding affinity of a TNFsf member comprising the second mutated monomer to the corresponding target Tumor Necrosis Factor superfamily receptor, wherein at least three mutated TNFsf monomers are combined in the single polypeptide chain are provided. Methods for constructing an inhibitor of a Tumor Necrosis Factor superfamily (TNFsf) member receptor comprising the step of combining in a single polypeptide chain: (i) at least one first mutated TNFsf monomer that comprises at least one first mutation that blocks binding of a TNFsf member comprising the first mutated monomer to its corresponding target Tumor Necrosis Factor superfamily receptor; and, (ii) at least one second mutated TNFsf monomer that comprises at least one second mutation that increases binding affinity of a TNFsf member comprising the second mutated monomer to the corresponding target Tumor Necrosis Factor superfamily receptor, wherein at least two mutated TNFsf monomers and a wild type TNFsf monomer are combined in the single polypeptide chain are also provided. In certain embodiments, the single polypeptide chain comprises: (i) two first mutated TNFsf monomers and one second mutated TNFsf monomer; or (ii) one first mutated TNFsf monomer and two second mutated TNFsf monomers. In certain embodiments of the aforementioned methods, (i) one, two, or three of the monomers comprise at least one third mutation that decreases binding affinity of a TNFsf member comprising the three monomers with the third mutation to a non-target Tumor Necrosis Factor superfamily receptor; (ii) the second mutation(s) is a bifunctional mutation that both increases binding affinity of a TNFsf member comprising or consisting of the second mutated monomer to the corresponding target Tumor Necrosis Factor superfamily receptor and decreases binding affinity of a TNFsf member comprising or consisting of the second mutated monomer to a non-target Tumor Necrosis Factor superfamily receptor; (iii) the first mutation is a bifunctional mutation that both blocks binding of a TNFsf member comprising or consisting of the first mutated monomer to its corresponding target Tumor Necrosis Factor superfamily receptor and decreases binding affinity of a TNFsf member comprising or consisting of the first mutated monomer to a non-target Tumor Necrosis Factor superfamily receptor; or (iv) the single chain polypeptide comprises any combination of (i), (ii), and (iii). In certain embodiments of the aforementioned methods, the first mutation is selected from the group consisting of an AA"-Loop mutation, a BC loop mutation, a mutation in the C-terminal half of strand C, a CD-Loop mutation, a mutation in the N-terminal half of strand D, a DE Loop mutation, a mutation in the E strand, an EF loop mutation, a mutation in the N-terminal half of strand D, a mutation in the DE loop, an FG loop mutation, a GH-loop mutation, a salt-bridge-disrupting mutation, and combinations thereof, and wherein the mutation comprises an insertion, a deletion, a substitution, or a combination thereof. In certain embodiments of the aforementioned methods, the TNFsf member is human Receptor Activator of Nuclear Factor κ B Ligand (RANKL), the target Tumor Necrosis Factor superfamily receptor is Receptor Activator of Nuclear Factor κ B (RANK), and the non-target Tumor Necrosis Factor superfamily receptor is Osteoprotegerin (OPG). In certain embodiments of the aforementioned method where the TNFsf is RANKL, the first mutation is selected from the group consisting of a substitution of AA" loop residues 177-185, R223Q, R223A, R223Y, an insertion immediately C-terminal to R223, H225N, I249R, and combinations thereof; and wherein the second mutation or bifunctional mutation is selected from the group consisting of A172R, K195E, F270Y, H271Y, Q237H, Q237T, and combinations thereof. In certain embodiments of the aforementioned methods where the TNFsf member is human RANKL, the third mutation or the bifunctional mutation is selected from the group consisting of G192A, K195E, F270Y, H271Y, Q237H, Q237T, and combinations thereof. In certain embodiments of the aforementioned methods, the TNFsf member is human Tumor Necrosis Factor (TNF), the target Tumor Necrosis Factor superfamily receptor is Tumor Necrosis Factor Receptor 1 (TNFR1), and the non-target Tumor Necrosis Factor superfamily receptor is Tumor Necrosis Factor Receptor 2 (TNFR2). In certain embodiments of the aforementioned methods where the TNFsf member is human Tumor Necrosis Factor (TNF), the first mutation or bifunctional mutation is selected from the group consisting of N110Q, L151R, Y163Q, Y163G, Y163L, Y163K, Y163T, S175Y, D219V, and combinations thereof. In certain embodiments of the aforementioned methods where the TNFsf member is human Tumor Necrosis Factor (TNF), the second mutation or bifunctional mutation is selected from the group consisting of L105T, R108F, A160T, V161T, S162A, Q164S, V161S, S162V, S162T, Q164P, T165H, E222T, and T165G and combinations thereof. In certain embodiments of the aforementioned methods where the TNFsf member is human Tumor Necrosis Factor (TNF), the third mutation or bifunctional mutation is selected from the group consisting of L105T, R108F, L151R, A160T, V161T, S162A, S162T, Q164S, T165G, S175Y, E222T, and combinations thereof. In certain embodiments of the aforementioned methods where the TNFsf member is human Tumor Necrosis Factor (TNF), the first mutation or bifunctional mutation is selected from the group consisting of N110Q, L151R, Y163Q, Y163G, Y163L, Y163K, Y163T, S175Y, D219V, and combinations thereof; wherein the second mutation or bifunctional mutation is selected from the group consisting of L105T, R108F, A160T, V161T, S162A, Q164S, V161S, S162V, S162T, Q164P, T165H, E222T, and T165G and combinations thereof; and wherein the third mutation or bifunctional mutation is selected from the group consisting of L105T, R108F, L151R, A160T, V161T, S162A, S162T, Q164S, T165G, S175Y, E222T, and combinations thereof. In certain embodiments of the aforementioned methods, the TNFsf member is TNF-related apoptosis-inducing ligand (TRAIL), the target TNFsf receptor is DR5, and the non-target Tumor Necrosis Factor superfamily receptor is DR4, DcR1, DcR2, and OPG. In certain embodiments of the aforementioned methods where the TNFsf member is TNF-related apoptosis-inducing ligand (TRAIL), the first, second, third, or bifunctional mutations are selected from the TRAIL mutations disclosed in Table 4. In certain embodiments of the aforementioned methods, the TNFsf member is A proliferation inducing ligand (APRIL), the target TNFsf receptor is cyclophilin ligand interactor (TACI), and the non-target Tumor Necrosis Factor superfamily receptor is B cell maturation antigen (BCMA). In certain embodiments of the aforementioned methods where the TNFsf member is APRIL, the first, second, third, or bifunctional mutations are selected from the APRIL mutations disclosed in Table 4. In certain embodiments of the aforementioned methods, the method further comprises an initial step of first obtaining the first mutated TNFsf monomer having the at least one first mutation. In certain embodiments of the aforementioned methods, the obtaining step comprises screening a population of mutagenized TNFsf monomers for at least one first mutation that blocks binding of the TNFsf member consisting of the first mutated monomer to its corresponding target Tumor Necrosis Factor superfamily receptor. In certain embodiments of the aforementioned methods, the method further comprises: (i) obtaining the second mutated TNFsf monomer having the at least one second mutation; or (ii) obtaining a mutated TNFsf monomer comprising the third mutation, or the combination thereof. In certain embodiments of the aforementioned methods, the obtaining step comprises screening a population of mutagenized TNFsf monomers for at least one second mutation or for at least one bifunctional mutation that increases binding affinity of a TNFsf member comprising the second mutated monomer to the corresponding target Tumor Necrosis Factor superfamily receptor. In certain embodiments of the aforementioned methods, the screening comprises detection of binding to limiting amounts of the target TNFsf receptor in the presence of a non-target receptor. In certain embodiments of the aforementioned methods, the obtaining step comprises screening a population of mutagenized TNFsf monomers for at least one third mutation or at least one bifunctional mutation that decreases binding affinity of a TNFsf member comprising monomers with the third mutation to a non-target Tumor Necrosis Factor superfamily receptor. In certain embodiments of the aforementioned methods, iterative selections are used to obtain additional second mutations or bifunctional mutations that increase binding affinity of the TNFsf member comprising the second mutated monomer to the corresponding target Tumor Necrosis Factor superfamily receptor. In certain embodiments of the aforementioned methods, iterative selections are used to obtain third mutations or bifunctional mutations that decrease binding affinity of a TNFsf member comprising the second mutated monomer to a non-target Tumor Necrosis Factor superfamily receptor. In certain embodiments of the aforementioned methods, bifunctional mutations that increase binding affinity to the corresponding target TNFsf receptor while decreasing binding affinity to the corresponding non-target TNFsf receptor are used. In certain embodiments of the aforementioned methods, other bifunctional mutations that reduce or essentially eliminate binding to both the corresponding target TNFsf receptor and the corresponding non-target TNFsf receptor are used. In certain embodiments of the aforementioned methods, the combining step comprises: (i) constructing a recombinant nucleic acid comprising a nucleic acid sequence encoding the first and second mutated monomers, wherein the monomers are operably linked in the encoded single chain polypeptide and wherein the nucleic acid that encodes the single chain polypeptide is operably linked to a promoter, a nucleic acid encoding a signal peptide, or the combination thereof, (ii) introducing the nucleic acid into a cell; and, (iii) harvesting the encoded single chain polypeptide from a cell that comprises the recombinant nucleic acid and expresses the single chain polypeptide or from media in which the cell was grown. In certain embodiments of the aforementioned methods, the monomers are operably linked in the single chain polypeptide with a peptide linker. In certain embodiments of the aforementioned methods, the peptide linker comprises a one or more of a glycine rich peptide, Gly-Gly-Ser-Gly (SEQ ID NO: 38), [Gly-Ser]x linkers where x=2-10; Gly-Gly-Gly-Ser (SEQ ID NO: 39), Gly-Gly-Gly-Gly-Ser (SEQ ID NO: 40); Ser-Glu-Gly; Gly-Ser-Ala-Thr" (SEQ ID NO: 41), or any combination thereof. In certain embodiments, the peptide linker is about 4 to about 12 amino acids in length. Inhibitors of a Tumor Necrosis Factor superfamily (TNFsf) member receptor that are made by any of the aforementioned methods are also provided herein.

Recombinant single chain polypeptides comprising: (i) at least one mutated TNFsf monomer comprising at least one first mutation that blocks binding of a TNFsf member comprising the first mutated monomer to a corresponding target Tumor Necrosis Factor superfamily receptor; and, (ii) a second mutated TNFsf monomer comprising at least one second mutation that increases binding affinity of a TNFsf member comprising the second mutated monomer to the corresponding target Tumor Necrosis Factor superfamily receptor, wherein a total of at least three mutated TNFsf monomers are operably linked in the recombinant single chain polypeptide and wherein the recombinant single chain polypeptide is an inhibitor of the target Tumor Necrosis Factor superfamily (TNFsf) member receptor are provided herein. Recombinant single chain polypeptides comprising: (i) at least one mutated TNFsf monomer comprising at least one first mutation that blocks binding of a TNFsf member comprising the first mutated monomer to a corresponding target Tumor Necrosis Factor superfamily receptor; and, (ii) a second mutated TNFsf monomer comprising at least one second mutation that increases binding affinity of a TNFsf member comprising the second mutated monomer to the corresponding target Tumor Necrosis Factor superfamily receptor, wherein a total of at least two mutated TNFsf monomers and a wild-type monomer are operably linked in the recombinant single chain polypeptide, and wherein the recombinant single chain polypeptide is an inhibitor of the target Tumor Necrosis Factor superfamily (TNFsf) member receptor are also provided herein. In certain embodiments, (i) the single chain polypeptide further comprises at least one third mutation in one, two, or three of the monomers that decreases binding affinity of a TNFsf member comprising the monomers with the third mutation to a non-target Tumor Necrosis Factor superfamily receptor; (ii) the second mutation(s) is a bifunctional mutation that both increases binding affinity of a TNFsf member comprising or consisting of the second mutated monomer to the corresponding target Tumor Necrosis Factor superfamily receptor and decreases binding affinity of a TNFsf member comprising or consisting of the second mutated monomer to a non-target Tumor Necrosis Factor superfamily receptor; (iii) the first mutation is a bifunctional mutation that both blocks binding of a TNFsf member comprising or consisting of the first mutated monomer to its corresponding target Tumor Necrosis Factor superfamily receptor and decreases binding affinity of a TNFsf member comprising or consisting of the first mutated monomer to a non-target Tumor Necrosis Factor superfamily receptor; or (iv) the single chain polypeptide comprises any combination of (i), (ii), and (iii). In certain embodiments of any of the aforementioned single chain polypeptides, the single polypeptide chain comprises: (i) two first mutated TNFsf monomers and one second mutated TNFsf monomer; or (ii) the single polypeptide chain comprises one first mutated TNFsf monomer and two second mutated TNFsf monomers. In certain embodiments, bifunctional mutations that increase binding affinity to the corresponding target TNFsf receptor while decreasing binding affinity to the corresponding non-target TNFsf receptor are used. In certain embodiments, other bifunctional mutations that reduce or essentially eliminate binding to both the corresponding target TNFsf receptor and the corresponding non-target TNFsf receptor are used. In certain embodiments of any of the aforementioned single chain polypeptides, the first mutation is selected from the group consisting of an AA"-Loop mutation, a BC loop mutation, a mutation in the C-terminal half of strand C, a CD-Loop mutation, a mutation in the N-terminal half of strand D, a DE Loop mutation, a mutation in the E strand, an EF loop mutation, a mutation in the N-terminal half of strand D, a mutation in the DE loop, an FG loop mutation, a GH-loop mutation, a salt-bridge-disrupting mutation, and combinations thereof, wherein the mutation comprises an insertion, a deletion, a substitution, or a combination thereof. In certain embodiments of any of the aforementioned single chain polypeptides, the TNFsf member is RANKL, the target Tumor Necrosis Factor superfamily receptor is Receptor Activator of Nuclear Factor κ B (RANK), and the non-target Tumor Necrosis Factor superfamily receptor is Osteoprotegerin (OPG). In certain embodiments of the aforementioned single chain polypeptide, the first mutation is selected from the group consisting of a substitution of AA" loop residues 177-185, R223Q, R223A, R223Y, an insertion immediately C-terminal to R223, H225N, I249R, and combinations thereof; wherein the second mutation or bifunctional mutation is selected from the group consisting of A172R, K195E, F270Y, H271Y, Q237H, Q237T, and combinations thereof; and wherein the third mutation or the bifunctional mutation is selected from the group consisting of G192A, K195E, F270Y, H271Y, Q237H, Q237T, and combinations thereof. In certain embodiments of certain aforementioned single chain polypeptides, the TNFsf member is human Tumor Necrosis Factor (TNF), the target Tumor Necrosis Factor superfamily receptor is Tumor Necrosis Factor Receptor 1 (TNFR1), and the non-target Tumor Necrosis Factor superfamily receptor is Tumor Necrosis Factor Receptor 2 (TNFR2), wherein the first mutation or bifunctional mutation is selected from the group consisting of N110Q, L151R, Y163Q, Y163G, Y163L, Y163K, Y163T, S175Y, D219V, and combinations thereof. In certain embodiments of certain aforementioned single chain polypeptides, the TNFsf member is human Tumor Necrosis Factor (TNF), the target Tumor Necrosis Factor superfamily receptor is Tumor Necrosis Factor Receptor 1 (TNFR1), and the non-target Tumor Necrosis Factor superfamily receptor is Tumor Necrosis Factor Receptor 2 (TNFR2), wherein the second mutation or bifunctional mutation is selected from the group consisting of L105T, R108F, A160T, V161T, S162A, Q164S, V161S, S162V, S162T, Q164P, T165H, E222T, T165G and combinations thereof. In certain embodiments of certain aforementioned single chain polypeptides, the TNFsf member is human Tumor Necrosis Factor (TNF), the target Tumor Necrosis Factor superfamily receptor is Tumor Necrosis Factor Receptor 1 (TNFR1), and the non-target Tumor Necrosis Factor superfamily receptor is Tumor Necrosis Factor Receptor 2 (TNFR2), wherein the third mutation or bifunctional mutation is selected from the group consisting of L105T, R108F, L151R, A160T, V161T, S162A, S162T, Q164S, T165G, S175Y, E222T, and combinations thereof. In certain embodiments of certain aforementioned single chain polypeptides, the TNFsf member is human Tumor Necrosis Factor (TNF), the target Tumor Necrosis Factor superfamily receptor is Tumor Necrosis Factor Receptor 1 (TNFR1), and the non-target Tumor Necrosis Factor superfamily receptor is Tumor Necrosis Factor Receptor 2 (TNFR2), wherein the first mutation or bifunctional mutation is selected from the group consisting of N110Q, L151R, Y163Q, Y163G, Y163L, Y163K, Y163T, S175Y, D219V, and combinations thereof, wherein the second mutation or bifunctional mutation is selected from the group consisting of L105T, R108F, A160T, V161T, S162A, Q164S, V161S, S162V, S162T, Q164P, T165H, E222T, T165G and combinations thereof, and wherein the third mutation or bifunctional mutation is selected from the group consisting of L105T, R108F, L151R, A160T, V161T, S162A, S162T, Q164S, T165G, S175Y, E222T, and combinations thereof. In certain embodiments of certain aforementioned single chain polypeptides, the TNFsf member is human TRAIL, the target Tumor Necrosis Factor superfamily receptor is DR5, and the non-target Tumor Necrosis Factor superfamily receptor is DR4, DcR1, DcR2, and OPG; wherein the first mutation is selected from the group consisting of Y189A, Q193S, N199V, K201R, Y213W, S215D, and combinations thereof; and wherein the second bifunctional mutation is D269H. In certain embodiments of certain aforementioned single chain polypeptides, the TNFsf member is A proliferation inducing ligand (APRIL), the target TNFsf receptor is cyclophilin ligand interactor (TACI), and the non-target Tumor Necrosis Factor superfamily receptor is B cell maturation antigen (BCMA). In certain embodiments of the aforementioned methods where the TNFsf member is APRIL, the first, second, third, or bifunctional mutations are selected from the APRIL mutations disclosed in Table 4. In certain embodiments, the monomers are operably linked in the single chain polypeptide with a peptide linker. In certain embodiments, the peptide linker comprises a one or more of a glycine rich peptide, Gly-Gly-Ser-Gly (SEQ ID NO: 38), [Gly-Ser]x linkers where x=2-10; Gly-Gly-Gly-Ser (SEQ ID NO: 39), Gly-Gly-Gly-Gly-Ser (SEQ ID NO: 40); Ser-Glu-Gly; Gly-Ser-Ala-Thr (SEQ ID NO: 41), or any combination thereof. In certain embodiments, the peptide linker is about 4 to about 12 amino acids in length.

Recombinant nucleic acids that encode any of the aforementioned recombinant single chain polypeptides, wherein the nucleic acid that encodes the single chain polypeptide is operably linked to a promoter, a nucleic acid encoding a signal peptide, or the combination thereof are also provided.

Host cells containing the aforementioned recombinant nucleic acids are also provided.

Methods for producing a recombinant single chain polypeptide inhibitor of a TNFsf member receptor, comprising the steps of: (i) growing a cell; and (ii) harvesting the encoded single chain polypeptide from a cell that comprises the recombinant nucleic acid and expresses the single chain polypeptide or from media in which the cell was grown are provided herein.

Composition comprising any of the aforementioned recombinant single chain polypeptides and a pharmaceutically acceptable excipient are provided herein.

Methods for inhibiting bone resorption and/or osteoclastogenesis in a subject in need thereof, comprising the step of administering to the subject a therapeutically effective amount of the aforementioned composition where the TNFsf member is RANKL are provided herein.

Methods of treating osteoporosis in a subject in need thereof, comprising the step of administering to the subject a therapeutically effective amount of the aforementioned composition where the TNFsf member is RANKL are provided.

Methods of treating rheumatoid arthritis, Crohn's disease, psoriasis, psoriatic arthritis (PsA), ulcerative colitis (UC), ankylosing spondylitis, or inflammatory osteolysis in a subject in need thereof, comprising the step of administering to the subject a therapeutically effective amount of the aforementioned composition where the TNFsf member is TNF are provided herein.

Methods of treating a DR5-positive cancer in a subject in need thereof, comprising the step of administering to the subject a therapeutically effective amount of the aforementioned composition, wherein the TNFsf member is TNF-related apoptosis-inducing ligand (TRAIL), either alone or in combination with exogenously added wild-type TRAIL are provided herein.

Methods of treating SLE rheumatoid arthritis or multiple sclerosis in a subject in need thereof, comprising the step of administering to the subject a therapeutically effective amount of the aforementioned composition, wherein the TNFsf member is A proliferation inducing ligand (APRIL) are provided herein.

The present teachings further include the following non-limiting aspects.

1. A RANKL polypeptide encoding three covalently linked monomers of RANKL.

2. A RANKL polypeptide in accordance with aspect 1, wherein the monomers are linked by glycine-rich linkers.

3. A RANKL polypeptide in accordance with aspect 2, wherein the linkers are each G-G-S-G.

4. A RANKL polypeptide in accordance with claim 1, wherein the RANKL polypeptide is a single polypeptide chain (scRANKL).

5. A RANKL polypeptide in accordance with aspect 1, further comprising at least one solubility mutation.

6. A RANKL polypeptide in accordance with aspect 5, wherein the at least one solubility mutation is selected from the group consisting of C220S, E246I, and a combination thereof.

7. A RANKL polypeptide in accordance with aspect 4, further comprising at least one sequence inserted into at least one RANKL loop and/or at least one salt-bridge-disrupting point mutation which forms a single-block scRANKL or a double-block scRANKL.

8. A RANKL polypeptide in accordance with aspect 7, wherein the scRANKL is a single-block scRANKL.

9. A RANKL polypeptide in accordance with aspect 7, wherein the scRANKL is a double-block scRANKL.

10. A RANKL polypeptide in accordance with any of aspects 1-9, further comprising at least one point mutation that increases the affinity of RANKL for a RANK receptor compared to the polypeptide without the point mutation.

11. A RANKL polypeptide in accordance with aspect 10, wherein the at least one point mutation is selected from the group consisting of K194E, Q236H, F269Y, H270Y and a combination thereof.

12. A method of inhibiting bone resorption and/or osteoclastogenesis in a subject in need thereof, comprising, administering to the subject a therapeutically effective amount of a RANKL polypeptide of any of aspects 1-11.

13. A method of treating osteoporosis in a subject in need thereof, comprising: administering to the subject a therapeutically effective amount of a RANKL polypeptide of any of aspects 1-11.

14. A method of generating a RANK inhibitor, comprising: generating at least one first mutation in a RANKL polypeptide using error-prone PCR wherein the at least one first mutation increases affinity for RANK by at least 500-fold; and generating at least one second mutation in the RANKL polypeptide using error-prone PCR wherein the at least one second mutation is a RANK receptor-blocking mutation.

15. A method of generating a TNF inhibitor, comprising: generating at least one first mutation in a TNF using error-prone PCR, wherein the at least one first mutation decreases activation of TNFR1; and generating at least one second mutation in the TNF using error-prone PCR wherein the at least one second mutation decreases inhibition of TNFR2.

BRIEF DESCRIPTION OF THE DRAWINGS/FIGURES

FIG. 1A-FIG. 1D. Construction and validation of single-chain RANKL. (A) Wild-type (WT) homotrimeric RANKL (htRANKL) is assembled from three individual polypeptides (monomers), whereas WT single-chain RANKL (scRANKL) is a single polypeptide containing RANKL monomers that are joined by two [GGSG]x3 amino acid linkers. (B) Coomassie-stained SDS-PAGE gel of WT htRANKL chemically cross-linked by increasing concentrations of BS3. A sample of scRANKL without crosslinking is also shown. 500 ng of each protein was used. n=3 independent experiments. (C) BMMs were incubated in the presence of recombinant WT htRANKL or WT scRANKL as described in the Materials and Methods and the osteoclasts generated were identified by TRAP staining. n=5 independent experiments. (D) Individual monomers of single-block scRANKL or double-block scRANKL were mutated to inhibit their binding to RANK. Thus, single-block scRANKL contains two intact receptor-binding sites, whereas the double-block scRANKL contains one.

FIG. 2A-FIG. 2D. Design of scRANKL variants from mutants that do not bind to RANK. (A) The three labeled loops of RANKL form one side of the RANK-binding interface in the RANK-RANKL co-crystal structure. (9) (B) The binding of the indicated concentrations of WT htRANKL, CDins htRANKL, or GST (a negative control) to RANK-Fc (top) or OPG-Fc (bottom) after incubation for the indicated times was assessed by biolayer interferometry. Curves from triplicate experiments are shown. (C) Top: BMMs were incubated with WT htRANKL or CDins htRANKL (both at 200 ng/ml) and osteoclastogenesis was assessed by TRAP staining. Bottom: BMMs were incubated with WT htRANKL or CDins htRANKL (both at 200 ng/ml) for the indicated times. Cell lysates were then analyzed by Western blotting with antibodies against the indicated proteins to assess IκBα phosphorylation. Images and Western blots are representative of three independent experiments. (D) SPR analysis was used to measure the binding of equal amounts of the indicated scRANKL variants coupled to SPR chips to the analyte RANK. Binding curves were generated from triplicate measurements. The average number of RUs for each binding curve at saturation is displayed.

FIG. 3A-FIG. 3D. Generation of high-affinity RANKL mutants by YSD. (A) Histograms showing flow cytometric analysis of the staining of clones with 1 µM monomeric RANK at each phase of library sorting. To select for clones with increased binding to RANK, three rounds of sorting were initiated with a concentration of RANKL that was 10-fold greater than the $K_D$ of RANK (Sort #1) and terminated with a concentration of RANKL that was 10-fold less (Sort #3). (B) Point mutants of htRANKL generated by YSD. $K_D$ values were estimated by titrating different amounts of RANK with YSD htRANKL and fitting the median fluorescence intensity (MFI) values for RANK binding to a one-site binding model. Values represent the averages of three independent experiments. ND, not enough data points to fit $K_D$ values, despite having low amounts of detectable staining at the highest concentrations. The asterisk indicates that the reported affinity of htRANKL for monomeric RANK is 1 µM (9). (C, D) Kinetic and equilibrium affinities of WT htRANKL and KQFH htRANKL for RANK and OPG were determined by SPR measurements. Variants of htRANKL were coupled to a sensor chip and monomeric fragments of RANK or OPG served as analytes. Curve fits of triplicate runs are shown as black lines and values represent means±SD. $k_a$ (on-rate), $k_d$ (off-rate), $K_D$ (equilibrium dissociation constant).

FIG. 4A-FIG. 4F. Development of a competitive antagonist scRANKL. (A) Schematic displaying the mutations incorporated into the single-block, RANK$^{high}$ and double-block, RANK$^{high}$ variants. "X" indicates RANKL variant that does not bind RANK while up arrow indicates RANKL variant with increased affinity for RANK. (B) The relative abilities of WT scRANKL, single-block, RANK$^{high}$ and double-block, RANK$^{high}$ proteins to induce osteoclastogenesis in vitro was determined and quantified by a fluorescent TRAP activity assay. The curve shown is representative of three independent experiments. (C) BMMs were incubated with WT htRANKL or single-block, RANK$^{high}$ for the indicated times. Cell lysates were then analyzed by Western blotting with antibodies against the indicated proteins to determine the phosphorylation of IκBα and p38 MAPK. Western blots are representative of three independent experiments, with IκBα and p38 run in parallel on separate gels. (D) BMMs were incubated with WT htRANKL (200 ng/ml) alone (open diamond) or in the presence of the indicated concentrations of single-block, RANK$^{high}$ (squares) or double-block, RANK$^{high}$ (triangles). The extent of osteoclast formation was determined by measurement of TRAP activity. The curve shown is representative of four independent experiments. (E) BMMs and osteoblasts were co-cultured alone or in the presence of the indicated concentrations of single-block, RANK$^{high}$. Osteoclast numbers were determined by manually counting TRAP-positive multi-nucleated cells. Data are means±SD from three independent experiments. (F) Mice were injected with PBS as a negative control or with WT htRANKL (0.5 mg/kg) alone or together with single-block, RANK$^{high}$ (0.5 mg/kg). Two days later, serum concentrations of CTx were measured by ELISA. Data are means±SD from eight to ten mice per group performed in cohorts of 4-5 mice per group in two independent experiments. Data were analyzed by one-way ANOVA.

Figure 5A:
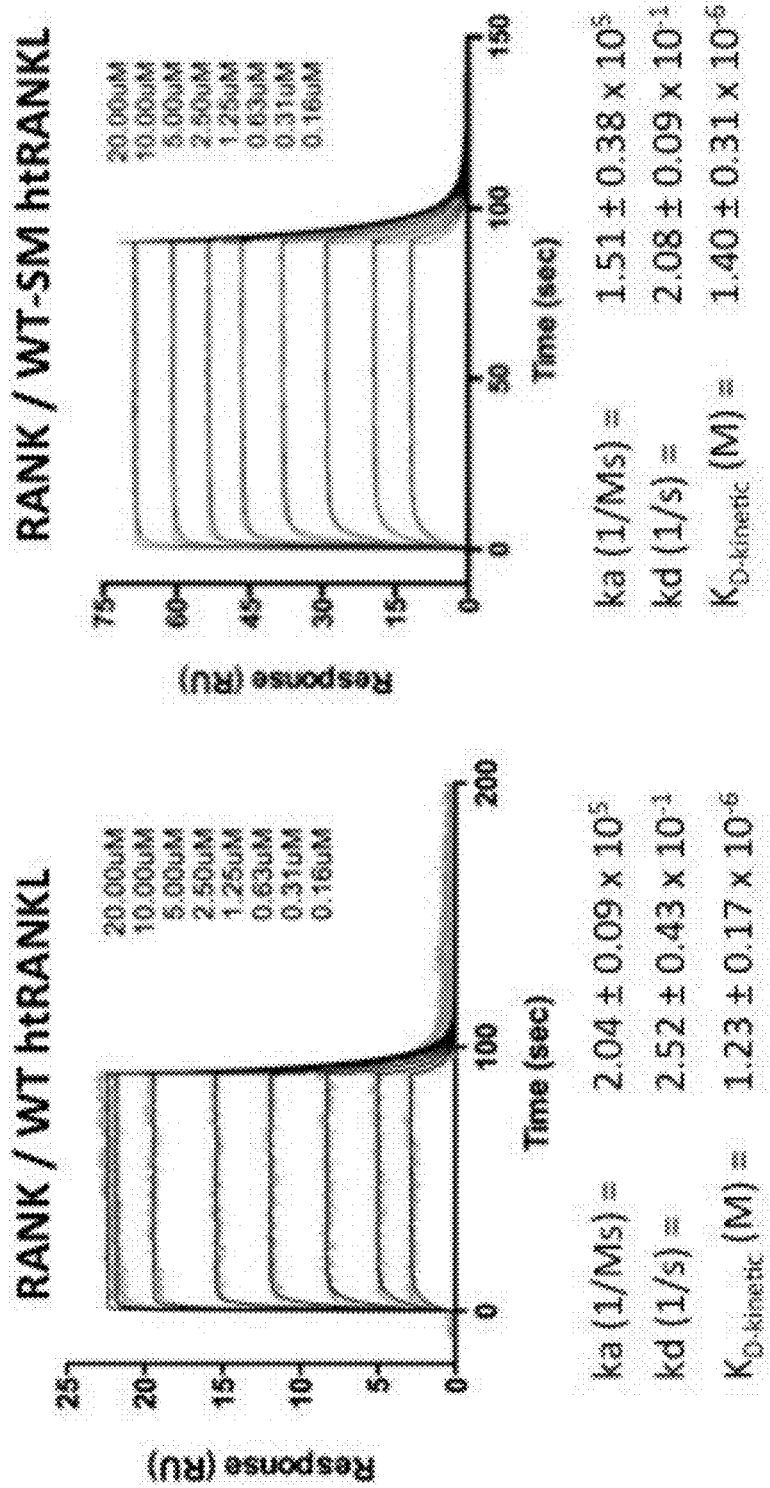
Figure 5B:
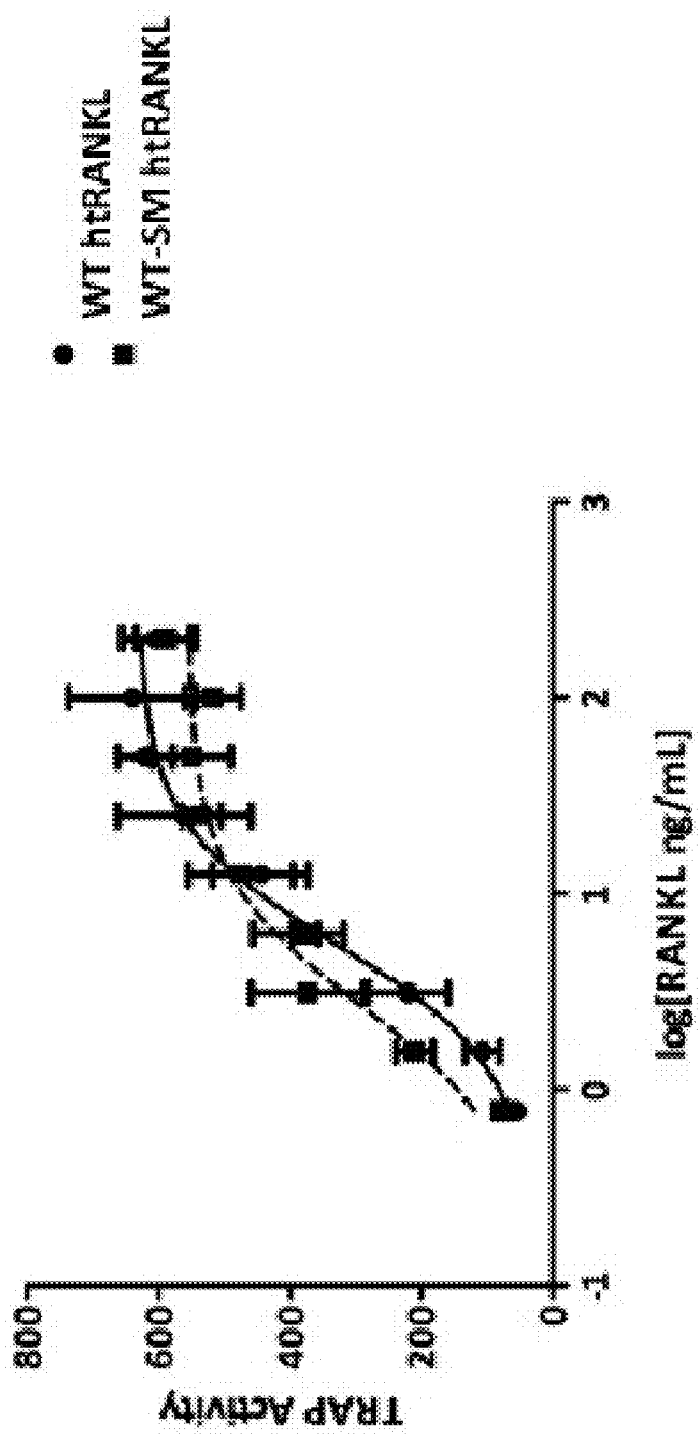

FIG. 5A-FIG. 5B. Effect of solubility mutations on RANKL function. (A) SPR assays were performed to determine the kinetic affinities for RANK of WT RANKL and of WT RANKL containing two mutations that increase its solubility (C220S and E246I, WT-SM RANKL). Curves were generated from triplicate samples. Kinetics values beneath the graphs represent means±SD from three independent experiments. (B) BMMs were incubated with the indicated concentrations of WT htRANKL and WT-SM htRANKL, and the extent of osteoclastogenesis was determined by a fluorescent TRAP activity assay. Curves are representative of three independent experiments.

Figure 1B:
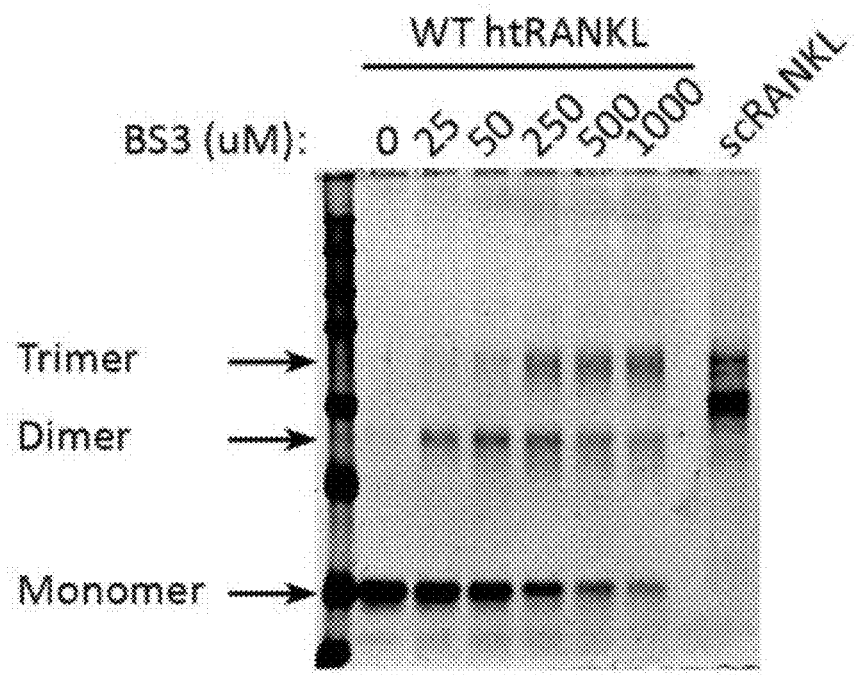
Figure 6A:
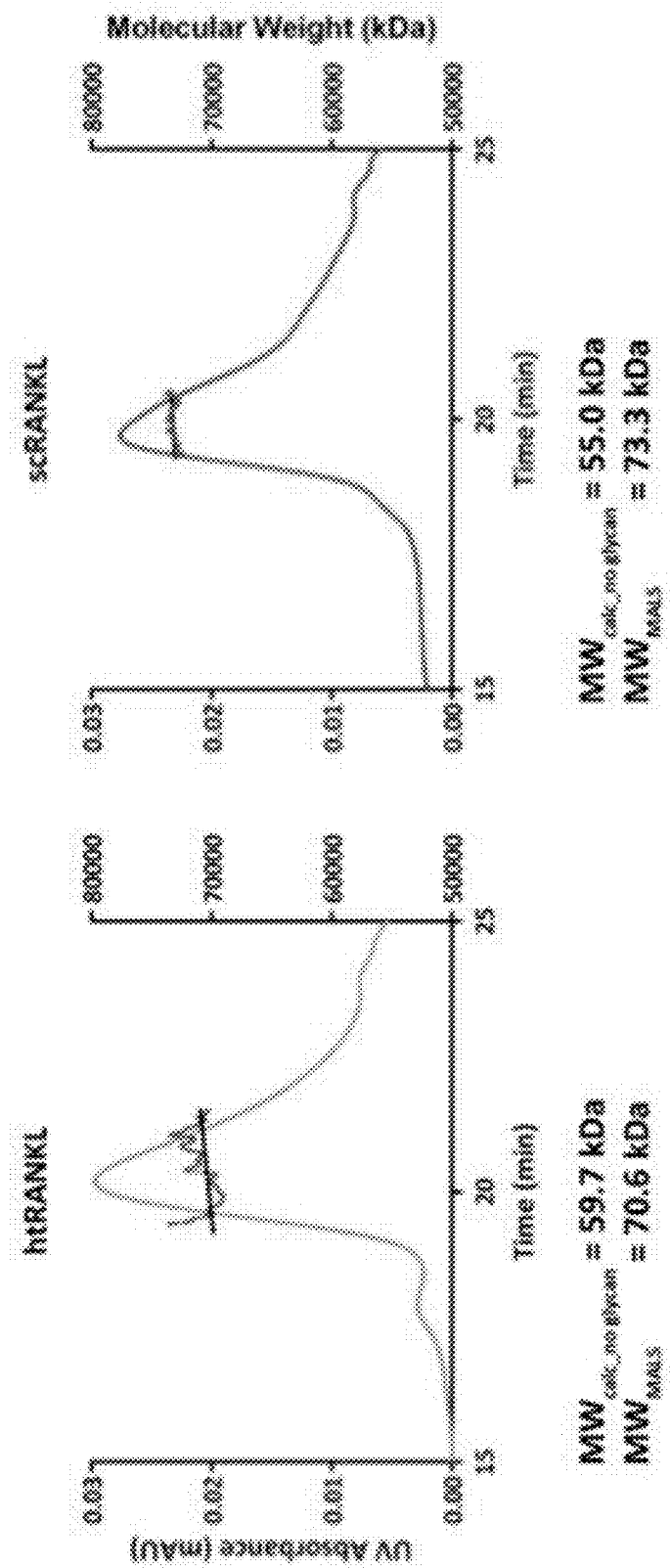
Figure 6B:
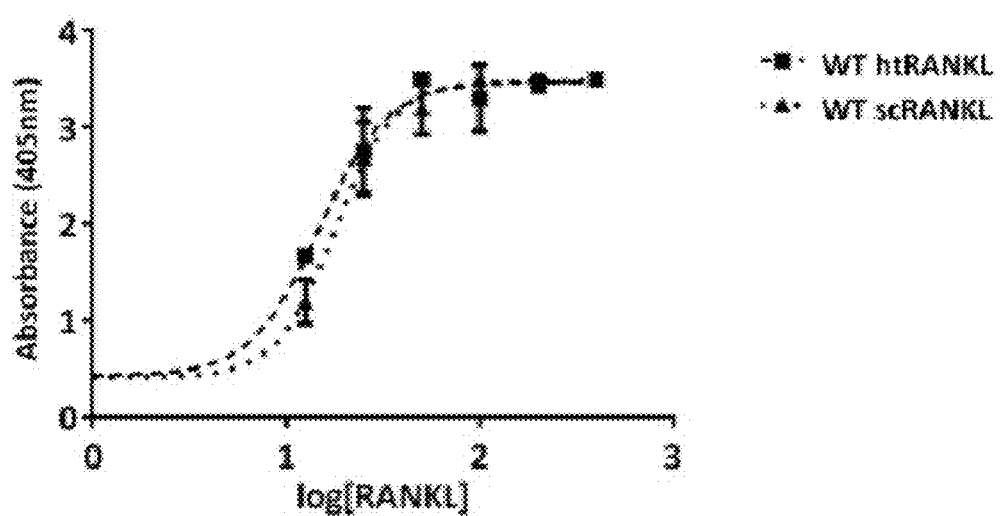
Figure 7B:
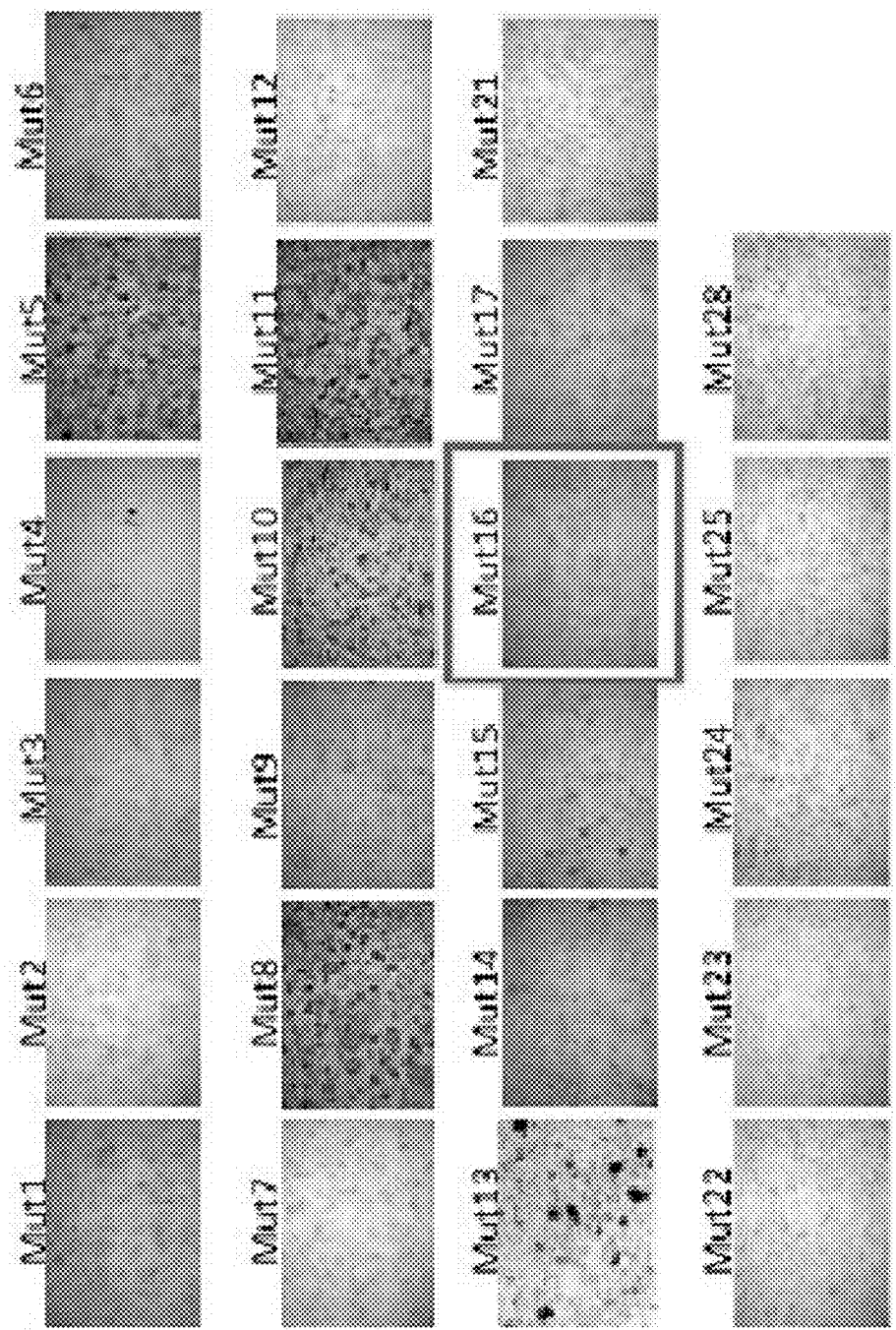
Figure 7D:
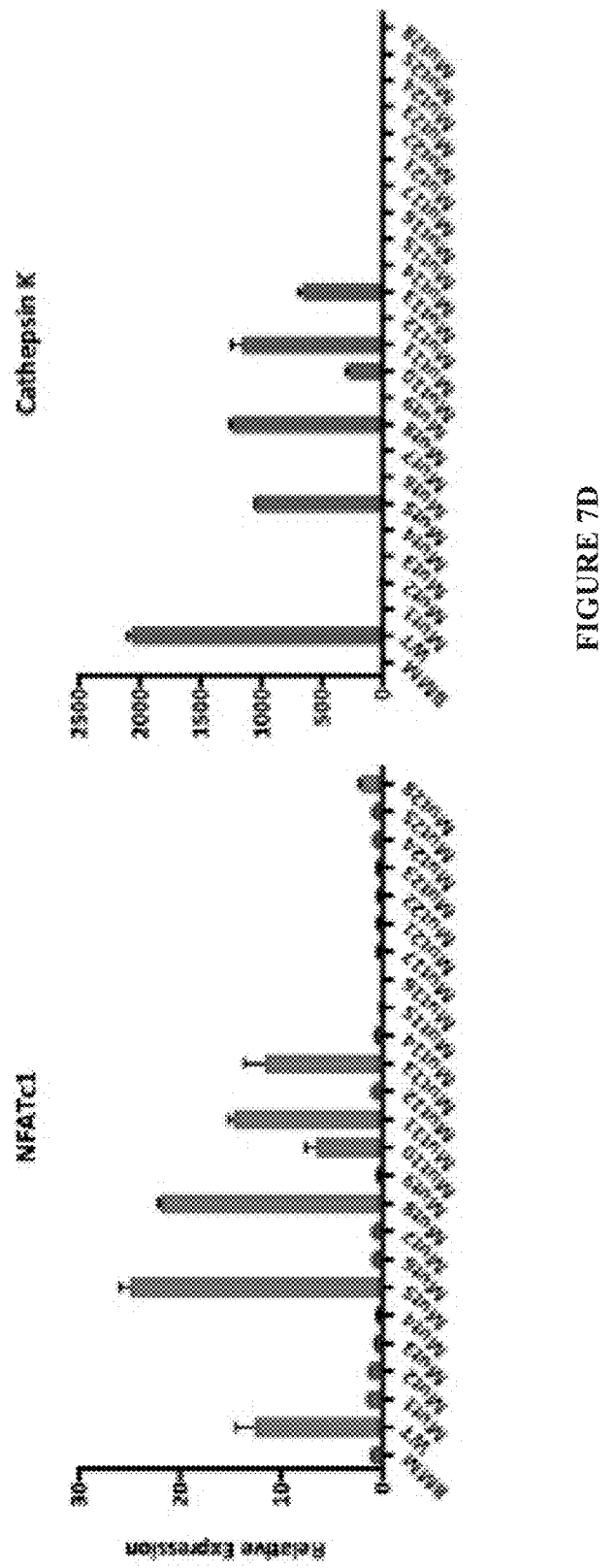

FIG. 6A-FIG. 6B. Comparison of WT htRANKL and scRANKL. (A) MALS analysis of noncovalently linked RANKL (htRANKL) or single-chain RANKL (scRANKL). Because the predominant scRANKL species migrated on a denaturing gel at a position slightly below that of chemically cross-linked htRANKL (FIG. 1B), we calculated the precise molecular mass of htRANKL (left) and scRANKL (right) by MALS. The differences in the calculated and measured molecular masses reflect the presence of substantial glycosylation on these proteins, which are secreted by mammalian cells. Data are representative of three independent experiments. (B) BMMs were incubated with the indicated concentrations of WT htRANKL or WT scRANKL, and the extent of osteoclastogenesis was measured by a colorimetric solution-based TRAP assay. The curves are representative of three independent experiments.

FIG. 7A-FIG. 7D. Selection of RANKL mutants that prevent binding to RANK. (A) The binding of the indicated htRANKL variants to RANK-Fc or OPG-Fc was assessed by BLI. Because of the dimeric nature of the analyte, $K_D$ values represent the apparent affinity constants generated from triplicate curves. (B to D) The capacity of the indicated recombinant htRANKL variants to induce osteoclastogenesis in vitro was assessed by (B) TRAP staining, (C) TRAP-solution assay, and (D) real-time PCR analysis of the relative abundances of mRNAs for osteoclastogenic markers. All assays were performed in technical triplicates. Mut16 was selected for incorporation into scRANKL and is highlighted in a red box.

Figure 8:
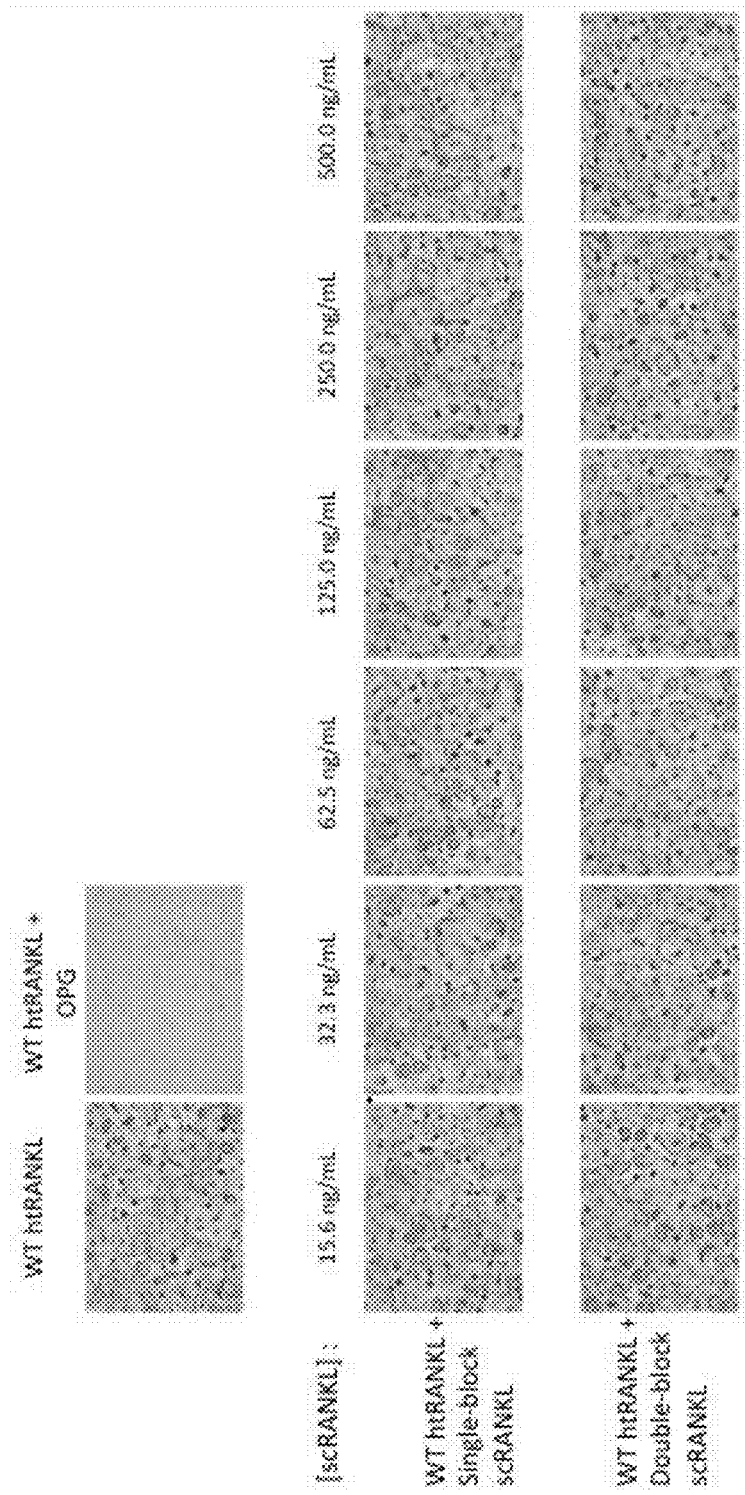

FIG. 8. Ability of scRANKL variants to inhibit WT htRANKL-induced osteoclastogenesis. BMMs were cultured with WT htRANKL (200 ng/ml) and the indicated concentrations of either single-block scRANKL or double-block scRANKL. Four days later, osteoclastogenesis was assessed by TRAP staining. The addition of a monomeric fragment of OPG (4 µg/ml) to cells treated with WT htRANKL was used to demonstrate inhibition of osteoclastogenesis. Images are representative of three independent experiments.

FIG. 9A-FIG. 9D. Reversion mutagenesis of YSD htRANKL clones. (A to D) Yeast cells were induced to express RANKL variants and stained with RANK-Fc (left column in sets of two for each mutant) or OPG-Fc (right column in sets of two for each mutant). The degree of staining detected by flow cytometry was expressed as a percent relative to WT. (A) Top scoring clones from the low (LM3S) or high (HM3S) mutation rate libraries with (B) individual point mutations of these clones. Data are representative of two independent experiments (A and B). (C) A second mutation was added to the most effective individual point mutant (Q236H). (D) A third mutation was added to closely approximate the ideal phenotype. Data are representative of two independent experiments (C and D).

Figure 10A:
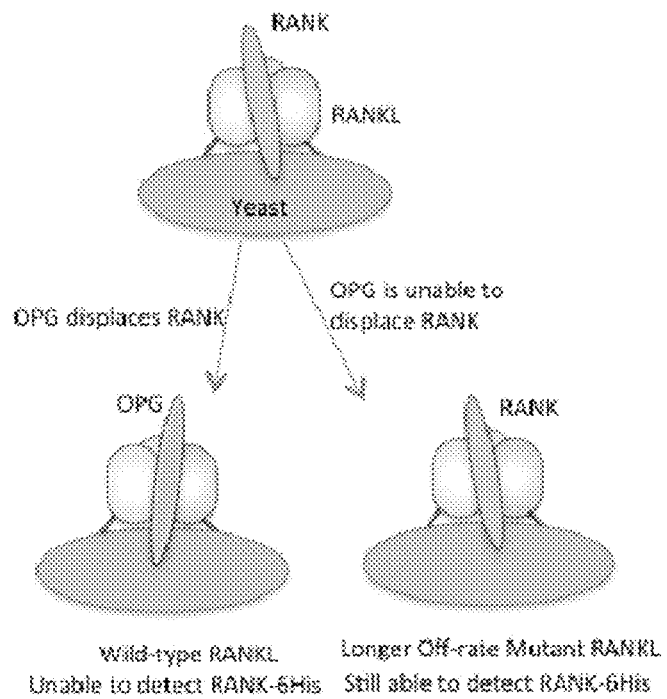
Figure 10B:
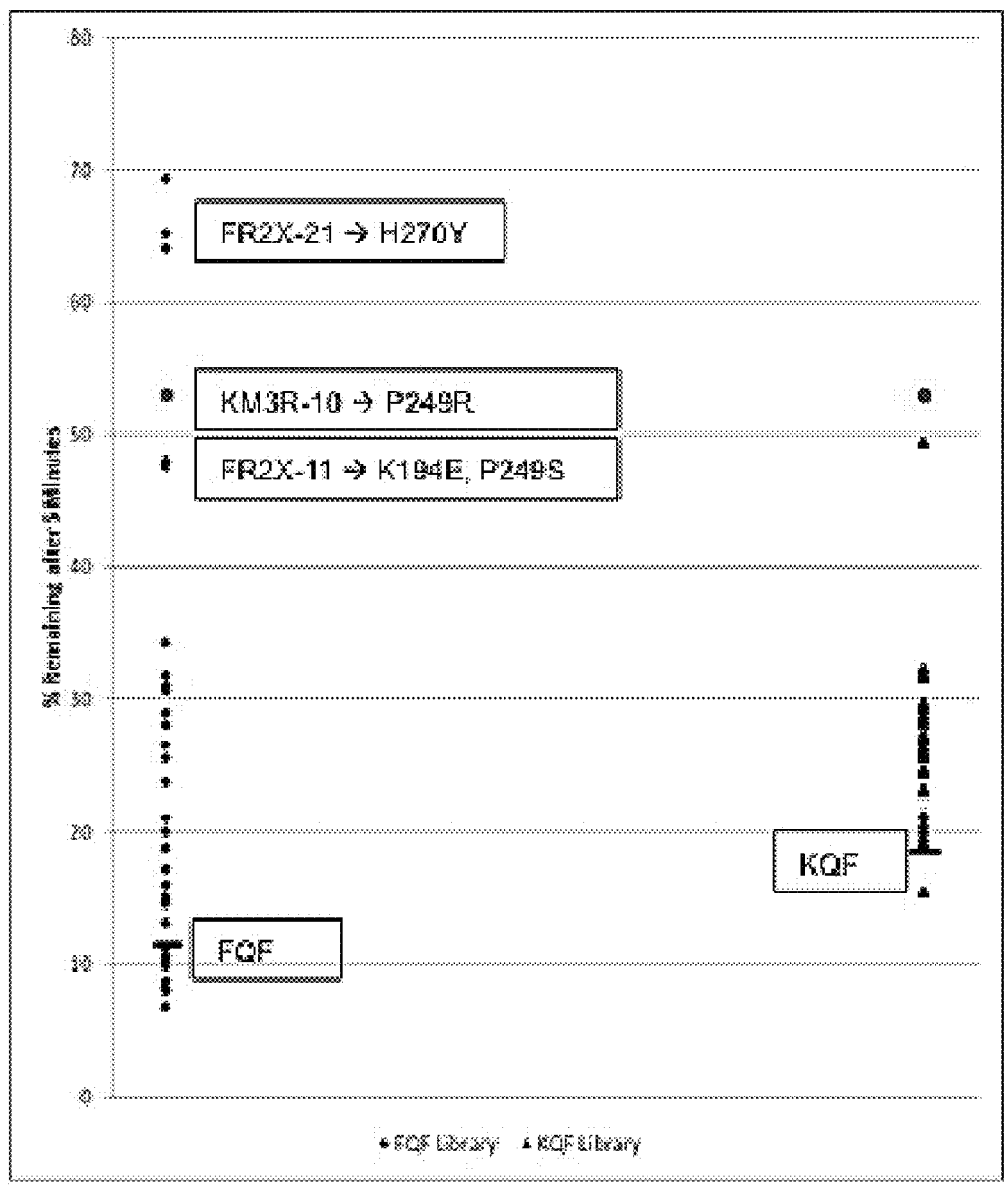
Figure 10C:
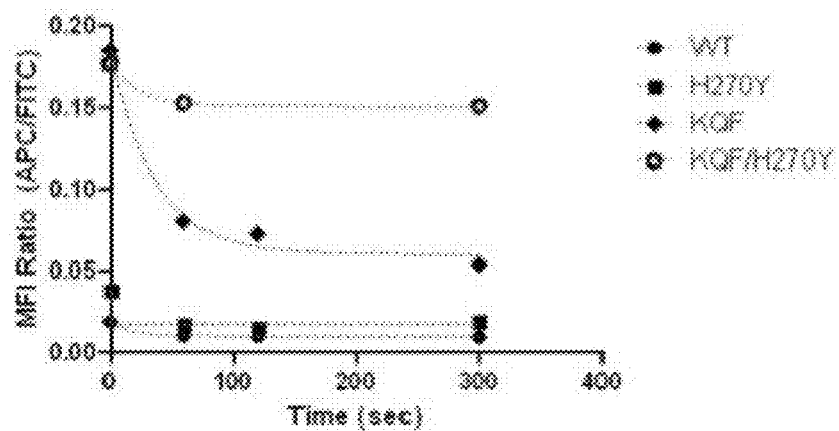
Figure 11:
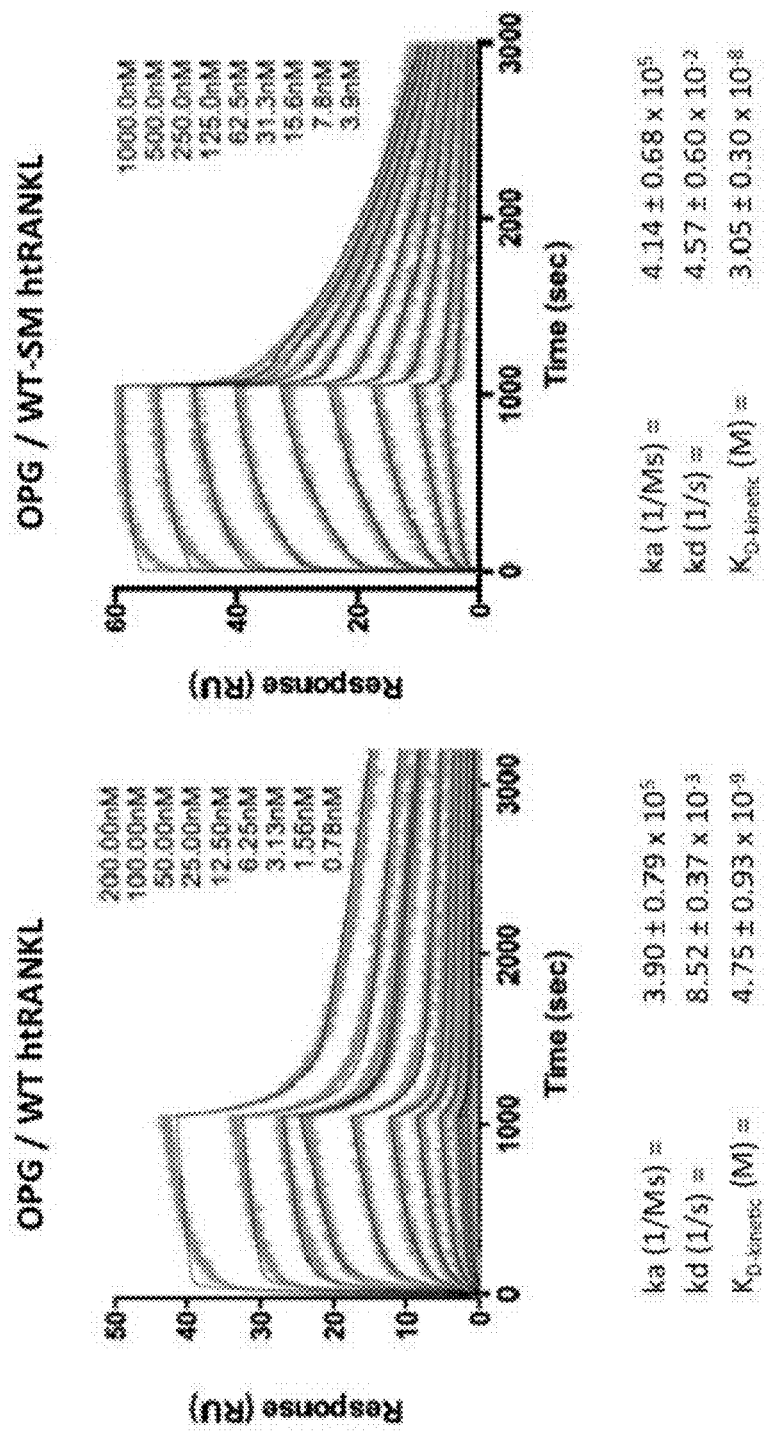
Figure 12:
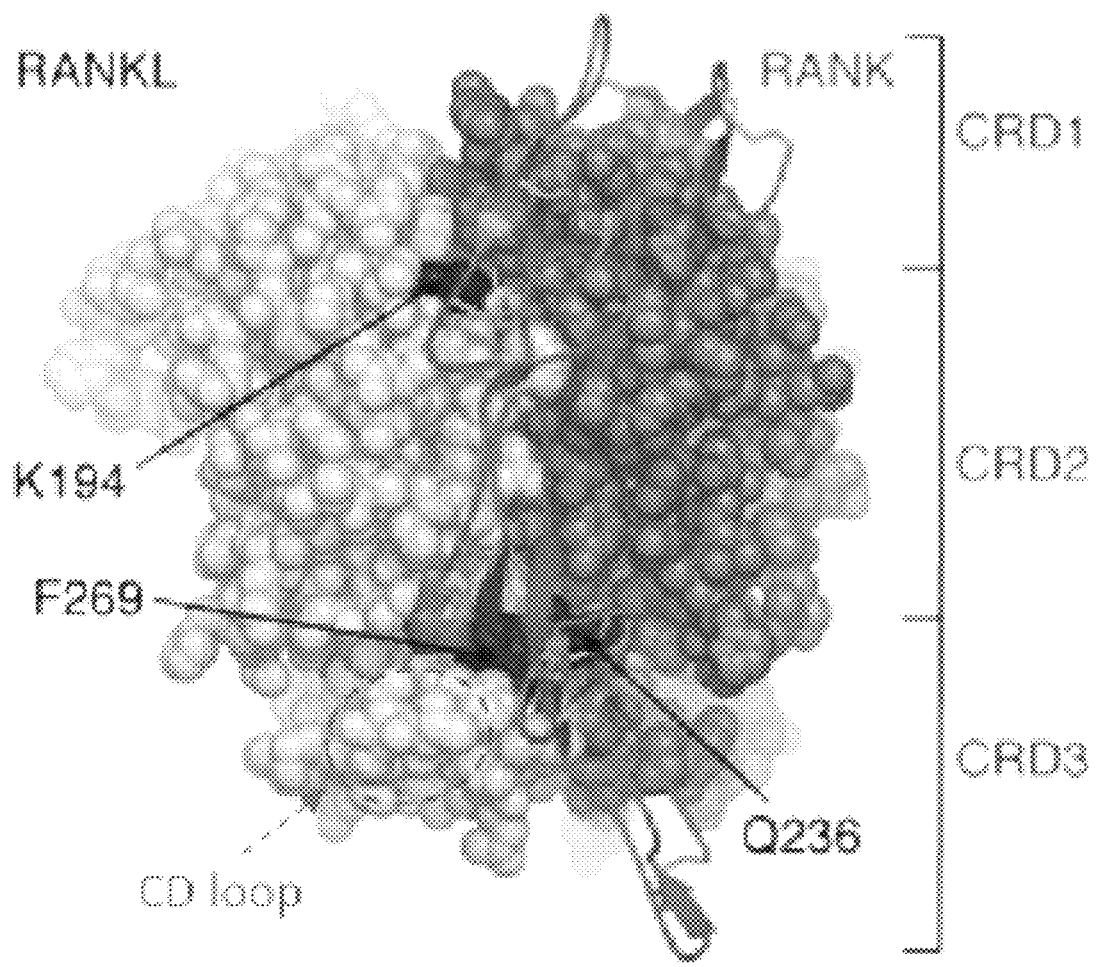
Figure 13A:
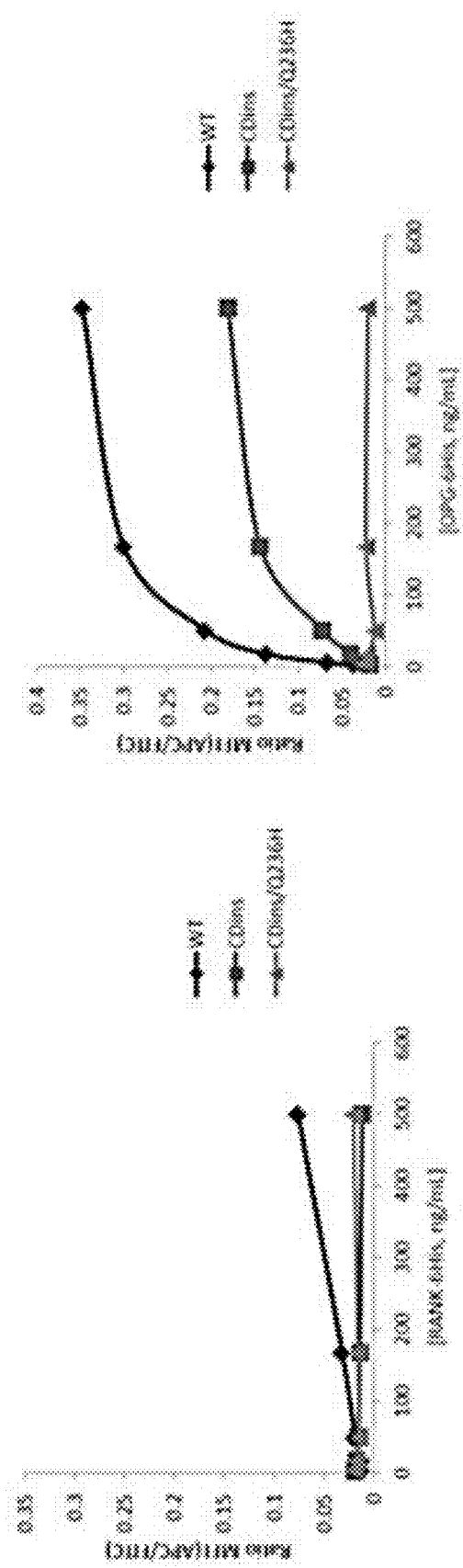
Figure 13B:
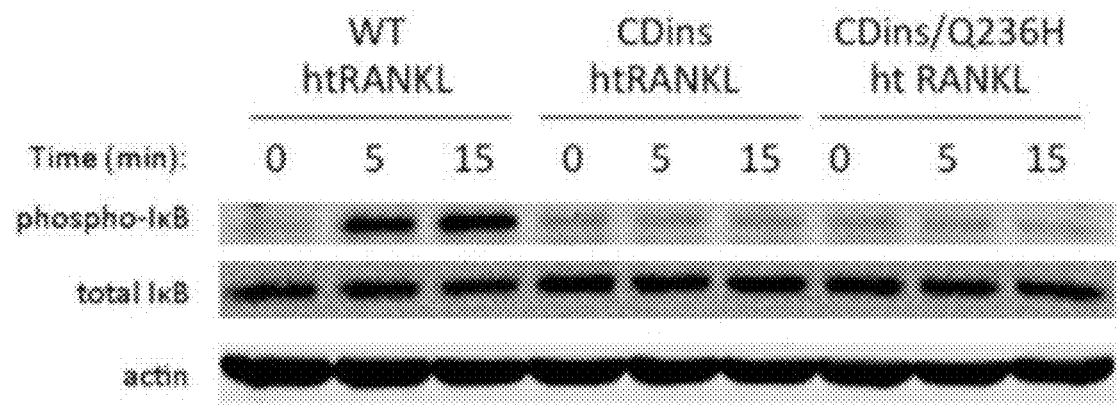
Figure 13C:
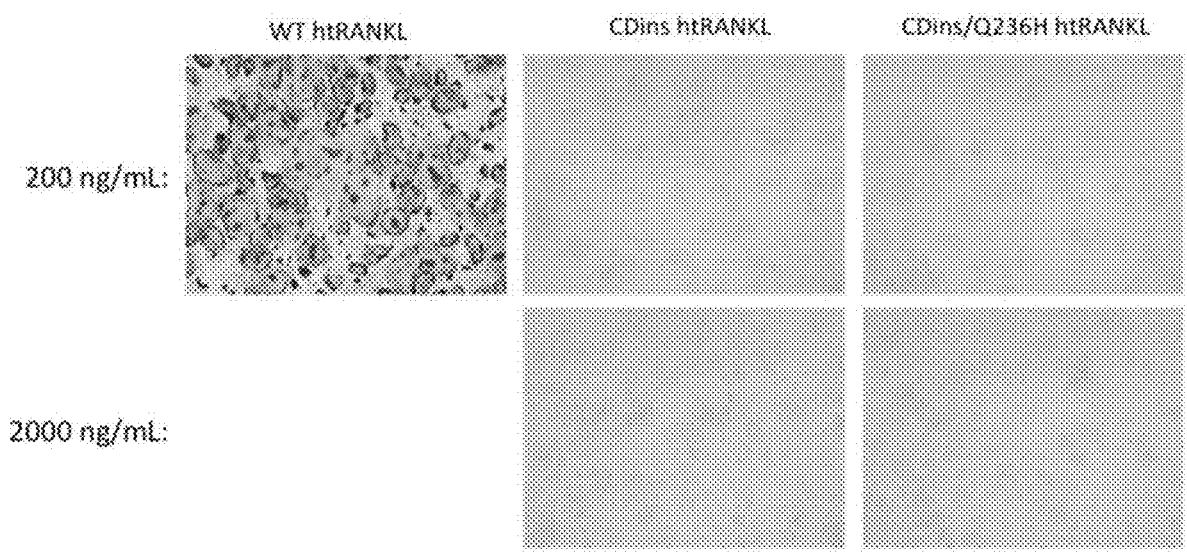
Figure 14A:
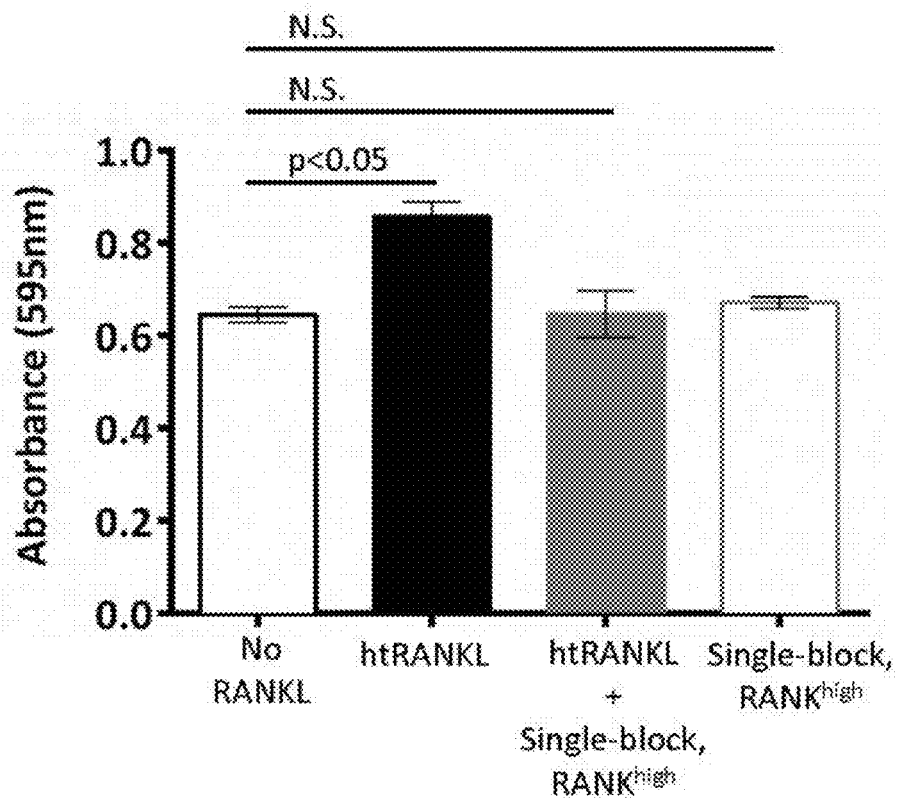
Figure 14B:
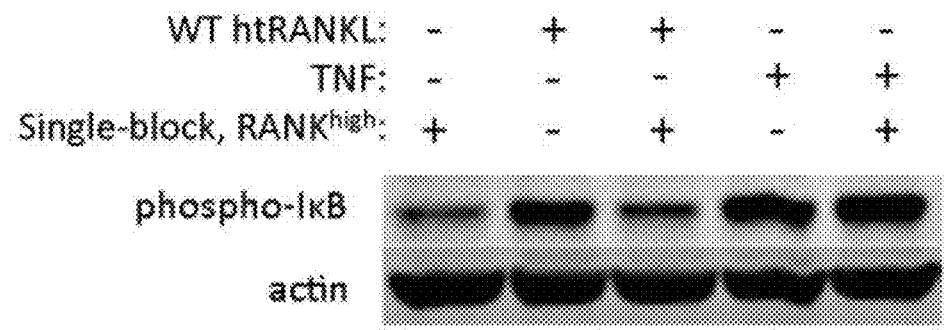

FIG. 10A-FIG. 10C. Identification of htRANKL mutants with prolonged off-rates and decreased binding to OPG by a competitive OPG screen. (A) Representation of the competitive OPG YSD screen. In the context of WT htRANKL (left), RANK (top) fused to a 6×His tag is readily displaced by OPG (bottom left) because of the higher affinity of OPG. Alternatively, in the context of a htRANKL clone that has increased affinity for RANK and that has lost the capacity to bind to the decoy receptor, OPG is incapable of displacing RANK (bottom right). Additionally, only those clones with an increased half-life have sustained binding after washing at room temperature. (B) Individual point mutant htRANKL clones retaining high RANK binding, as detected with a monoclonal antibody against the 6×His tag, after 5 min of competition with OPG. (C) Kinetic competition analysis of the binding of WT htRANKL and the H270Y, KQF, and KQFH htRANKL variants to RANK-6His, in the presence of OPG, based on flow cytometric screening. For (B) and (C), data are expressed as the percentage of htRANKL bound to RANK over time relative to that bound in the absence of OPG. Additionally, the binding of RANK (as detected with an APC-conjugated antibody) was normalized to the amount of htRANKL expressed on the surface of the yeast (as detected with a FITC-conjugated antibody) and expressed as the ratio of the MFIs of the APC and FITC signals. Curves are representative of three independent experiments.

FIG. 11. Effect of htRANKL solubility mutations on binding to OPG. The kinetic affinities of WT-htRANKL and WT-SM htRANKL for OPG were determined by SPR analysis. Curves were generated from triplicate measurements. Values below the plots are means±SD of three independent experiments.

FIG. 12. Van der Waals surface model of WT htRANKL oriented to show the binding cleft. For simplicity, only the two foremost htRANKL monomers are shown; one in gray (darker, right) and the other in white (lighter, left). The RANKL substitution positions selected by YSD are shown in blue. The three residues that can be seen in this view, K194, F269, and Q236, have been labeled. The fourth residue, H270, lies just behind F269. A darkened ribbon model of RANK is shown in the binding cleft, with disulfide bonds inlight lines. Only three of the cysteine-rich domains of RANK are shown. The CD-loop is indicated by a dashed circle.

FIG. 13A-FIG. 13C. Combined mutations of htRANKL that block binding to RANK and OPG. (A) Titration curves of the binding of CDins htRANKL and CDins/Q236H htRANKL to RANK and OPG as assessed by the flow cytometric analysis of yeast cells displaying htRANKL. The binding of RANK or OPG (as detected with APC-conjugated antibodies) was normalized to the amount of htRANKL expressed at the yeast cell surface (as detected with a FITC-conjugated antibody) and was expressed as the ratio of the MFIs of the APC and FITC signals. Curves represent three independent experiments. (B) BMMs were left untreated or were treated with the indicated htRANKL constructs (500 ng/ml) for 5 and 15 min. Cell lysates were then analyzed by Western blotting with antibodies against the indicated proteins. Western blots are representative of three independent experiments. (C) BMMs were incubated with CDins htRANKL or CDins/Q236H htRANKL to generate osteoclasts in vitro at concentrations that were saturating for WT htRANKL (200 ng/ml) or were 10-fold greater (2,000 ng/ml). Images are representative of three independent experiments.

FIG. 14A-FIG. 14B. Effects of single-block, RANK$^{high}$ on cell number and signaling. (A) D2 osteoclasts were left untreated or were incubated with WT htRANKL alone, single-block, RANK$^{high}$ alone, or a combination of both. Cells were then analyzed by MTT assay to determine the effects on cell number. Data are means±SD from three independent experiments and were analyzed by one-way ANOVA. (B) BMMs were left untreated or were preincubated for 15 min with single-block, RANK$^{high}$ (500 ng/ml) before being incubated with WT htRANKL (200 ng/ml) or TNF-α (1 ng/ml). Cell lysates were then analyzed by Western blotting with antibodies against the indicated proteins to examine the extent of phosphorylation of IκBα. Western blots are representative of three independent experiments.

FIG. 15A-FIG. 15C. Receptor interfaces in a scTNFsfL. (A) Each scTNFsfL monomer is labeled "A", "B", or "C" and is shown connected by the peptide linkers (lines). The interfaces capable of accepting the TNFsf receptor have been arbitrarily named "X", "Y", and "Z". The TNFsf A'A" and GH loops contribute to the side of the interface termed "L", and the DE and FG loops contribute to the side termed "R". Depicted are two possible conformations of scTNFsfL, one that has folded with a right-handed orientation and one folded with a left-handed orientation. The CD and EF loops can contribute to both left and right sides of the interface. The possible interfaces with corresponding contributions from each monomer are indicated below the diagram. (B) Single-block scRANKL provides one example of how individually mutated receptors can yield identical binding interfaces regardless of the right- or left-handed nature of scRANKL folding. *Note that CDins from the "L" side of an interface combined with either a WT or Q236H ("Q") contributed from the "R" side comprise a receptor blocking interface, while KFH from the "L" side combined with Q from the R side form a high affinity interface. (C) Single-block, RANK$^{high}$ scRANKL interfaces as in (B).

FIG. 16. The structural elements of RANKL (loops and strands) are labeled as described in the original crystal structure (9). The view is directly into the binding site showing both sides of the RANK-binding interface.

DETAILED DESCRIPTION

Provided herein are single chain TNFsf ligands (scTNFsfL) that can effectively antagonize corresponding TNFsf target receptors. In certain embodiments, the scTNFsfL provided herein will selectively inhibit target TNSF receptors while not inhibiting non-target (i.e., decoy) TNFsf receptors. In certain embodiments, the scTNFsfL is a scRANKL comprising a combination of blocked and high-affinity RANK binding sites that inhibits RANK signaling, thus acting as an effective inhibitor of RANKL-mediated osteoclast formation and function. RANKL. RANKL is a member of the TNF superfamily of cytokines, which binds to multiple receptors (RANK and OPG) with different biological effects. In certain embodiments the scTNFsfL provided herein will selectively inhibit a target TNFsf receptor while selectively avoiding non-target (i.e., decoy) receptors that would normally limit the effectiveness against the target receptor. This would have the added benefit of allowing the non-target (i.e., decoy) receptors to continue to inhibit wild-type TNFsfL without interference from the scTNFsfL. In certain embodiments, a single chain RANK ligand (scRANKL) provided herein can comprise a combination of blocking and high affinity mutations which can recognize RANK with high affinity but can fail to recognize osteoprotegerin, thus inhibiting productive and undesirable signaling through RANK by endogenous RANKL while permitting productive and desirable signaling through OPG by endogenous RANKL. Such scRANKL provided herein are useful for inhibiting bone resorption in vivo, and for treating or preventing bone loss diseases such as osteoporosis or inflammatory osteolysis in a human or other mammalian subject. Within the TNFsf, there are several examples of cytokines that demonstrate promiscuity in receptor usage (21). For example, TNF-α, which recognizes both TNFR1 and TNFR2, is central to the pathogenesis of disabling disorders, such as rheumatoid arthritis and psoriasis (22). Indeed, treatment of these diseases has been greatly facilitated by systemic blockade of TNF-α with humanized antibodies or soluble receptor (23, 24). As effective as these drugs are, however, they cause major complications, such as a predisposition to malignancy and serious infections, including tuberculosis (25, 26). Current evidence indicates that the positive effects of anti-TNF-α therapy reflects suppressed activation of TNFR1, whereas the negative consequences are a result of inhibition of the pro-immune properties of TNFR2 (27, 28). TNF and RANKL interact with their receptors in a homologous fashion (9, 10, 29, 30). Provided herein are methods of combining high-affinity mutations and blocking mutations into a single-chain that can be used to construct an effective inhibitor that is receptor-selective. Also provided herein are scTNFsfL and compositions comprising the same as well as methods of using such scTNFsfL and compositions to treat human or animal subjects suffering from disorders where inhibition of corresponding TNFsf receptors is indicated. Also provided herewith are potential mechanisms for blocking TNFR1 stimulation while sparing TNFR2, thereby reducing systemic complications. In principal, a covalently linked system (e.g., a scTNFsfL) offers an advantage over the use of mixed heterotrimers (31) in that the composition of each receptor-binding interface is pre-determined. Indeed, this strategy may be broadly applicable to all members of the pathologically important TNF superfamily.

ABBREVIATIONS

The following abbreviations are used herein.
APC is Allophycocyanin.
BLI is Bio-layer interferometry
BMM are Bone marrow macrophages.
CTx C-terminal telopeptide.
ELISA is Enzyme-linked immunosorbent assay.
FITC is Fluorescein isothiocyanate.
GST is Glutathione S-transferase.
KQF are the K194E, Q236H, F269Y amino acid substitutions in the mouse RANKL monomer amino acid sequence of SEQ ID NO:1.
LPS is Lipopolysaccharide.
MALS is Multi-angle light scattering.
MEM is Minimum essential medium.
MFI is Mean fluorescence intensity.
NCBI is the National Center for Biotechnology Information.
Ni-NTA is Ni-nitrilotriacetic acid.
OPG is Osteoprotegerin.
PBS is Phosphate buffered saline.
PCR is Polymerase chain reaction.
RANK is Receptor activator of NF-kappaB.
RANKL is Receptor activator of NF-kappaB ligand.
RU is Resonance units.
scRANKL is Single-chain Receptor activator of NF-kappaB ligand.
SDS-PAGE is Sodium dodecyl sulfate polyacrylamide gel electrophoresis.
SPR is Surface plasmon resonance
TEV is Tobacco Etch Virus.
TNF is Tumor necrosis factor.
TNFsf is Tumor necrosis factor superfamily.
TRAP is Telomeric repeat amplification protocol.
WT is Wild type.
WT-SM RANKL is Wild type-solubility mutations (i.e., the C220S and I246E amino acid substitutions in the mouse RANKL monomer amino acid sequence of SEQ ID NO: 1 to yield SEQ ID NO:7).
YSD is Yeast Surface Display.

Definitions

As used herein, the phrase "binding affinity" or "affinity" refers to the $K_D$ (equilibrium dissociation constant) of ligand and a receptor.

As used herein, the phrases "blocks binding of a TNFsf member" or "blocking mutation(s)" refer to mutations that reduce or essentially eliminate binding of a TNFsf homo-trimer comprising monomers with the mutation to a corresponding target TNFsf receptor in comparison to the binding of a TNFsf homo-trimer comprising wild-type monomers to that same receptor. In certain embodiments, such reductions are at least a two-, three-, four-, five-, seven-, ten, 20-, 50-, or 100-fold reduction in binding affinity of a TNFsf homo-trimer comprising monomers with the mutation to a corresponding target TNFsf receptor in comparison to the binding affinity of a homo-trimer comprising wild-type monomers to the corresponding target TNFsf receptor.

As used herein, the phrase "mutation that increases binding affinity of a TNFsf member comprising the second mutated monomer to the corresponding target Tumor Necrosis Factor superfamily receptor" refers to mutations that increase binding of a TNFsf homo-trimer comprising monomers with the mutations to a corresponding target TNFsf receptor in comparison to the binding of a TNFsf homo-trimer comprising wild-type monomers to that same target TNFsf receptor. In certain embodiments, such binding increases are at least a two-, three-, four-, five-, seven-, ten-fold, 50-fold, 100-fold, or 500-fold increase in binding affinity of the TNFsf homo-trimer comprising monomers with the mutation(s) to a corresponding target TNFsf receptor in comparison to the binding affinity of a homo-trimer comprising wild-type monomers to the corresponding target TNFsf receptor.

As used herein, the phrase "mutation that decreases binding affinity of a TNFsf member comprising the three monomers with the third mutation to a non-target Tumor Necrosis Factor superfamily receptor" refers to mutations that decrease binding of a TNFsf homo-trimer comprising monomers with the mutation(s) to a corresponding non-target TNFsf receptor in comparison to the binding of a TNFsf homo-trimer comprising wild-type monomers to that same non-target receptor. In certain embodiments, such binding decreases are at least a two-, three-, four-, five-, seven-, ten-, 20-, 50-, or 100-fold decrease in binding affinity of the TNFsf homo-trimer comprising monomers with the mutation(s) to a corresponding target TNFsf receptor in comparison to the binding affinity of a homo-trimer comprising wild-type monomers to the corresponding target TNFsf receptor.

As used herein, the phrase "subject in need thereof" refers to a subject in need of a treatment or preventative therapy to address a condition resulting from activity of a target TNFsf receptor in the subject. In certain embodiments, the "subject in need thereof" can be a subject that would benefit from a treatment or preventative therapy that will inhibit a target TNFsf receptor but that will have a reduced or negligible inhibitory effect on a non-target TNFsf receptor.

As used herein, the phrase "effective amount" refers to the amount of a scTNFsfL that is effective in inhibiting a target TNFsf receptor activity in a subject or cell.

As used herein, phrase "pharmaceutically acceptable" is employed herein to refer to those compounds, materials, compositions, and/or dosage forms which are suitable for use in a subject.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or stearic acid), solvent or encapsulating material, involved in carrying or transporting the therapeutic compound for administration to the subject. Each excipient should be "acceptable" in the sense of being compatible with the other ingredients of the formulation and not injurious to the subject. Pharmaceutically-acceptable excipients include, but are not limited to, amino acids (e.g., glycine, glutamine, asparagine, arginine, or lysine), antimicrobials, antioxidants (e.g., ascorbic acid, sodium sulfite, or sodium hydrogen-sulfite), buffers (e.g., borate, bicarbonate, Tris-HCl, citrates, phosphates, or other organic acids), bulking agents (e.g., mannitol or glycine), chelating agents (e.g., ethylenediamine tetraacetic acid (EDTA)), complexing agents (e.g., caffeine, polyvinylpyrrolidone, beta-cyclodextrin, or hydroxypropyl-beta-cyclodextrin), fillers, monosaccharides, disaccharides, and other carbohydrates (e.g., glucose, mannose, or dextrins), proteins (e.g., serum albumin, gelatin, or immunoglobulins), coloring, flavoring and diluting agents, emulsifying agents, hydrophilic polymers (e.g., polyvinylpyrrolidone), low molecular weight polypeptides, salt-forming counterions (e.g., sodium), preservatives (e.g., benzalkonium chloride, benzoic acid, salicylic acid, thimerosal, phenethyl alcohol, methylparaben, propylparaben, chlorhexidine, sorbic acid, or hydrogen peroxide), solvents (e.g., glycerin, propylene glycol, or polyethylene glycol), sugar alcohols (e.g., mannitol or sorbitol), suspending agents, surfactants or wetting agents (e.g., pluronics; PEG; sorbitan esters; polysorbates e.g., polysorbate 20 or polysorbate 80; triton; tromethamine; lecithin; cholesterol or tyloxapal), stability enhancing agents (e.g., sucrose or sorbitol), tonicity enhancing agents (e.g., alkali m et al halides-preferably sodium or potassium chloride- or mannitol sorbitol), delivery vehicles, diluents, excipients and/or pharmaceutical adjuvants. Other suitable excipients can be found in standard pharmaceutical texts, e.g. in "Remington's Pharmaceutical Sciences", The Science and Practice of Pharmacy, 19.sup.th Ed. Mack Publishing Company, Easton, Pa., (1995).

As used herein, the phrase "TNF superfamily (TNFsf)" is applied to ligands that fall within this family, their corresponding target receptors, and their non-target receptors (e.g., decoy receptors). Members of the TNFsf, their target receptors, and their non-target receptors are set forth in Table 1.

TABLE 1

TNFsf ligands, target receptors, and non-target receptors.

| TNFsf Ligand | Other ligand names | Target Receptor | Non-Target Receptor |
|---|---|---|---|
| RANKL | TNFSF11; ODF; OPGL; sOdf; CD254; OPTB2; TRANCE; hRANKL2 | RANK | OPG |
| TNF | DIF; TNFA; TNFSF2; TNF-alpha | TNFR1 | TNFR2 |
| TRAIL | TL2; APO2L; CD253; TNFSF10; Apo-2L | DR5 | DR4 |
| 4-1BBL | TNFSF9, CD137L | | |
| APRIL | TNFSF13 | B cell maturation antigen (BCMA) or cyclophilin ligand interactor (TACT) | cyclophilin ligand interactor (TACI) or B cell maturation antigen (BCMA) |
| BAFF | TNFSF13B | | |
| CD27L | TNFSF7 | | |
| CD30L | TNFSF8 | | |
| CD40L | TNFSF5 | | |
| EDA1 | EDA-A1 | | |
| EDA2 | EDA-A2 | | |
| FasL | TNFSF6 | | |
| GITRL | TNFS18 | | |
| LIGHT | TNFSF14 | | |
| Lymphotoxin alpha | TNFS1, LTA | | |
| Lymphotoxin alpha beta | TNFS3 | | |
| OX40L | TNFSF4 | | |
| TL1A | TNFSF15 | | |
| TWEAK | TNFSF12 | | |

The proteins encoded by the TNFsf members cited in Table 1 and certain mutations in those proteins are at least disclosed in U.S. Pat. No. 8,590,273, which is incorporated herein by reference in its entirety with respect to those sequences and mutations.

As used herein the phrase "operably linked" refers to joining nucleic acid sequences, nucleic acid sequences encoding protein sequences, or protein sequences in a manner that retains the respective functions of each joined sequence. Examples of operable linkage of nucleic acid sequences include, but are not limited to, linkage of promoters to mRNA coding sequences in a manner that provides for transcription of the mRNA under control of the promoter. Examples of operable linkage of nucleic acid sequences encoding protein sequences include, but are not limited to, linkage of a sequence encoding a signal peptide to a protein coding sequence such that the fusion protein will be translated in the correct reading frame and provide for secretion of the protein coding sequence when expressed in a host cell.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Further Description

Mutations used in the scTNFsfL provided herein can exhibit at least three functional characteristics. A first set of mutations that is used are "blocking mutations" that can reduce or essentially eliminate binding to a corresponding target TNFsf receptor. A second set of mutations that can be used are mutations that can increase binding affinity to the corresponding target TNFsf receptor and are referred to herein as a "second mutation" or "second mutations". In certain embodiments, a third set of mutations that are used are mutations that can decrease binding affinity to the corresponding non-target TNFsf receptor and are referred to herein as a "third mutation" or "third mutations". In certain embodiments, bifunctional mutations that both increase binding affinity to the corresponding target TNFsf receptor while decreasing binding affinity to the corresponding non-target TNFsf receptor are used. In certain embodiments, other bifunctional mutations that reduce or essentially eliminate binding to both the corresponding target TNFsf receptor and the corresponding non-target TNFsfreceptor are used. Examples of such bifunctional "blocking mutations" for both a target and a non-target receptor include, but are not limited to, human TNF S175Y or L151R mutations that reduce binding to both TNFR1 and TNFR2 (Table 4). Blocking, second, third, and bifunctional mutations include, but are not limited to, certain mutations or sets of mutations identified in Table 4.

In certain embodiments, the single chain TNFsf ligands (scTNFsfL) provided herein comprise three operably linked TNFsf ligand monomers, where all three monomers are mutated, where one or two of the three monomers contain blocking mutations, and where one or two of the three monomers contain mutations that increase binding affinity for the target TNFsf receptor. In certain embodiments, one, two or three of the monomers can also contain mutations that decrease binding affinity for the non-target TNFsf receptor. In certain embodiments, one, two or three of the monomers can also contain bifunctional mutations.

Figure 15A:
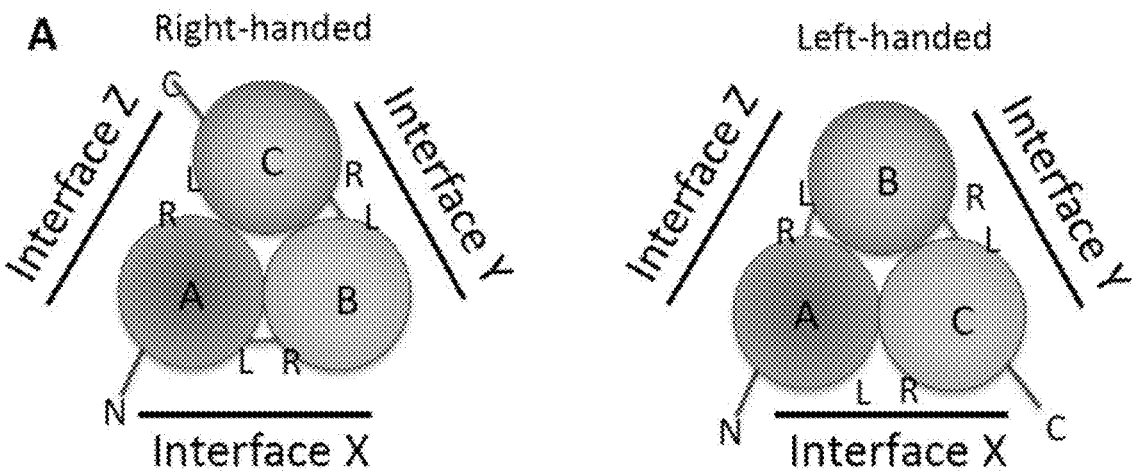
Figure 15B:
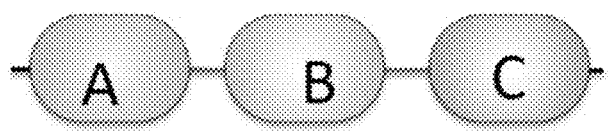
Figure 15C:
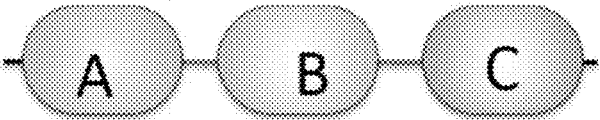

The binding site for the TNFsf receptor is formed by the interface formed by two adjacent monomers in a scTNFsfL as shown in FIG. 15, which depicts a scRANKL. In certain embodiments, it is desirable to have the blocking and high affinity mutations to be located on the same side of the binding groove. For example, TNFsf monomer AA', CD, and GH loops contribute to the side of the interface termed "L", and the TNFsf monomer DE and EF loops contribute to the side termed "R". Regardless of the orientation of folding (right- or left-handed) of the scTNFsfL, having these mutations occupy the same side of the cleft contributed by each monomer ensures that each interface can be individually mutated (FIG. 15) to provide for a folded scTNFsfL where one or two of the binding sites formed by the monomer interfaces are blocked (i.e., do not bind the target TNSsf receptor) and where one or two of the binding sites formed by the monomer interfaces have increased binding affinity for the target TNSsf receptor. In certain embodiments, this can be achieved by ordering the monomers in the scTNFsfL such that the monomer(s) having the blocking mutations in side "L" are located at the N-terminus of the scTNFsfL and the monomer(s) having mutations that increase binding affinity for the target receptor in side "L" are located at the C-terminus of the scTNFsfL. A non-limiting example of a useful ordering of monomers having blocking mutations and mutations that increase binding affinity for the target receptor is shown in FIG. 15C. In certain embodiments, it is also possible to incorporate mutations that decrease binding affinity for the non-target TNFsf receptor into one, two, or three of the binding interfaces. One illustrative example is provided in FIG. 15 for a scRANKL, where three mutations that increase binding affinity for the target receptor (K194E, F269Y, and H270Y) are on the same side of the interface as the blocking mutation (i.e., side "L" in FIG. 15). In this case a bifunctional mutation (Q236H) that decreases binding affinity for the non target TNFsf receptor (e.g., OPG), is located on the other side of the binding interface (i.e., side "R" in FIG. 15) and can equally participate in the formation of a blocking or a high affinity interaction with the target TNFsf receptor (e.g., RANK) when placed in all three monomers of the scTNFsfL.

The TNFsf ligand monomers containing the mutations can be operably linked in the scTNFsfL with peptide linkers. Such peptide linkers are typically of a length and flexibility that provides for folding of the scTNFsfL to form a trimer with a binding site formed by the monomer interfaces. In certain embodiments, the peptide linker can comprise or consist of one, two, or three, four, five or more "Gly-Gly-Ser-Gly" (SEQ ID NO: 38) units. Other useful peptide linkers that can be used include, but are not limited to: (i) [Gly-Ser]x linkers where x=2-10; (ii) one, two, or three, four, five or more "Gly-Gly-Gly-Ser" (SEQ ID NO: 39) units; (iii) one, two, or three, four, five or more "Gly-Gly-Gly-Gly-Ser" (SEQ ID NO: 40) units; (iv) one, two, or three, four, five or more "Ser-Glu-Gly" units; (v) one, two, or three, four, five or more "Gly-Ser-Ala-Thr" (SEQ ID NO: 41) units; and (vi) any combination of (i)-(v) and/or of one, two, or three, four, five or more "Gly-Gly-Ser-Gly" (SEQ ID NO: 38) units. Without seeking to be limited by theory, it is believed that relatively short peptide linkers of about 4 to about 12 amino acids that include, but not limited to those described above, can provide for recovery of scTNFsfL that preferentially fold in a left-handed configuration (FIG. 15A). Such preferential folding can be desirable in providing for more homogenous populations of scTNFsfL for use in methods of treating subjects suffering from various afflictions and related compositions. Such preferential folding can also be desirable in providing for localization of the desired combinations of blocking mutations, mutations that increase affinity for a target TNFsf receptor, mutations that decrease affinity for a non-target TNFsf receptor in different binding interfaces, and bifunctional mutations (e.g., as shown in FIG. 15).

Figure 2A:
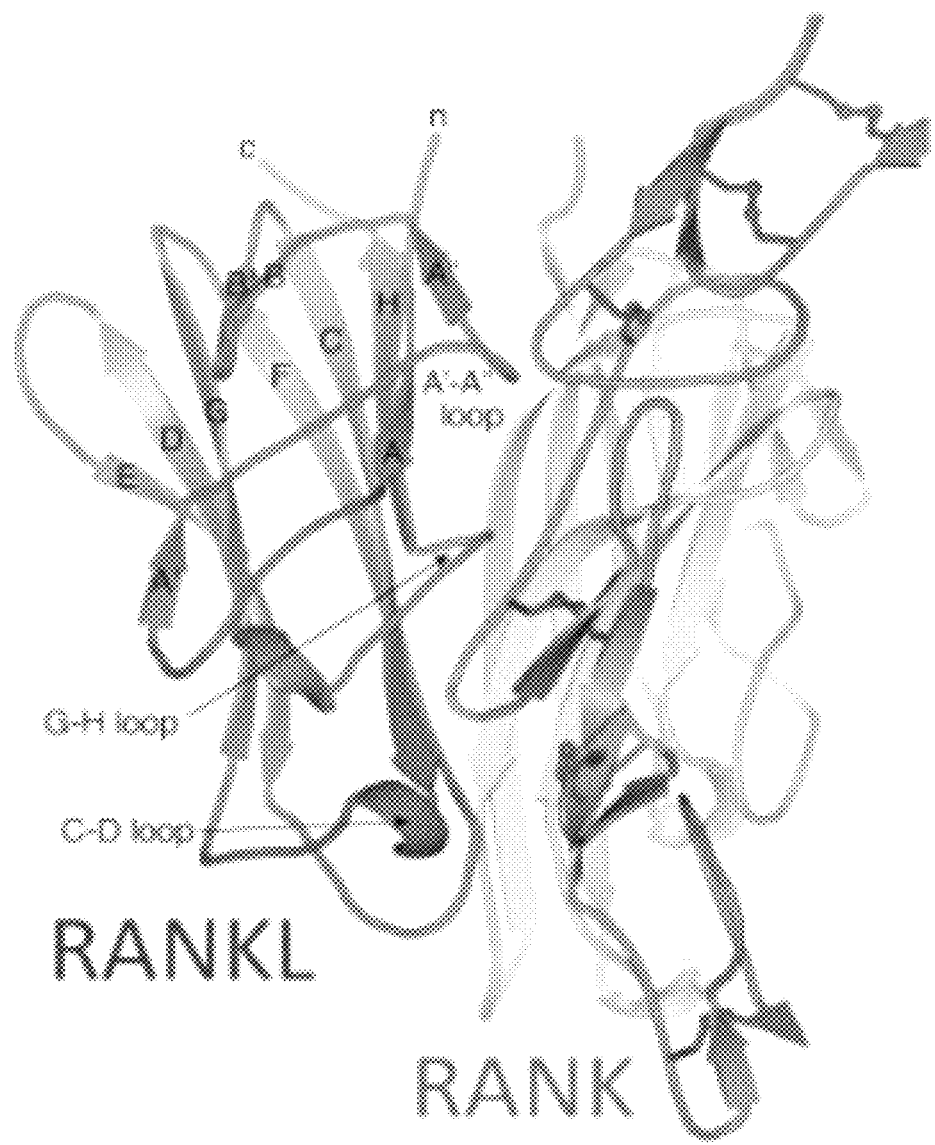
Figure 16:
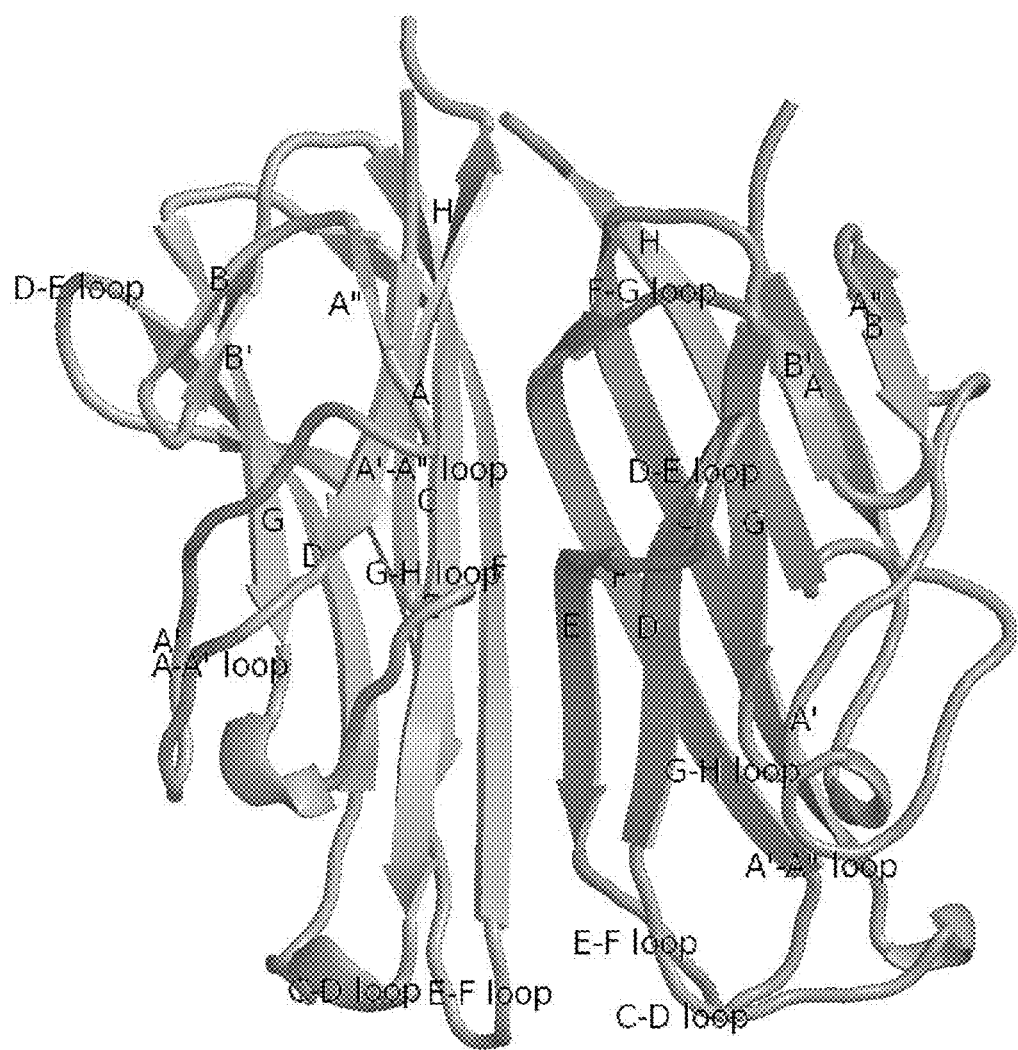

In certain embodiments, one or more mutations used in the scTNFsfL can be obtained by rational design where one or more residues in structural motifs that have been shown to interact with the target TNFsf receptor are mutated. Structural features common to TNFsf ligands that have been shown to participate in target and non-target receptor binding and that can be targeted for mutagenesis include the AA" Loop, BC loop, C-terminal half of the C strand, CD Loop, D strand, DE loop, E strand, EF loop, N-terminal half of the F strand, FG loop, and GH loop. Structural studies that detail specific regions and residues in TNFsf ligand interactions with target receptors include, but are not limited to, studies of RANKL and RANK (8, 9, 10, 11); studies of TNF and TNFR1 (29, 30, 31); and studies of TRAIL (Gasparian et al., *Apoptosis* 2009, 14, 778-787.; Kelley, et al., *J Biol Chem* 2005, 280, 2205-2212; MacFarlane, et al., *Cancer Res* 2005, 65, 11265-11270; Tur, et al., *J Biol Chem* 2008, 283, 20560-20568; Reis et al., *Cell Death Dis*, 1, e83; van der Sloot, et al., *Proc NatlAcad Sci USA* 2006, 103, 8634-8639; U.S. Pat. No. 6,740,739). Table 2 provides a non-limiting listing of structural features that can be mutated to provide for blocking mutations, second mutations, third mutations, or bifunctional mutations. Pictorial depictions of these features for RANKL are also provided in FIGS. 2A and 16.

TABLE 2

Structural features of TNFsf monomers that participate in target and non-target receptor binding

| TNFsf Feature | Human RANKL (SEQ ID NO: 2) Residue Numbers | Human TNF (SEQ ID NO: 4) Residue Numbers |
|---|---|---|
| AA" Loop | 170-195 (INATDIPSGSHKVSLSSWYHDRGWAK) | 95-112 (NPQAEGQLQWLNRRANAL) |
| BC loop | 210-213 (QDGF) | 129-132 (EGLY) |
| C-terminal half of C strand | 219-224 (NICFRH) | 137-142 (QVLFKG) |
| CD Loop | 225-235 (HETSGDLATEY) | 143-151 (QGCPSTHVLL) |
| D | 237-244 (QLMVYVTK) | 152-159 (LTHTISRI) |
| DE loop | 245-253 (TSIKIPSSH) | 160-164 (AVSYQ) |
| E | 254-260 (TLMKGGS) | 165-173 (TKVNLLSAI) |
| EF loop | 261-270 (TKYWSGNSEF) | 174-190 (KSPCQRETPEGAEAKPW) |
| N-terminal half of F | 271-276 (HFYSIN) | 191-194 (YEPI) |
| FG loop | 283-288 (LRSGEE) | 202-207 (LEKGDR) |
| GH loop | 296-306 (PSLLDPDQDAT) | 218-227 (LDFAESGQVY) |

| TNFsf Feature | Human TRAIL (SEQ ID NO: 6) Residue Numbers |
|---|---|
| AA" Loop | 125-163 (HITGTRGRSNTLSSPNSKNEKALGRKINSWESSRSGHSF) |
| BC loop | 178-181 (EKGF) |
| C-terminal half of C | 186-192 (SQTYFRF) |
| CD Loop | 193-205 (QEEIKENTKNDKQ) |
| D | 206-212 (MVQYIYK) |
| DE loop | 213-219 (YTSYPDP) |
| E | 220-227 (ILLMKSAR) |
| EF loop | 228-236 (NSCWSKDAE) |
| N-terminal half of F | 237-242 (YGLYSI) |
| FG loop | 249-254 (ELKEND) |
| GH loop | 262-274 (NEHLIDMDHEASF) |

Table 3 provides references for the atomic coordinates for RANKL, TNF, TRAIL, their corresponding target receptors, and their corresponding non-target receptors that establish the three-dimensional structures for those molecules. These coordinates can be downloaded from the National Center for Biotechnology Information (NCBI) database on the world-wide web at "ncbi.nlm.nih.gov/pubmed" using the PDB ID provided in Table 3. Structural features described in Table 2 are provided in the structures obtainable from these coordinates. Such three dimensional structures can also be used in the rational design of blocking, affinity increasing, affinity decreasing, and bifunctional mutations that can be used in the scTNFsfL provided herein.

TABLE 3

Structures of TNFsf Ligands target receptors, and non-target receptors.

| TNFsf Ligand | Target Receptor | Non-Target Receptor | NCBI PDB ID | Reference |
|---|---|---|---|---|
| Mouse RANKL | | | 1JTZ | Lam, J., Nelson, C. A., Ross, F. P., Teitelbaum, S. L., Fremont, D. H. Journal: (2001) J. Clin. Invest. 108: 971-979 |
| Mouse RANKL | | | 1S55 | To be published |

TABLE 3-continued

Structures of TNFsf Ligands target receptors, and non-target receptors.

| TNFsf Ligand | Target Receptor | Non-Target Receptor | NCBI PDB ID | Reference |
|---|---|---|---|---|
| Mouse RANKL | | | 1IQA | Ito, S., Wakabayashi, K., Ubukata, O., Hayashi, S., Okada, F., Hata, T. Journal: (2002) J. Biol. Chem. 277: 6631-6636 |
| | Mouse RANK | | 3ME4 | Liu, C., Walter, T. S., Huang, P., Zhang, S., Zhu, X., Wu, Y., Wedderburn, L. R., Tang, P., Owens, R. J., Stuart, D. I., Ren, J., Gao, B. Journal: (2010) J. Immunol. |
| Mouse RANKL | Mouse RANK | | 4GIQ | Nelson, C. A., Warren, J. T., Wang, M. W., Teitelbaum, S. L., Fremont, D. H. Journal: (2012) Structure 20: 1971-198 |
| Mouse RANKL | Mouse RANK | | 3QBQ | Ta, H. M., Nguyen, G. T. T., Jin, H. M., Choi, J. K., Park, H., Kim, N. S., Hwang, H. Y., Kim, K. K. Journal: (2010) Proc. Natl. Acad. Sci. USA 107: 20281-20286 |
| Mouse RANKL | Mouse RANK | | 3ME2 | Liu, C., Walter, T. S., Huang, P., Zhang, S., Zhu, X., Wu, Y., Wedderburn, L. R., Tang, P., Owens, R. J., Stuart, D. I., Ren, J., Gao, B. Journal: (2010) J. Immunol. |
| Mouse RANKL | | Mouse OPG | 4E4D | , J. T., Wang, M. W., Teitelbaum, S. L., Fremont, D. H. Journal: (2012) Structure 20: 1971-198 |
| Human RANKL | | Human OPG | 3URF | Luan, X. D., Lu, Q. Y., Jiang, Y. N., Zhang, S. Y., Wang, Q., Yuan, H. H., Zhao, W. M., Wang, J. W., Wang, X. Q. Journal: (2012) J. Immunol. 189: 245-252 |
| Mouse TNF | | | 2TNF | Baeyens, K. J., De Bondt, H. L., Raeymaekers, A., Fiers, W., De Ranter, C. J. Journal: (1999) Acta Crystallogr., Sect. D 55: 772-778 |
| Human TNF | | | 1TNF | Eck, M. J., Sprang, S. R. Journal: (1989) J. Biol. Chem. 264: 17595-17605 |
| Human TNF | | Human TNFR2 | 3ALQ | Mukai, Y., Nakamura, T., Yoshikawa, M., Yoshioka, Y., Tsunoda, S. I., Nakagawa, S., Yamagata, Y., Tsutsumi, Y. Journal: (2010) Sci. Signal. 3: ra83-ra83 |
| | Human TNFR1 | | 1TNR | Banner, D. W., D'Arcy, A., Janes, W., Gentz, R., Schoenfeld, H. J., Broger, C., Loetscher, H., Lesslauer, W. Journal: (1993) Cell(Cambridge, Mass.) 73: 431-445 |
| Human TRAIL | | | 1DG6 | Hymowitz, S. G., O'Connell, M. P., Ultsch, M. H., Hurst, A., Totpal, K., Ashkenazi, A., de Vos, A. M., Kelley, R. F. Journal: (2000) Biochemistry 39: 633-650 |
| Human TRAIL | | | 1D2Q | Cha, S. S., Kim, M. S., Choi, Y. H., Sung, B. J., Shin, N. K., Shin, H. C., ung, Y. C., Oh, B. H. Journal: (1999) Immunity 11: 253-261 |
| Human TRAIL | Human DR5 | | 1D4V | Mongkolsapaya, J., Grimes, J. M., Chen, N., Xu, X. N., Stuart, D. I., Jones, E. Y., Screaton, G. R. Journal: (1999) Nat. Struct. Biol. 6: 1048-1053 |
| Human TRAIL | Human DR5 | | 1D0G | Hymowitz, S. G., Christinger, H. W., Fuh, G., Ultsch, M., O'Connell, M., Kelley, R. F., Ashkenazi, A., de Vos, A. M. Journal: (1999) Mol. Cell 4: 563-571 |
| Human TRAIL | Human DR5 | | 1DU3 | Cha, S. -S., Sung, B. -J., Kim, Y. A., Song, Y. L., Kim, H. J., Kim, S., Lee, M. S., Oh, B. -H. Journal: (2000) J. Biol. Chem. 275: 31171-31177 |

In certain embodiments, one or more of the mutations used in the scTNFsfL can be obtained from a previously described TNFsf mutant or a TNFsf mutant provided herein. In certain embodiments, previously and/or instantly described blocking mutations and mutations that increase binding affinity for a target TNFsf receptor can be combined in the scTNFsfL via the methods provided herein to generate effective inhibitors of a given target TNFsf receptor. In certain embodiments, previously and/or instantly described blocking mutations, mutations that increase binding affinity for a target TNFsf receptor, and mutations that decrease binding affinity for a non-target receptor can be combined in the scTNFsfL via the methods provided herein to generate effective inhibitors of a given target TNFsf receptor that have reduced or negligible agonist activity for the non-target TNFsf receptor. In certain embodiments, previously and/or instantly described blocking mutations and bifunctional mutations that decrease binding affinity for a non-target receptor can be combined in the scTNFsfL via the methods provided herein to generate effective inhibitors of a given target TNFsf receptor that have reduced or negligible agonist activity for the non-target TNFsf receptor. Examples of various combinations of previously and/or instantly described blocking mutations, mutations that increase binding affinity for a target TNFsf receptor, mutations that decrease binding affinity for a non-target receptor, and bifunctional mutations include, but are not limited to, those provided in the following table for various scRANKL, scTNF, and scTRAIL.

TABLE 4

Combinations of first blocking mutations, mutations that increase binding affinity for the target receptor, mutations that decrease binding affinity for the non-target receptor, bifunctional mutations that decrease binding affinity for the target receptor and decrease binding affinity for the non-target receptor, and bifunctional mutations that both increase binding affinity for the target receptor and decrease binding affinity for the non-target receptor.

| TNFsf Member (SEQ ID NO:; NCBI) Mouse RANKL (NP_035743.2) | Target (T) and Non-Target (NT) Receptors Mouse RANK (T) OPG (NT) | | First mutations that reduce (or block) binding of a TNFsf member to its corresponding target receptor | Second mutations that increase binding of a TNFsf member to its corresponding target receptor | Third mutations that reduce (or block) binding of a TNFsf member to its corresponding non-target receptor | Reference for Mutation |
|---|---|---|---|---|---|---|
| | Set 1 | | H224N and I248R (U.S. Pat. No. 7,399,829) | A171R (U.S. Pat. No. 7,399,829) | G191A (U.S. Pat. No. 7,399,829) | U.S. Pat. No. 7,399,829, and FIGS. 29 and Table 2 disclosed therein. |
| | Set 2 | | CDins² (an insertion of GGS after R222 in strand C, yielding FR-GGS-HHET; SEQ ID NO: 44) | K194E, F269Y, H270Y, and combinations thereof.[1] Also Q236H.[1] | K194E, F269Y, H270Y, and combinations thereof.[1] Also Q236H[1]. | FIG. 3, 4, 7 |
| | Set 3 | | CDins (an insertion of GGS after R222 in strand C, yielding FR-GGS-HHET SEQ ID NO: 44) | Q236H[1] | Q236H[1] | FIG. 3, 4, 7 |
| | Set 4 | | R222Q, or R222A, or R222Y, at the end of strand C | K194E, F269Y, H270Y, and combinations thereof. Also Q236H[1] | Q236H[1] | FIG. 3, 4, 7 |
| | Set 5 | | Swap of AA" loop residues SGSHKVSLS for SSS after P175. (Lam et al.) | Q236T[1] (U.S. Pat. No. 7,399,829) | Q236T[1] | See FIG. 4 of Lam et al., 2001, 7(108); 971-979. U.S. Pat. No. 7,399,829 and Table 2 disclosed therein. |
| Human RANKL (SEQ ID NO: 2) | Human RANK (T) OPG (NT) | | First mutations that reduce (or block) binding of a TNFsf member to its corresponding target receptor | Second mutations that increase binding of a TNFsf member to its corresponding target receptor | Third mutations that reduce (or block) binding of a TNFsf member to its corresponding non-target receptor | |
| | Set 6 | | H225N and I249R (U.S. Pat. No. 7,399,829) | A172R (U.S. Pat. No. 7,399,829) | G192A (U.S. Pat. No. 7,399,829) | U.S. Pat. No. 7,399,829, and FIGS. 29 and Table 2 disclosed therein. |
| | Set 7 | | CDins (an insertion of GGS after R223 in in strand C, yielding FR-GGS-HHET; SEQ ID NO: 44) | K195E, F270Y, H271Y, and combinations thereof.[1] Also Q237H.[1] | K195E, F270Y, H271Y, and combinations thereof.[1] Also Q237H.[1] | FIG. 3, 4, 7 |
| | Set 8 | | CDins (an insertion of GGS after R223 in in | Q237H[1] | Q237H[1] | FIG. 3, 4, 7 |

TABLE 4-continued

Combinations of first blocking mutations, mutations that increase binding affinity for the target receptor, mutations that decrease binding affinity for the non-target receptor, bifunctional mutations that decrease binding affinity for the target receptor and decrease binding affinity for the non-target receptor, and bifunctional mutations that both increase binding affinity for the target receptor and decrease binding affinity for the non-target receptor.

| | | strand C, yielding FR-GGS-HHET; SEQ ID NO: 44), and also Q237H | | | |
|---|---|---|---|---|---|
| | Set 9 | R223Q, or R223A, or R223Y, at the end of strand C. Also Q237H | K195E, F270Y, H271Y, and combinations thereof. Also Q237H.[1] | Q237H[1] | FIG. 3, 4, 7 |
| | Set 10 | Swap of AA" loop residues SGSHKVSLS for SSS after P176. (Lam et al.) | Q237T[1] (U.S. Pat. No. 7,399,829) | Q237T[1] | Lam et al., Crystal structure of the TRANCE/RANKL cytokine reveals determinants of receptor-ligand specificity; Journal of Clinical Investigation 2001, 7(108); 971-979. U.S. Pat. No. 7,399,829 on Jul. 15, 2008. and Table 2 disclosed therein. |

| Mouse TNFα (NP_038721.1) | TNFR1 (T) TNFR2 (NT) | First mutations that reduce (or block) binding of a TNFsf member to its corresponding target receptor | Second mutations that increase binding of a TNFsf member to its corresponding target receptor | Third mutations that reduce (or block) binding of a TNFsf member to its corresponding non-target receptor | |
|---|---|---|---|---|---|
| | Set 11 | Y165Q, or Y165G, or Y165L, or Y165K, or Y165T. (Loetscher et al.) | S164T[1] (Loetscher et al.) | S164T[1] | See Table 1 of Loetscher et al., Journal of Biological Chemistry 1993, 35(268): 26350-26357. |
| | Set 12 | D221V (Loetscher et al.) | L108T and R111F[1] (Mukai et al.) | L108T and R111F[1] | (8) See mutant R1-5 in Tables 1 and 2 of Mukai et al., Journal of Molecular Biology 2009, (386): 1221-1229. |
| | Set 13 | S177Y or L153R (Loetscher et al.) | A162T, I163P, S164A, Y165I, Q166N, and E167R.[1] (mutant T8, Shibata et al.) | A162T, I163P, S164A, Y165I, Q166N, and E167R.[1] (Shibata et al.) | See mutant T8 in Table 2 of Shibata et al., Journal of Biological Chemistry 2008, 2(283): 998-1007. |
| | Set 14 | N113Q (Loetscher et al.) | L108Q and R111W[1] (mutant R1-2, Mukai et al.) | L108Q and R111W[1] | |
| | Set 15 | Y165Q, Y165G, Y165L, Y165K, or Y165T (Loetscher et al.). | A162T, I163T, S164A, Q166S, and E167G.[1] (mutant R1-11, Mukai et al.) | A162T, I163T, S164A, Q166S, and E167G.[1] | |

| | | First mutations that reduce (or block) binding of a TNFsf member to its | Second mutations that increase binding of a TNFsf member to its corresponding | Third mutations that reduce (or block) binding of a TNFsf member to its corresponding | |
|---|---|---|---|---|---|

TABLE 4-continued

Combinations of first blocking mutations, mutations that increase binding affinity for the target receptor, mutations that decrease binding affinity for the non-target receptor, bifunctional mutations that decrease binding affinity for the target receptor and decrease binding affinity for the non-target receptor, and bifunctional mutations that both increase binding affinity for the target receptor and decrease binding affinity for the non-target receptor.

| Human TNF (SEQ ID NO: 4) | TNFR1 (T) TNFR2 (NT) | corresponding target receptor | target receptor | non-target receptor | Comments |
|---|---|---|---|---|---|
| | Set 16 | Y163Q, or Y163G, or Y163L, or Y163K, or Y163T. | S162T[1] | S162T[1] | |
| | Set 17 | D219V | L105T and R108F[1] | L105T and R108F[1] | |
| | Set 18 | S175Y or L151R[1] | A160T, V161S, S162V, Q164P, and T165H. | S175Y or L151R[1] | |
| | Set 19 | N110Q | L105T, R108F, and E222T[1] | L105T, R108F, and E222T[1] | |
| | Set 20 | Y163Q, or Y163G, or Y163L, or Y163K, or Y163T. | A160T, V161T, S162A, Q164S, and T165G.[1] | A160T, V161T, S162A, Q164S, and T165G.[1] | |
| Mouse Trail (SEQ ID NO: 5) | DR5 (T) DR4, DcR1, DcR2, and OPG (NT) | First mutations that reduce (or block) binding of a TNFsf member to its corresponding target receptor | Second mutations that increase binding of a TNFsf member to its corresponding target receptor | Third mutations that reduce (or block) binding of a TNFsf member to its corresponding non-target receptor | |
| | Set 21 | Y193A, Q197S, S199V, M205R, Y223W, and S225D. (Gasparian et al) | D279H[1] (Gasparian et al) | D279H[1] | See Table 2 of Gasparian et al, Apoptosis 2009, (14): 778-787. |
| Mouse Trail (SEQ ID NO: 5) | DR4 (T) DR5, DcR1, DcR2, and OPG (NT) | First mutations that reduce (or block) binding of a TNFsf member to its corresponding target receptor | Second mutations that increase binding of a TNFsf member to its corresponding target receptor | Third mutations that reduce (or block) binding of a TNFsf member to its corresponding non-target receptor | |
| | Set 22 | Y193N, R195K, Q197R, H274R, M276L, and D277Q. (mutant DR5-8, Gasparian et al.) | Q149I, K163R, M205R, K208H, and S225D. (mutant 4C7, Reis et al.) | Y193N, R195K, Q197R, H274R, M276L, and D277Q. | See Table 1 Reis et al., Cell Death and Disease 2010, 1, e83. |
| Human Trail (NP_003801.1) | DR5(T) DR4, DcR1, DcR2 and OPG (NT) | First mutations that reduce (or block) binding of a TNFsf member to its corresponding target receptor | Second mutations that increase binding of a TNFsf member to its corresponding target receptor | Third mutations that reduce (or block) binding of a TNFsf member to its corresponding non-target receptor | |

TABLE 4-continued

Combinations of first blocking mutations, mutations that increase binding affinity for the target receptor, mutations that decrease binding affinity for the non-target receptor, bifunctional mutations that decrease binding affinity for the target receptor and decrease binding affinity for the non-target receptor, and bifunctional mutations that both increase binding affinity for the target receptor and decrease binding affinity for the non-target receptor.

| | | | | | |
|---|---|---|---|---|---|
| | Set 23 | Y189A, Q193S, N199V, K201R, Y213W, and S215D. | D269H[1] | D269H[1] | |
| Human Trail (NP_003801.1) | DR4(T) DR5, DcR1, DcR2, and OPG (NT) | First mutations that reduce (or block) binding of a TNFsf member to its corresponding target receptor | Second mutations that increase binding of a TNFsf member to its corresponding target receptor | Third mutations that reduce (or block) binding of a TNFsf member to its corresponding non-target receptor | |
| | Set 24 | Y189N, R191K, Q193R, H264R, I266L, and D267Q. (mutant DR5-8) | G131R, R149I, S159R, N199R, K201H, and S215D. | Y189N, R191K, Q193R, H264R, I266L, and D267Q. | |
| Human APRIL (NP_742085) | TACI (T); BCMA (NT) | First mutations that reduce (or block) binding of a TNFsf member to its corresponding target receptor | Second mutations that increase binding of a TNFsf member to its corresponding target receptor | Third mutations that reduce (or block) binding of a TNFsf member to its corresponding non-target receptor | |
| | Set 25 | R206E | R206M | R206M | US20140178329 |

[1] Bifunctional mutations.
[2] "CDins" refers to an insertion of GGS after R222 in strand C, yielding FR-GGS-HHET (SEQ ID NO: 44) that displaces residues out into the CD loop.

In certain embodiments, one or more of the mutations used in the scTNFsfL can be obtained by a screening assay where TNFsf monomers with desired blocking, second, third, or bifunctional mutations are selected. In certain embodiments, such screening assays can comprise use of a phage, yeast, or other display library comprising a mutagenized population of TNFsf monomers. Such libraries are then screened for the absence or presence of binding to a target TNFsf receptor or, in certain instances, reduced binding to a non-target TNFsf receptor. Binding to target or non-target receptors can be detected through use of either detectably labelled receptors or label-free receptor binding assays. In certain embodiments, TNFsfL with blocking mutations can be identified by screening and selecting for mutations that exhibit reduced binding to the corresponding target receptor. In certain embodiments, TNFsfL with bifunctional blocking mutations that exhibit both reduced binding to the corresponding target receptor and the non-target receptor by either simultaneously or sequentially screening for mutant ligands that exhibit reduced binding to both the corresponding target receptor and the non-target receptor. In certain embodiments, bifunctional mutations that exhibit both increased binding affinity for the corresponding target TNFsf receptor and decreased binding affinity for the corresponding non-target TNFsf receptor can be identified by screening and selecting for mutant TNFsf ligands that exhibit binding to limiting amounts of the target TNFsf receptor in the presence of a TNFsf non-target receptor. In certain embodiments, screening and selecting for mutant TNFsf ligands that exhibit binding to limiting amounts of the target TNFsf receptor in the presence of a TNFsf non-target receptor can be achieved by presenting a labelled target TNFsf receptor in the presence of at least an equimolar or molar excess of an unlabeled non-target receptor. Methods of screening and selecting for TNFsf ligand mutations that provided desired binding properties are disclosed both herein (e.g., in Example 9) and elsewhere.

The scTNFsfL provided herewith can also further comprise additional mutations that confer other desirable properties. In certain embodiments, the TNFsf monomers used in the scTNFsfL can comprise mutations that improve solubility. Examples of mutations that improve solubility of RANKL monomers and scRANKL provided herein include, but are not limited to, I247Q, I247E, I247K, I247R, and C221S in human RANKL (SEQ ID NO:2). In certain embodiments, the TNFsf monomers used in the scTNFsfL can comprise mutations reduce or eliminate O-linked glycosylation sites by substituting or deleting one or more serine or threonine residues at such sites. In certain embodiments, the TNFsf monomers used in the scTNFsfL can comprise mutations reduce or eliminate N-linked glycosylation sites by substituting, deleting, or otherwise disrupting one or more of such sites. N-linked glycosylation sites will typically comprise the sequence N—X—Y, where N is asparagine, X is any amino acid other than proline, and Y is threonine, serine, or cysteine.

The scTNFsfL provided herein can also be covalently modified. Covalent modifications to the scTNFsfL include, but are not limited to, linkages to polyethylene glycol ("PEG"), polypropylene glycol, and/or polyoxyalkylenes; the alkylation, lipidation, acetylation, and or acylation of one or more side-chains of amino acid residues; the acetylation of an N-terminus; and/or the amidation of a C-terminus. In certain embodiments, such covalent modifications can provide for improved stability, solubility, and/or reduced immunogenicity of the modified scTNFsfL. Such modifications of RANKL are described in U.S. Pat. No. 7,399,829, which is incorporated herein by reference in its entirety, and references disclosed in U.S. Pat. No. 7,399,829.

Non-limiting examples of scTNFsfL provided herein include scRANKL, scTNFL, and scTRAIL. In certain embodiments, the scRANKL is selected from the group consisting of SEQ ID NO: 13, 14, 15, 16, and derivatives thereof. In this context, derivatives of the scRANKL can include, but are not limited to, any of: (i) any of the aforementioned additional mutations that confer other desirable properties or covalent modifications thereof; (ii) a scRANKL having at least 85%, 90%, 95%, 96%, 98%, or 99.5% sequence identity across the entire length of SEQ ID NO: 13, 14, 15, 16 or across the entire length of any of the mutated RANKL monomers contained in SEQ ID NO:13, 14, 15, 16; and (iii) a scRANKL having any of the mutated RANKL monomers contained therein and a different peptide linker or a monomer having at least 85%, 90%, 95%, 96%, 98%, 99.5%, or 100% sequence identity across the entire length of those monomers and a different peptide linker. In certain embodiments, the scTNFL is selected from the group consisting of SEQ ID NO:17, 18, 19, 20, 21, 22, and derivatives thereof. In this context, derivatives of the scTNFL can include, but are not limited to, any of: (i) any of the aforementioned additional mutations that confer other desirable properties or covalent modifications thereof; (ii) a scTNFL having at least 85%, 90%, 95%, 96%, 98%, 99.5%, or 100% sequence identity across the entire length of SEQ ID NO:17, 18, 19, 20, 21, or 22, or across the entire length of any of the mutated TNFL monomers contained therein; and (iii) a scTNFL having any of the mutated TNFL monomers contained in SEQ ID NO:17, 18, 19, 20, 21, or 22 and a different peptide linker or a monomer having at least 85%, 90%, 95%, 96%, 98%, 99.5% sequence identity across the entire length of those monomers and a different peptide linker. In certain embodiments, the scTRAIL is selected from the group consisting of SEQ ID NO:23, 24, 42, 43, and derivatives thereof. In this context, derivatives of the scTRAIL can include, but are not limited to, any of: (i) any of the aforementioned additional mutations that confer other desirable properties or covalent modifications thereof; (ii) a scTRAIL having at least 85%, 90%, 95%, 96%, 98%, 99.5%, or 100% sequence identity across the entire length of SEQ ID NO:23, 24, 42, or 43 or across the entire length of any of the mutated TRAIL monomers contained therein; and (iii) a scTRAIL having any of the mutated TRAIL monomers contained in SEQ ID NO:23, 24, 42, or 43 and a different peptide linker or a monomer having at least 85%, 90%, 95%, 96%, 98%, 99.5%, sequence identity across the entire length of those monomers and a different peptide linker. Variants of the RANKL, TNF, and TRAIL sequences provided herewith that can be used in the scRANKL, scTNF, and scTRAIL polypeptides provided herein also include allelic variants of RANK, TNF, and TRAIL monomers that can be accessed from the National Center for Biotechnology Information (NCBI) database on the worldwide web at "ncbi.nlm.nih.gov/pubmed" using the identifiers for those monomers provided in Table 5 and associated links.

The scTNFsfL provided herein can be produced in a transformed cell or organism containing a recombinant nucleic acid where a promoter active in that cell or organism is operably linked to a promoter. Such cells can be prokaryotic or eukaryotic cells (i.e. plant, yeast, fungal, insect, avian, or mammalian cells). Such organisms include, but are not limited to, plants or non-human animals. In certain embodiments, the nucleic acid encoding the scTNFsfL is operably linked to a promoter and a nucleic acid encoding a signal peptide and the scTNFsfL can be secreted from the transformed cell and recovered from the media in which the cell was grown. In other embodiments, the nucleic acid encoding the scTNFsfL is operably linked to a promoter and the scTNFsfL is recovered from the cell. Methods for expressing and recovering the TNFsf member RANKL in prokaryotic cells that can be used to express scRANKL, or adapted for use in expression of other scTNFsfL, are disclosed in U.S. Pat. No. 7,399,829, which is incorporated herein by reference in its entirety. In still other embodiments, the nucleic acid encoding the promoter and the scTNFsfL can be introduced into the genome of a transgenic animal and recovered from the milk of the transgenic animal (e.g., U.S. Pat. Nos. 5,741,957, 5,304,489, and 5,849,992). The scTNFsfL can be purified from the media or from cell lysates by the customary chromatography methods that include, but are not limited to, gel filtration, ion-exchange chromatography, hydrophobic interaction chromatography (HIC, chromatography over DEAE-cellulose or affinity chromatography).

Methods for inhibition of TNFsf receptors in a subject in need thereof by administering an effective amount of a scTNFsfL are also provided herein. The present disclosure also provides specific compositions suitable for such administration that contain scTNFsfL members that include, but are not limited to scRANKL, scTNFL, and scTRAIL, in a subject, including but not limited to, humans and animals. Animal subjects can include companion animals (e.g., cats and dogs) as well as other animals that include but are not limited to, cattle, horses, pigs, sheep, and the like. In certain embodiments, compositions aimed at the treatment of non-human animals, it is anticipated that scTNFsfL member would be derived from the subject animal to minimize immunogenicity of the scTNFsfL The dosage of scTNFsfL or composition comprising the same that is administered to a subject in need thereof may vary, depending on the reason for use and the individual subject. The dosage may be adjusted based on the subject's weight, the age and health of the subject, genotype, and tolerance for the compound or composition.

The amount of scTNFsfL or composition comprising the same to be used depends on many factors. Dosages may include about 0.1 mg/kg of bodyweight, 0.2 mg/kg of bodyweight, 0.5 mg/kg of bodyweight, 1 mg/kg of bodyweight, 2 mg/kg of bodyweight, about 5 mg/kg of bodyweight, about 10 mg/kg of bodyweight, about 15 mg/kg of bodyweight, about 20 mg/kg of bodyweight, about 25 mg/kg of bodyweight, about 30 mg/kg of bodyweight, about 40 mg/kg of bodyweight, about 50 mg/kg of bodyweight, about 60 mg/kg of bodyweight, about 70 mg/kg of bodyweight, about 80 mg/kg of bodyweight, about 90 mg/kg of bodyweight, or about 100 mg/kg of bodyweight. The scTNFsfL or composition comprising the same can be administered once or multiple times per day. The frequency of administration may vary from a single dose per day to multiple doses per day. Routes of administration of a scTNFsfL or composition comprising the same include oral, parenteral, by inhalation, or topical administration. The term parenteral as used herein includes intravenous, intraarterial, intraperitoneal, intramuscular, subcutaneous, rectal or vaginal administration. In certain embodiments, a form for administration can be a solution for injection, in particular for intravenous or intraarterial injection or drip. In certain embodiments, a suitable pharmaceutical composition for injection may comprise a buffer (e.g. acetate, phosphate or citrate buffer), a surfactant (e.g. polysorbate), optionally a stabilizer agent (e.g. human albumin), etc. However, the scTNFsfL or composition comprising the same can also be delivered directly to the site of the adverse cellular population thereby increasing the exposure of the diseased tissue to the scTNFsfL.

In certain embodiments, the effective amount of the scTNFsfL or composition comprising the same can be administered alone or in combination with one or more additional therapeutic agents (second therapeutic entity), regardless of the disease that said second therapeutic entity is administered to treat. In a combination therapy, the effective amount of the scTNFsfL or composition comprising the same may be administered before, during, or after commencing therapy with another agent, as well as any combination thereof, i.e., before and during, before and after, during and after, or before, during and after commencing the additional therapy.

In certain embodiments, the composition comprises the scTNFsfL. In yet another embodiment, the agent is a nucleic acid that comprises a promoter that is operably linked to a nucleic acid that encodes the scTNFsfL. Delivery methods for other nucleic acids encoding RANKL variants that can be adapted to the scTNFsfL provided herein include, but are not limited to, those described in U.S. Pat. No. 7,399,829, which is incorporated herein by reference in its entirety, and references disclosed in U.S. Pat. No. 7,399,829.

Methods of treating osteoporosis in a subject in need thereof by administering to the subject a therapeutically effective amount of a scRANKL polypeptide, a nucleic acid comprising a promoter that is operably linked to a nucleic acid encoding the scRANKL polypeptide, or compositions comprising the polypeptide or the nucleic acid are provided herein. In certain embodiments, subjects in need of such treatment can be identified by measuring bone mineral density and comparing the values obtained to either a previous measurement in the subject or known values for similar, healthy subjects. In certain embodiments, bone mineral density can be determined by dual x-ray absorptiometry (DXA), quantitative computed tomography (QCT), ultrasonography, single-energy x-ray absorptiometry (SXA), magnetic resonance imaging, radiography, and radiographic absorptiometry. Target subjects include, but are not limited to, postmenopausal woman, malnourished subjects, and others suffering from, or at risk for developing osteoporosis.

Methods for inhibiting bone resorption and/or osteoclastogenesis in a subject in need thereof by administering to the subject a therapeutically effective amount of a scRANKL polypeptide, a nucleic acid comprising a promoter that is operably linked to a nucleic acid encoding the scRANKL polypeptide, or compositions comprising the polypeptide or the nucleic acid are provided herein. Subjects in need thereof who exhibit excess bone resorption can suffers from the effects of hypercalcemia, have symptoms of hypercalcemia, or exhibit measurable hypercalcemia when compared to either a previous measurement in the subject or known values for similar, healthy subjects. In addition to regulating osteoclast activity, the methods described herein are applicable to inhibiting osteoclast activity, regulating osteoclast generation and inhibiting osteoclast generation in individuals inflicted with excess bone resorption. Osteoclastogenesis can be associated with disease conditions in which there is excess bone remodeling and include, but are not limited to, Paget's disease and cancer. Certain cancers that include, but are not limited to, breast cancer, multiple myeloma, melanomas, lung cancer, prostrate, hematologic, head and neck, and renal cancers, can metastasize to bone, induce bone breakdown by local disrupting normal bone remodeling, and can be associated with enhanced numbers of osteoclasts and enhanced amount of osteoclastic bone resorption resulting in hypercalcemia (US Pat. Appln. Pub. No. 20140178376).

Methods of treating rheumatoid arthritis, Crohn's disease, psoriasis, or inflammatory osteolysis in a subject in need thereof by administering to the subject a therapeutically effective amount of a composition comprising a scTNFL are also provided herein. Biologic TNF.alpha. antagonists, such as infliximab (Remicade®), golimumab (Simponi®), adalimumab (Humira®), and etanercept (Enbrel®) have been shown so far to be efficacious in treating rheumatoid arthritis (RA), psoriatic arthritis (PsA), Crohn's disease (CD), ulcerative colitis (UC), psoriasis, and ankylosing spondylitis (U.S. Pat. Appln. Pub. No. 20150184244). In certain embodiments, the scTNFL ligands provided herein can be used either in place of, or in concert with, those or other TNF antagonists to treat RA, PsA, CD, UC, psoriasis, and/or ankylosing spondylitis. Subjects in need thereof can be identified either by the presence of symptoms or by the presence of certain biomarkers (e.g., U.S. Pat. Appln. Pub. No. 20150184244). In certain embodiments, the scTNFL can preferentially inhibit TNFR1 and exhibit reduced or negligible inhibition of TNFR2 (or the TNFR2-triggered pathways), resulting in a reduction in undesirable side effects associated with TNF antagonists that non-selectively inhibit both TNFR1 and TNFR2. Anticipated reductions in side effects associated with certain scTNFL provided herein include, but are not limited to, reduced immune function resulting in increased susceptibility to infections. Methods of treating a DR5-positive cancer in a subject in need thereof by administering to the subject a therapeutically effective amount of the composition comprising a scTRAIL, either alone or in combination with exogenously added wild-type TRAIL, or also provided herein. In certain embodiments, the scTRAIL provided herein can induce apoptosis in cancer cells (e.g., DR5-positive cancer cells, DR5-positive cancer cells that over express or have higher levels of DR5 activity, and the like). It is contemplated that scTRAIL provided herein can be employed to treat cancer cells either in vivo or ex vivo. Ex vivo treatments can be used in bone marrow transplantation and particularly, autologous bone marrow transplantation. Ex vivo treatments described in U.S. Pat. No. 6,740,739, which is incorporated herein by reference in its entirety, can be adapted for use with the scTRAIL provided herein.

Methods of treating systemic lupus erythematosus (SLE) rheumatoid arthritis or multiple sclerosis in a subject in need thereof, comprising the step of administering to the subject a therapeutically effective amount of the aforementioned composition, wherein the TNFsf member is A proliferation inducing ligand (APRIL) are also provided herein. Certain inhibitors of TACI likely block both APRIL and BAFF signaling. Ataicicept (a TACI-Ig fusion protein) was found to be considerably safe and well tolerated in patients with rheumatoid arthritis, with some evidence of biological activity. But, primary endpoints were not met in Phase II trials (van Vollenhoven et al., 2011; Arthritis Rheum. 63(7):1782-

92). A more active inhibitor of this pathway could prove beneficial. Methods and APRIL mutants disclosed in US Patent Pub. 20140178329, which is incorporated herein by reference in its entirety, can be adapted for use in the methods and compositions involving scAPRIL that are provided herein.

EXAMPLES

Example 1. Identification of RANKL Mutants which do not Bind RANK

RANKL residues forming salt bridges or hydrogen bonds with RANK were targeted for site directed mutagenesis using the program PISA (European Bioinformatics Institute, Cambridgeshire, UK) and the RANK/RANKL co-crystal structure (9). Loops at the RANK/RANKL interface were disrupted by amino acid insertion. Mutations were introduced into the expression construct, pGEX-GST-RANKL, by PCR using Phusion polymerase (New England BioLabs, Ipswich, Mass.). After verification by nucleic acid sequencing, the mutant RANKL-encoding constructs were transformed into E. coli strain BL21-CodonPlus (DE3)-RIL competent cells (Agilent Technologies Inc., Santa Clara, Calif.) for protein production. Correctly-folded soluble protein was purified from cell lysate on glutathione sepharose (8). The mutant RANKL protein was released from the GST affinity tag by digestion with PreScission™ protease (GE Life Sciences, Piscataway, N.J.).

Example 2. Development of RANKL Variants

Figure 1C:
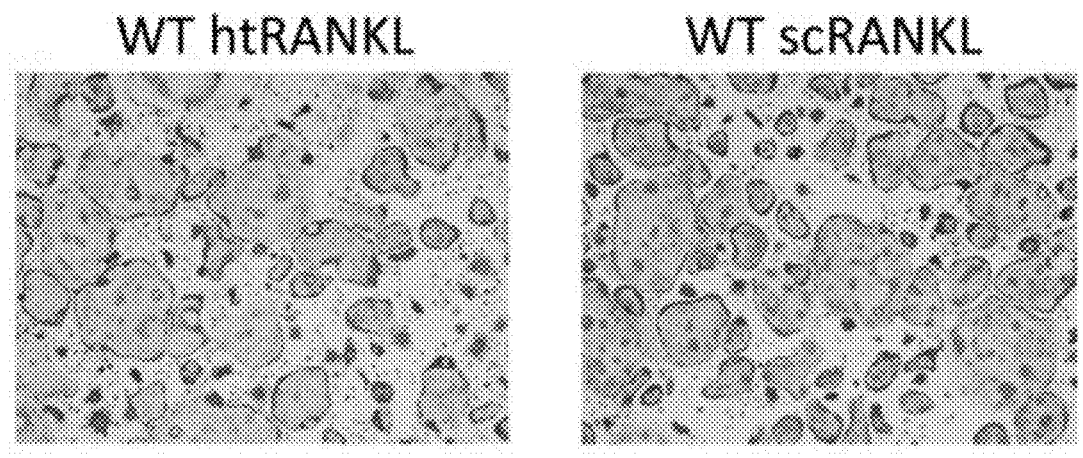

We covalently linked three RANKL monomers with two short glycine-rich linkers (FIG. 1A), which were modeled after previously reported single-chain versions of other TNF superfamily members (13-16). This version of RANKL encoded as a single-chain (scRANKL) protein enabled individual modification of the binding affinities of the three binding sites for RANK and OPG. We refer to the noncovalently linked, homotrimeric version of RANKL as "htRANKL." Two additional surface "solubility" mutations $Cys^{220} \rightarrow Ser$ and $Ile^{246} \rightarrow Glu$ (C220S/I246E), which do not affect the binding of the mutant RANKL to RANK or its function, were introduced to improve protein production (FIGS. 5, A and B). This version of RANKL is referred to as "WT-SM htRANKL." Therefore, all versions of htRANKL and scRANKL incorporate these two solubility mutations. As expected, no monomeric species of scRANKL was observable on a denaturing gel (FIG. 1B), and scRANKL migrated similarly to the trimeric species of chemically cross-linked wild-type htRANKL. To avoid potential discrepancies in molecular mass when comparing the cross-linked protein to the native protein, we more precisely determined the molecular masses of htRANKL and scRANKL by multi-angle light scattering (MALS) analysis. We found that scRANKL had a molecular mass consistent with that of three covalently linked RANKL monomers (FIG. 6A). Moreover, scRANKL induced bone marrow macrophages (BMMs) to undergo osteoclastogenesis as effectively as did the wild-type cytokine (FIG. 1C and FIG. 6B).

Figure 1D:
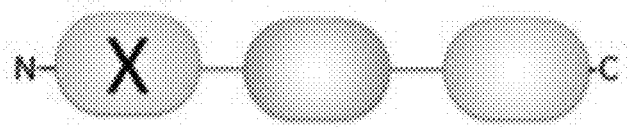
Figure 1D:
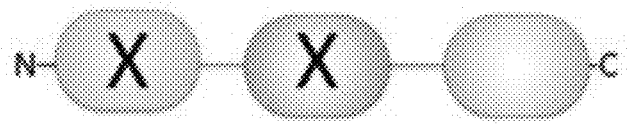
Figure 2B:
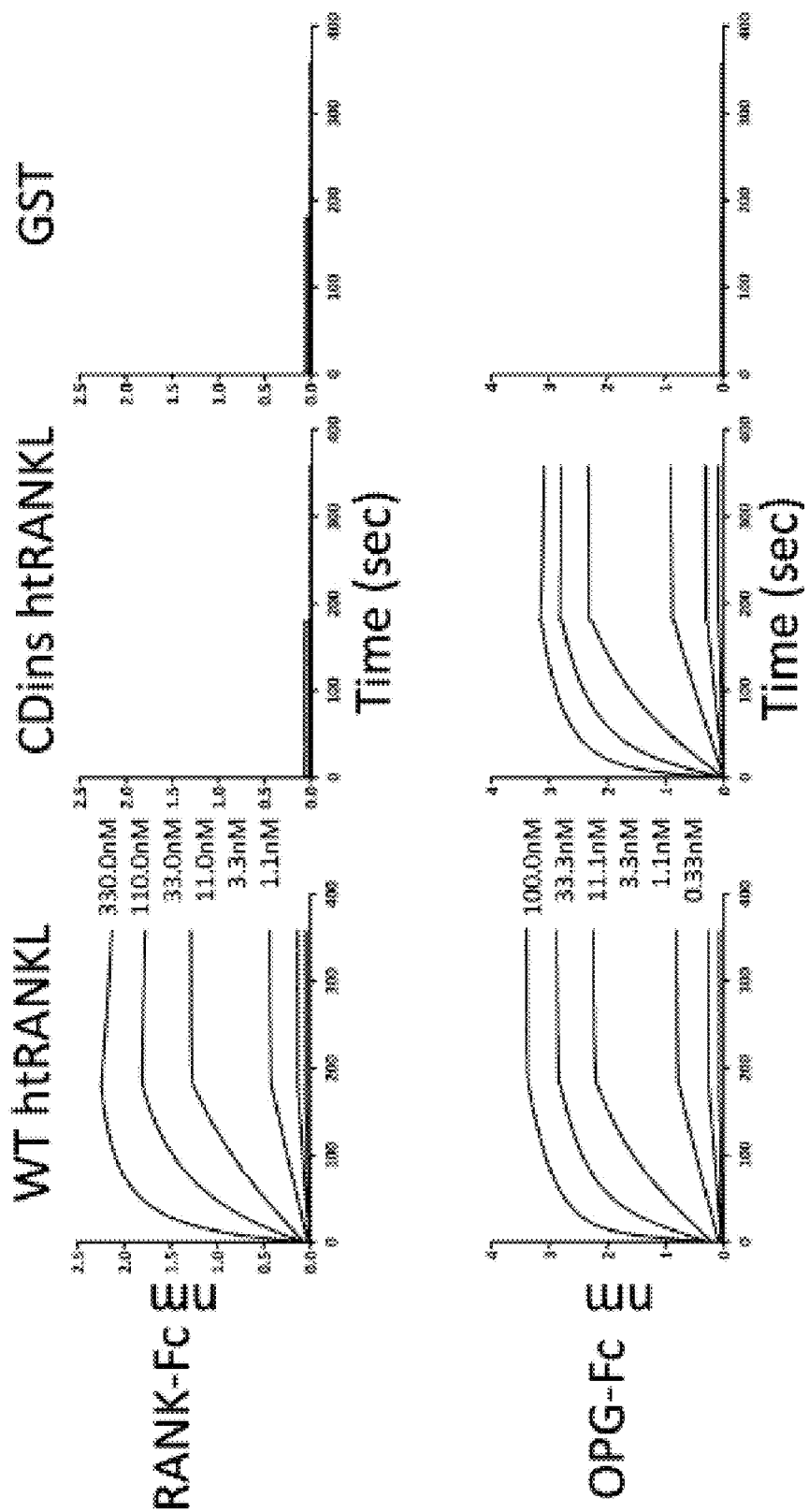
Figure 2C:
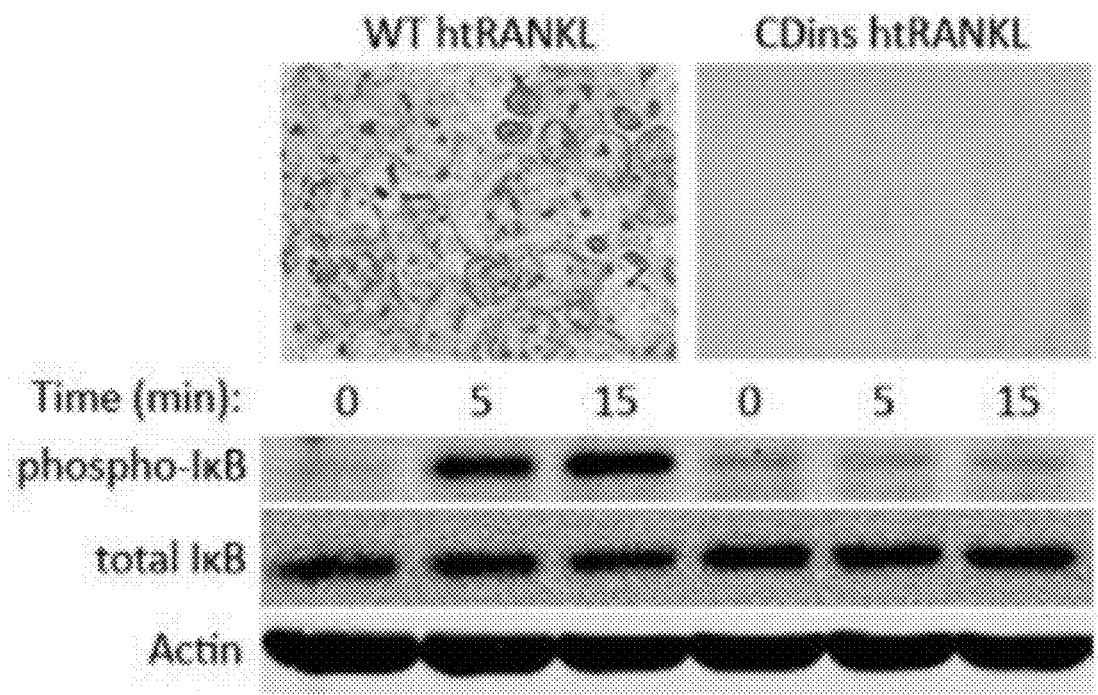
Figure 2D:
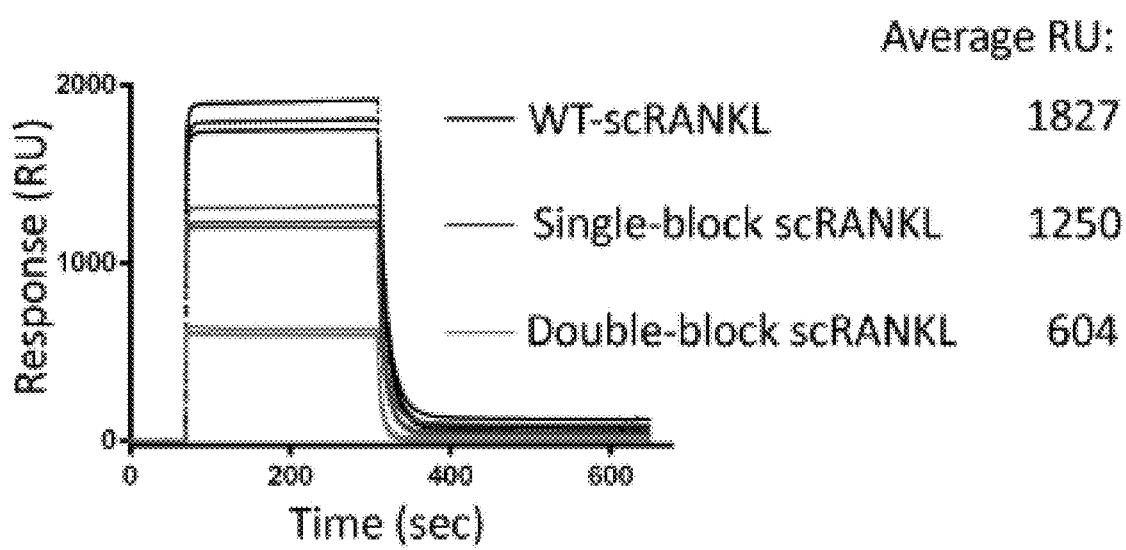

Example 3. Development of scRANKL Constructs that Block Receptor Recruitment To engineer scRANKL constructs that blocked receptor binding at one site ("single-block scRANKL") or two sites ("double-block scRANKL", FIG. 1D), we inserted short sequences into several loops of RANKL (FIG. 2A) or introduced point mutations that disrupted salt bridge formation (FIG. 7). One mutant, in which three amino acid residues (Gly-Gly-Ser) were inserted into the c-terminal end of strand C after residue 222 (CDins htRANKL), failed to bind to a recombinant fusion protein of Fc and RANK (RANK-Fc) despite undergoing proper folding, as established by its ability to bind to OPG-Fc in a dose-dependent manner (FIG. 2B). Consistent with its failure to bind to RANK, the CDins htRANKL mutant was incapable of inducing osteoclast formation or promoting RANK signaling in bone marrow macrophages (BMMs) (FIG. 2C). Next, we generated single-block and double-block scRANKL mutants by inserting CDins into one or two monomers, respectively, of the single-chain trimer. We compared the degree of receptor binding at saturation by flowing monomeric RANK, as an analyte, over a surface plasmon resonance (SPR) chip. As expected, blocking each binding site diminished receptor recognition by approximately one-third (FIG. 2D).

Having developed scRANKL variants that had an altered capacity to initiate trimeric receptor clustering, which is presumed to be required for optimal signaling, yet retained the ability to bind to RANK, we postulated that these proteins might act as inhibitors of osteoclastogenesis induced by wild-type htRANKL; however, this proved not to be the case (FIG. 8). This lack of inhibitory ability likely reflected the failure of the one (or two) intact binding site(s) to overcome the avidity afforded by the three sites of wild-type htRANKL. We reasoned that we might increase the inhibitory effectiveness by compensating for the reduced avidity of single-block or double-block scRANKL through increasing the affinity for RANK at the intact site(s). This required identifying previously uncharacterized RANKL mutations that increased its affinity for RANK.

Figure 9A:
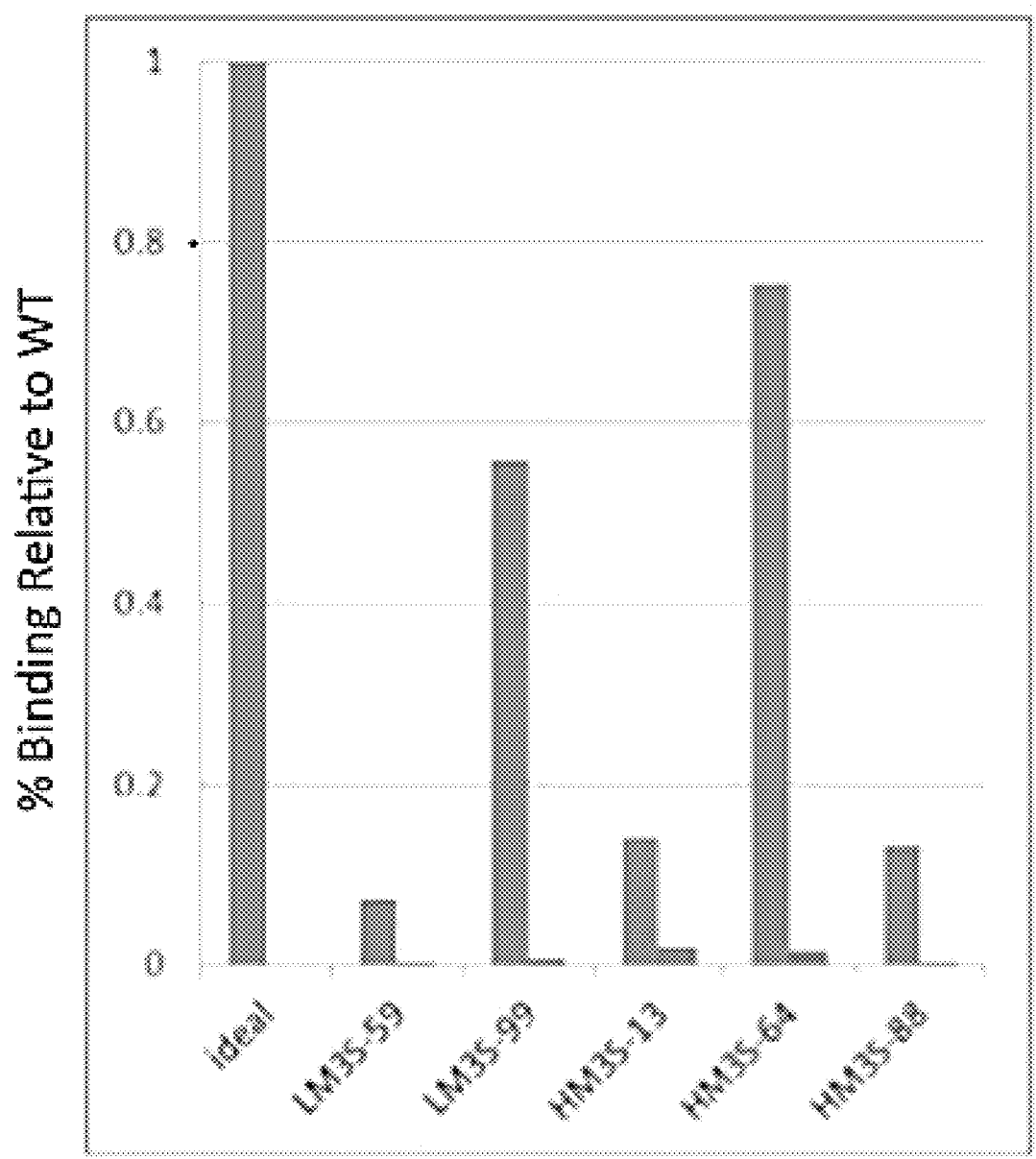
Figure 9B:
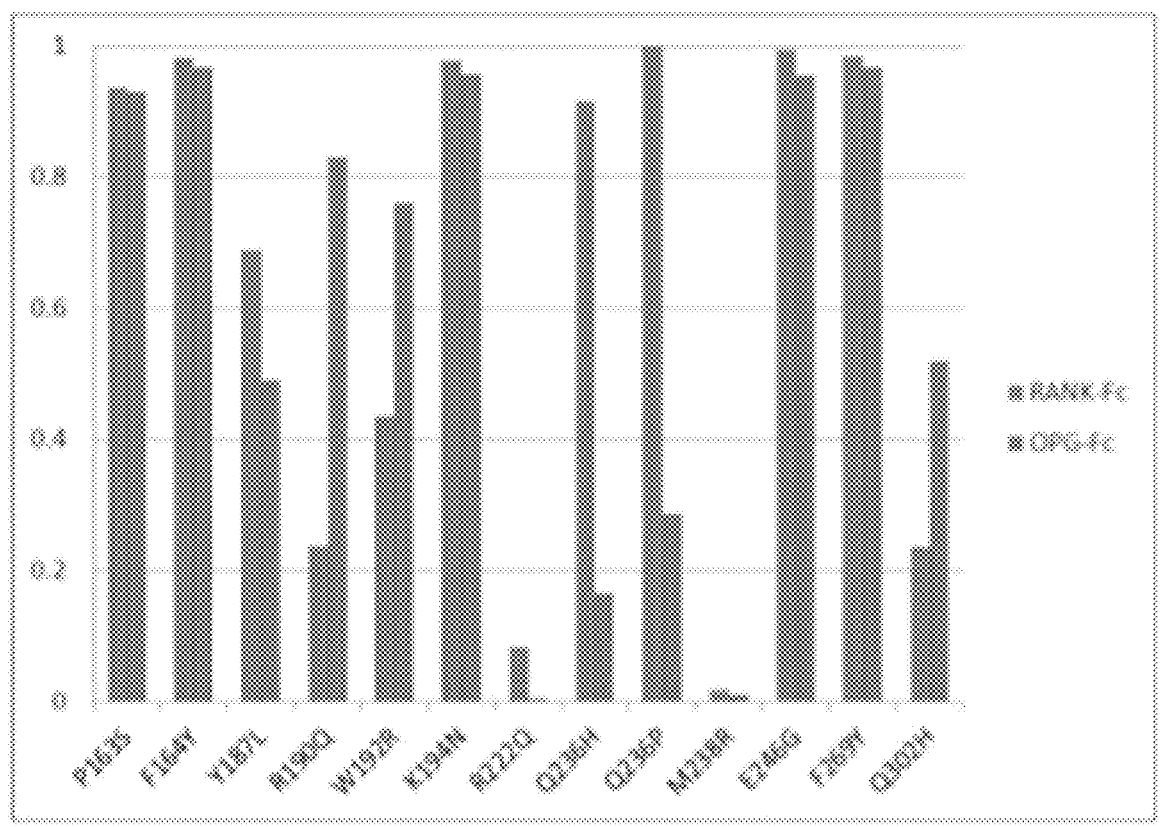
Figure 9C:
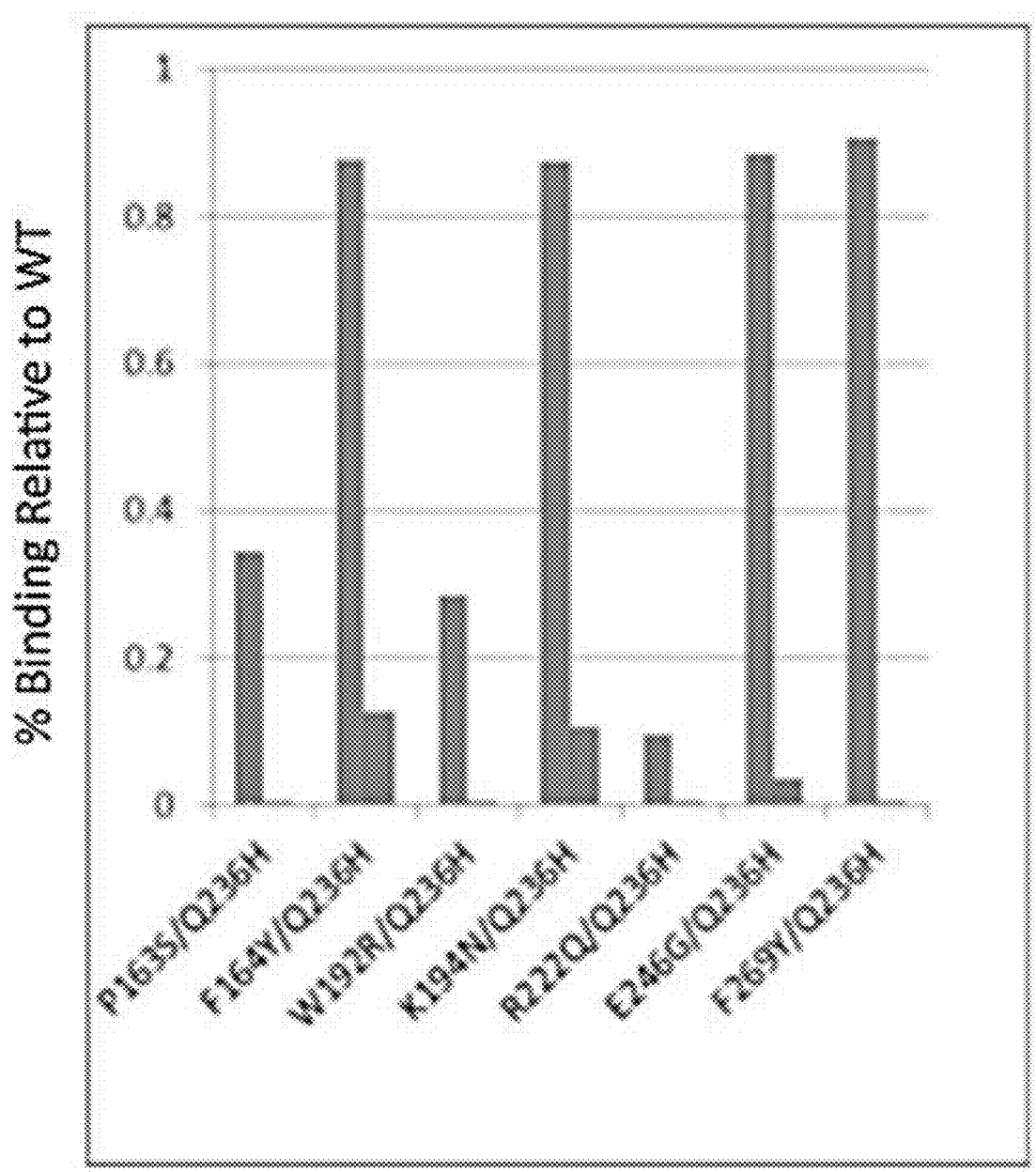
Figure 9D:
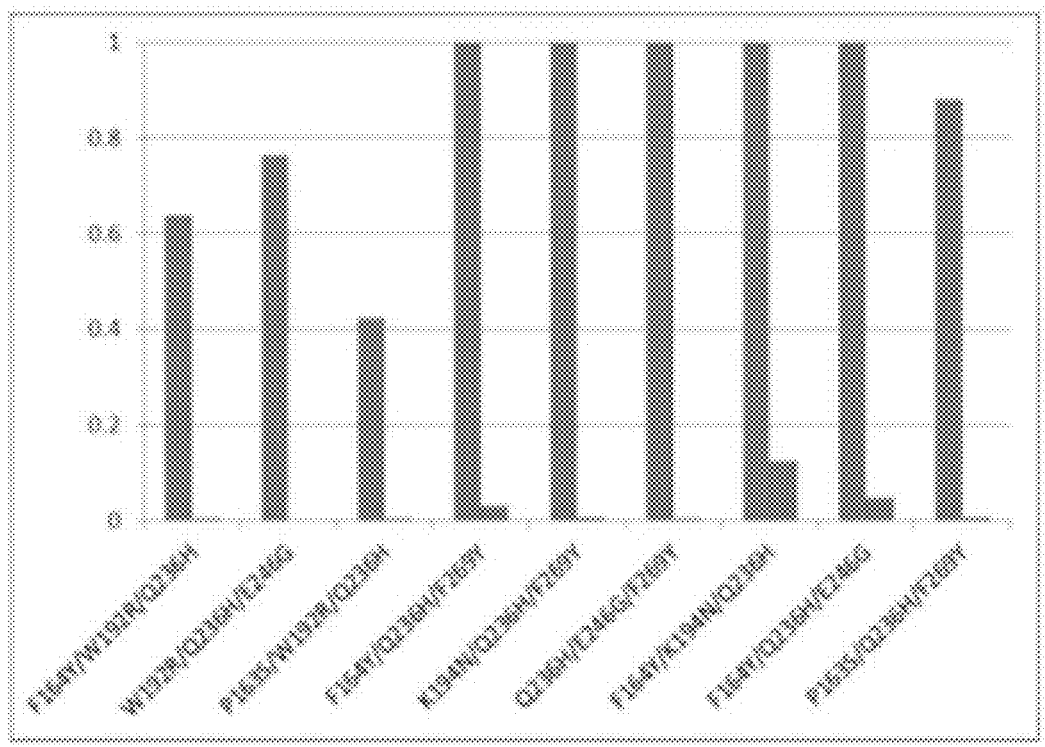

Example 4. Two Generations of In Vitro Evolution Through Yeast Surface Display Identifying Previously Uncharacterized RANKL Mutations that Increased its Affinity for RANK To identify RANKL mutations that increase affinity for RANK, we performed two generations of in vitro affinity maturation through yeast surface display (YSD) (17). The first round involved creating a library of htRANKL mutants through error-prone polymerase chain reaction (PCR) assays and sorting for clones that retained the ability to bind to RANK-Fc. Notably, OPG, the principal biological inhibitor of RANK-induced osteoclastogenesis (18-20), exerts its effects by competing with RANK for binding to RANKL. Because both RANK and OPG bind to the same groove of RANKL, it is possible that increasing the affinity of RANKL for RANK could simultaneously increase its binding to the decoy receptor. To obviate this possibility, we simultaneously sorted the library for clones with higher affinity for RANK and with decreased affinity for OPG-Fc (FIG. 9A). Reversion mutagenesis yielded individual point mutations (K194N, Q236H, F269Y) in htRANKL which, when expressed in combination (KQF), substantially increased the affinity of the mutant htRANKL for RANK-Fc while decreasing its affinity for OPG-Fc (FIGS. 9, B C, and D).

Figure 3A:
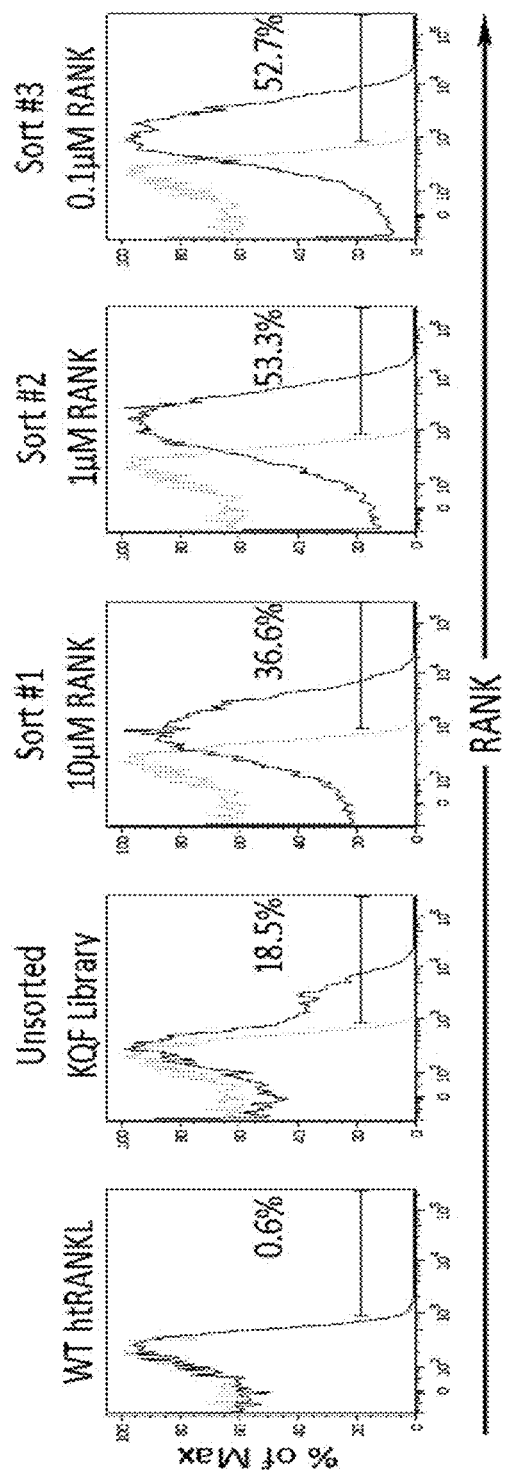
Figure 3C:
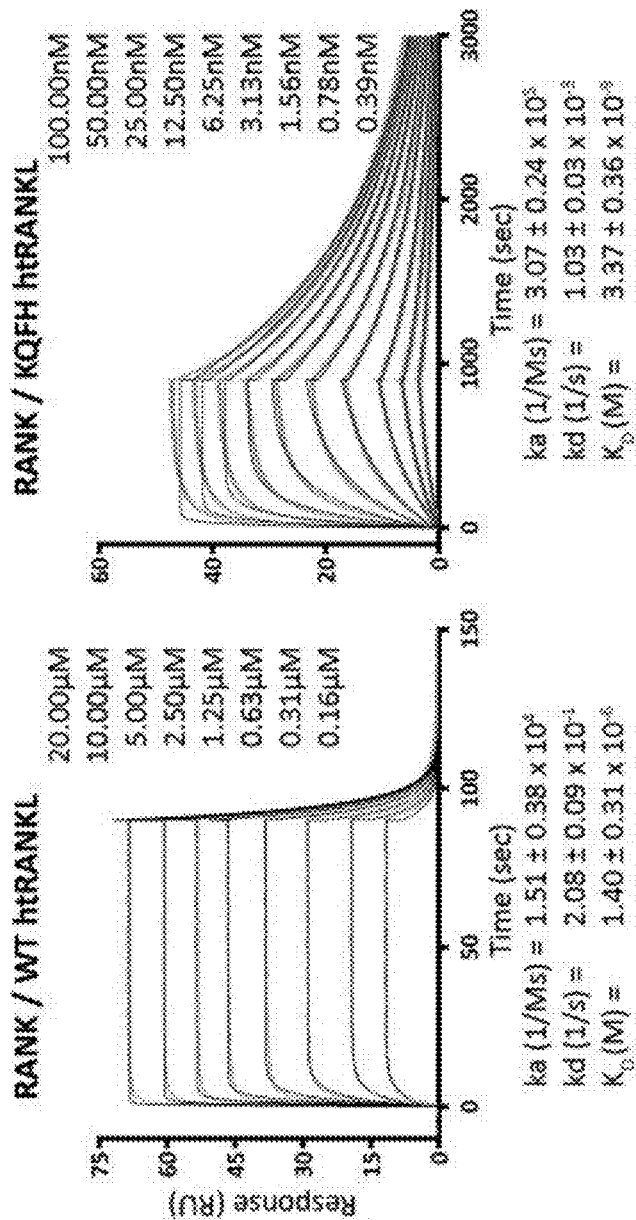
Figure 3D:
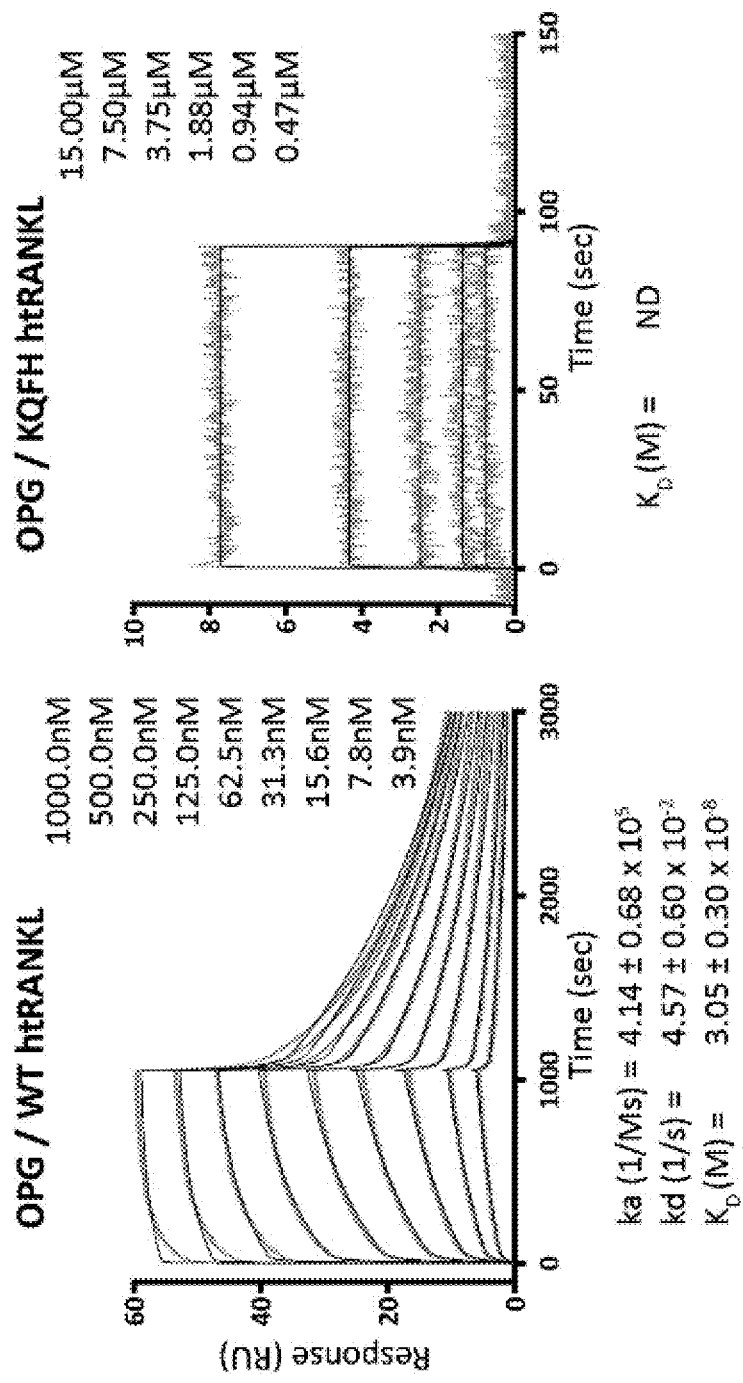
Figure 4A:
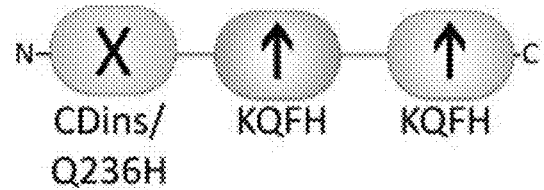
Figure 4A:
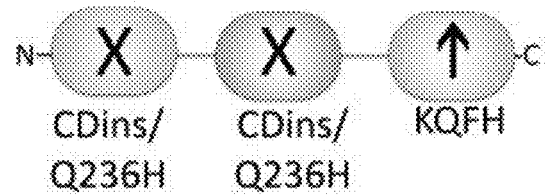
Figure 4B:
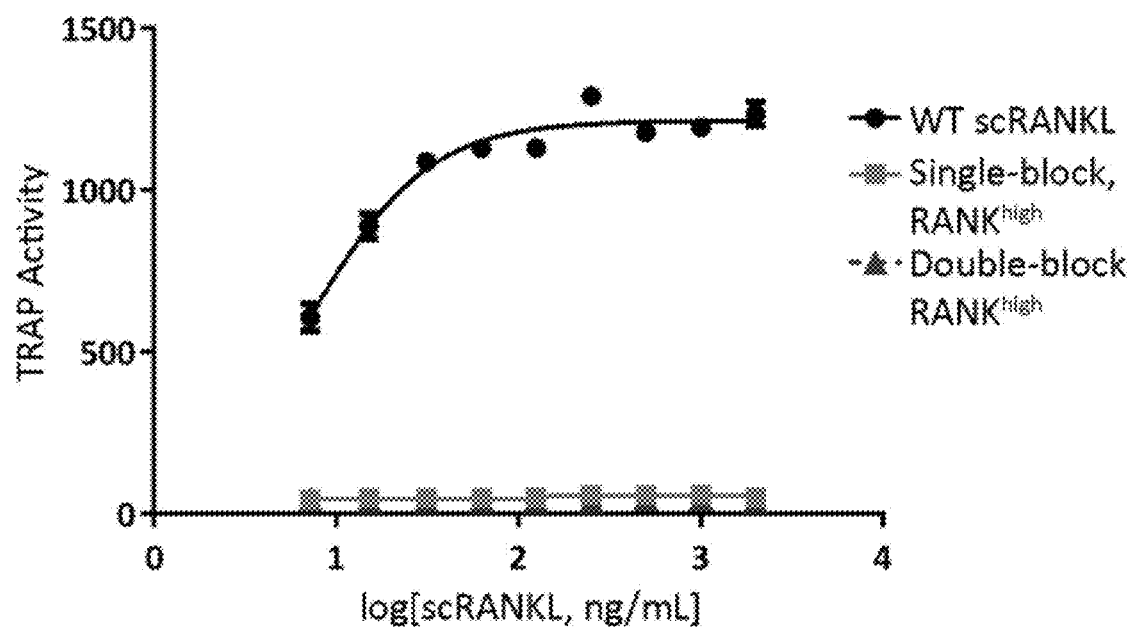
Figure 4C:
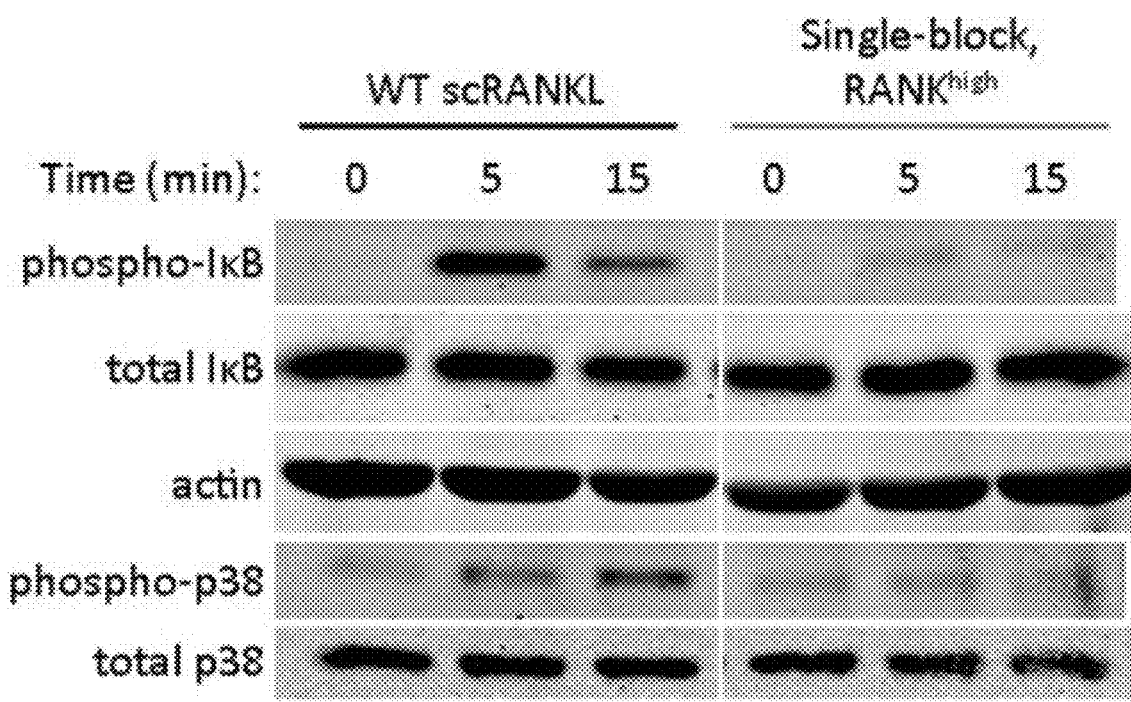
Figure 4D:
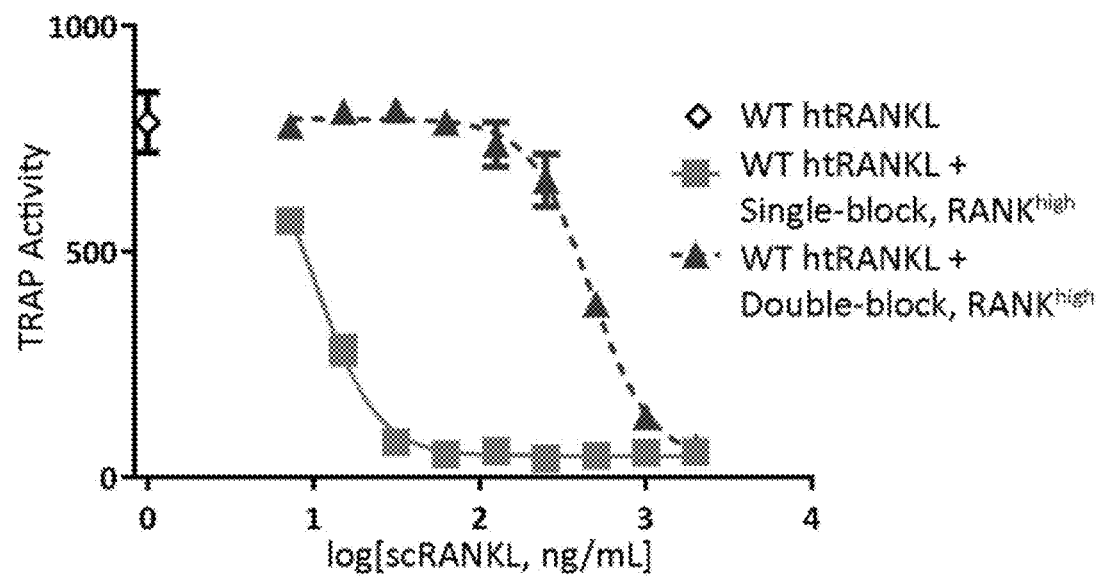
Figure 4E:
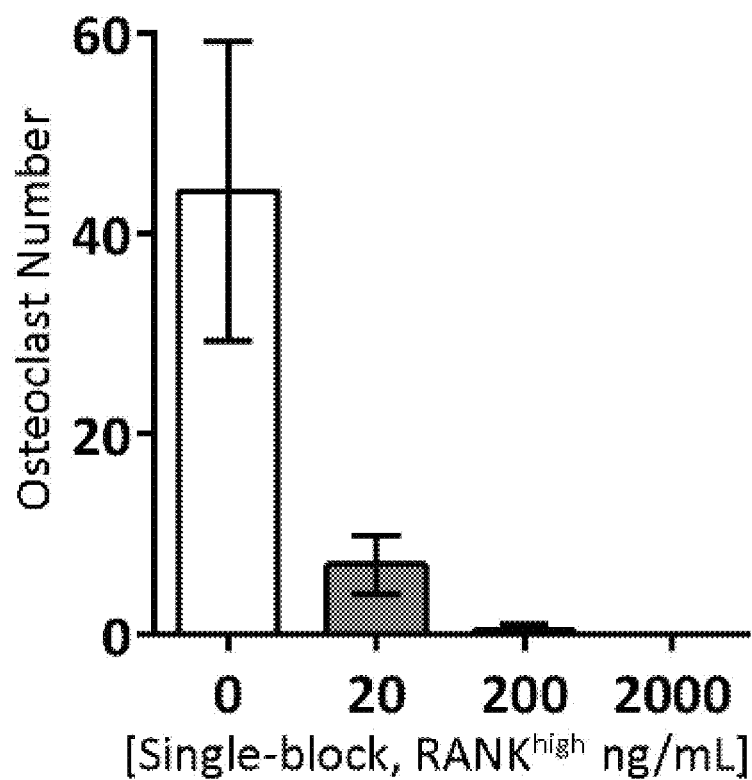
Figure 4F:
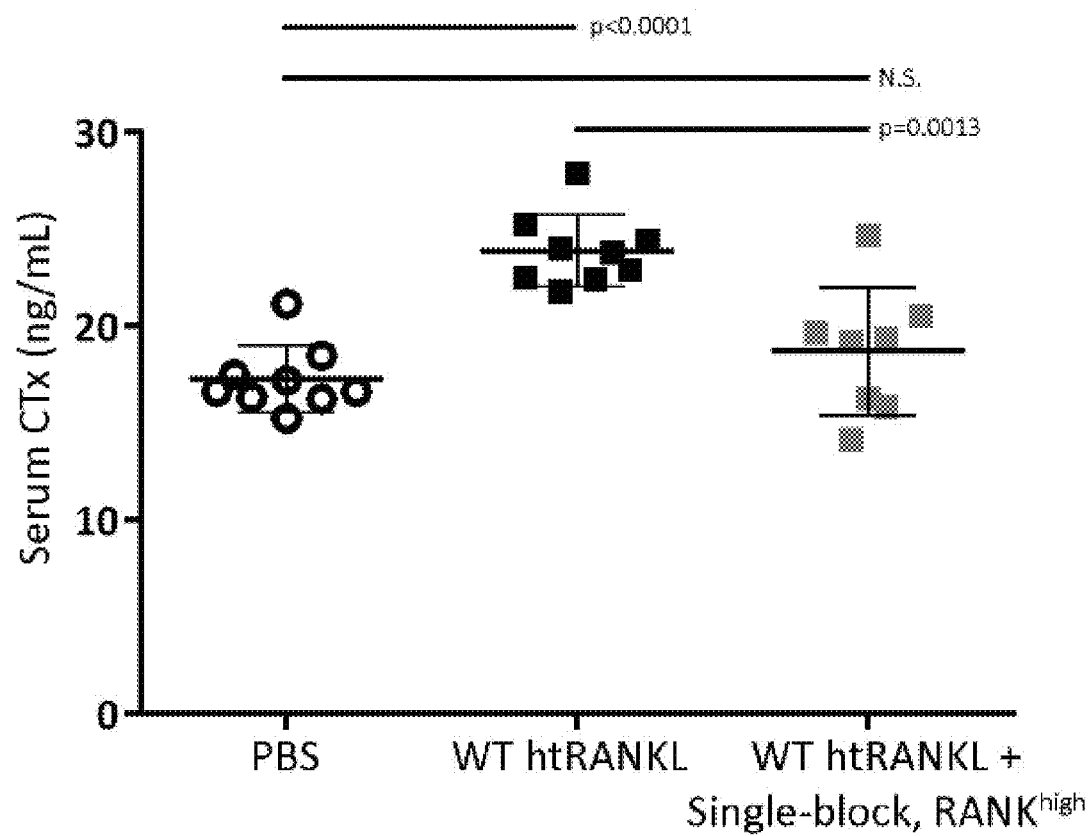

In the second generation of in vitro evolution, we selected htRANKL variants with long RANK kinetic half-lives. We again constructed an htRANKL mutant library through error-prone PCR, but this time used the high-affinity KQF htRANKL mutant as a starting template. Because of its rapid off-rate, monomeric RANK did not stain yeast-displayed wild-type htRANKL, despite their established interaction (FIG. 3A). We therefore sorted the second library with sequentially limiting amounts of monomeric RANK. This sorting strategy yielded a population of htRANKL variants that were capable of binding monomeric RANK (FIG. 3A).

Example 5. Identification of an Additional RANKL Point Mutation and Development of RANKL Variants Including the Additional Point Mutation We next selected htRANKL variants that continued to bind to limiting amounts of RANK after incubation in the presence of unlabeled OPG for 5 min at room temperature (FIG. 10). We identified several additional mutations at residue K194 and chose to use the K194E mutation going forward in KQF htRANKL, because the K194N mutation introduced a potential N-linked glycosylation site that could confound results when comparing proteins produced by yeast and mammalian cells. These strategies also yielded the htRANKL point mutant (H270Y), which, when incorporated into the KQF htRANKL mutant, further increased its affinity for RANK without yielding detectable binding to OPG (FIG. 3B). We then determined the affinities and kinetic parameters of the RANKL variant that showed the greatest binding to RANK by SPR (FIG. 3C). Although the two solubility mutations that were introduced to produce scRANKL had no effect on RANK binding, they resulted in an approximately ten-fold decrease in binding to OPG (FIG. 11). The KQFH htRANKL variant bound to RANK with an approximately 500-fold greater affinity than did wild-type htRANKL; however, it exhibited substantially impaired binding to OPG (FIG. 3B). These changes in affinity for RANK largely reflected a prolonged half-life of binding, changing from a relatively rapid dissociation time ($t_{1/2}$=3 s for WT htRANKL) to a dissociation time that was more than 200-times longer ($t_{1/2}$=675 s for KQFH htRANKL). The KQFH mutations cluster in two regions of RANKL that were previously implicated in binding to RANK (9) (FIG. 12). To ensure that the RANK-blocking interface would also block binding to OPG, we combined CDins with the Q236H mutation, because $Gln^{26}$ was identified by YSD as the amino acid residue responsible for decreased binding to OPG. Indeed, we confirmed that the variant RANKL that combined CDins with the Q236H mutation did not bind to RANK (FIG. 13).

Example 6. Generation of an Inhibitor of RANKL-Mediated Signaling

To generate an effective inhibitor of RANKL-mediated signaling, we incorporated the high-affinity KQFH variant ($RANK^{high}$) into our single-block and double-block constructs (FIG. 4A). Before determining the capacity of these scRANKL variants to act as inhibitors of RANKL-RANK signaling, we assessed their capacity to generate osteoclasts. Both the single-block and double-block scRANKL variants that had increased affinity for RANK (single-block, $RANK^{high}$ and double-block, $RANK^{high}$) were incapable of generating osteoclasts in vitro (FIG. 4B). Concurrently, we observed a lack of associated signals induced by the single-block, $RANK^{high}$ variant (FIG. 4C). In contrast to the failure of single-block or double-block scRANKL containing unaltered residual monomer(s) to inhibit RANK signaling and osteoclast formation, the double-block, $RANK^{high}$ scRANKL variant effectively inhibited signaling stimulated by wild-type htRANKL with an $IC_{50}$ of ~10 nM (FIG. 4D).

The potency of inhibition increased (resulting in an $IC_{50}$ of 0.2 nM) when two sites were available to bind RANK with high affinity (single-block, $RANK^{high}$), and this effect was not attributable to cytotoxic effects (FIG. 14A). Additionally, blockade was specific for RANK-mediated signaling, because TNF receptor 1 (TNFR1)-mediated phosphorylation of inhibitor of κB α (IκBα) downstream of TNF-α was not blocked by the single-block, $RANK^{high}$ variant (FIG. 14B). The inhibitory effects of the single-block, $RANK^{high}$ variant were not limited to exogenous wild-type htRANKL, because it also dose-dependently inhibited osteoclast formation induced by htRANKL produced by osteoblasts (FIG. 4E).

Example 7. Intraperitoneal scRANKL Injection

We tested the effectiveness of the single-block, $RANK^{high}$ variant at blocking recombinant wild-type htRANKL-induced osteoclastic bone resorption in vivo. Intraperitoneal injection of recombinant wild-type htRANKL into 8-week old BALB/c mice increased osteoclast function as determined by measuring serum carboxy-terminal collagen crosslinks (CTx), a marker of bone resorption (FIG. 4F). This increase in bone resorption was completely abrogated by the addition of an equal amount of the single-block, $RANK^{high}$ variant, which suggests that this inhibitor may have therapeutic potential.

Example 8. Development of a scTNFL Variant

A TNF variant is developed using a strategy of combining high affinity and blocking mutations into a single-chain construct. An effective inhibitor that is receptor selective is produced. This TNF variant inhibitor can block TNFR1 while sparing TNFR2, thereby reducing systemic complications.

Example 9. Materials and Methods Used

Construction of an scRANKL Vector and Cloning of cDNAs Encoding scRANKL, htRANKL, and TNF-α into a Mammalian Expression Vector Initially, the cDNA encoding scRANKL was cloned into the pGEX vector (GE-Healthcare) by PCR-based amplification of the coding sequence of the mouse RANKL monomer (including amino acid residues 162 to 316 of NCBI Reference Sequence NP_035743) with primer pairs that inserted the following restriction enzyme sites: 5'-Sma I-RANKL-Bsp EI-3', 5'-Bsp EI-RANKL-Bam HI-3', and 5'-Bam HI-RANKL-Not I-3'. The primers were designed such that the three monomers are separated by a linker sequence [(Gly-Gly-Ser-Gly)×3). Each insert was double-digested with the appropriate restriction enzymes (Fermentas) and ligated into the pGEX vector between the Sma I and Not I sites. The entire scRANKL cDNA was subcloned into the mammalian protein expression vector pFM (32) (gift of Dr. Filipo Mancia) downstream of the signal peptide from pHLsec (MGILPSPGMPALLSLVSLLSVLLMGCVA; SEQ ID NO:25) (33). To aid protein recovery, a tobacco etch virus (TEV) protease cleavage site and a 6×-histidine tag were added at the C-terminus (SSGRENLYFQGHHHHHH; SEQ ID NO:26). The 6×-histidine tag can be removed by TEV cleavage to yield the sequence SSGRENLYFQ (SEQ ID NO:27) at the C-terminus of the recovered protein. In brief, the construct encodes: a signal-peptide, RANKL (residues 162 to 316), a linker, RANKL (residues 162 to 316), a linker, RANKL (residues 162 to 316), a TEV cleavage site, and the 6×His tag. Expression of the construct is driven by the CMV promoter. Transfection efficiency was monitored by detection of red fluorescent protein, whose expression is initiated downstream of scRANKL at an internal ribosomal entry site. To clone the cDNA encoding htRANKL into the pFM mammalian expression vector, the cDNA sequence encoding amino acid residues 162 to 316 was amplified, digested with the restriction enzymes Bsu 36I and Sal I, and ligated downstream of the pHLsec signal peptide and upstream of the TEV cleavage site. To clone the cDNA encoding murine TNF-α, the cDNA sequence encoding amino acid residues 90 to 325 was amplified by overlap extension PCR to add a 5' pHLsec signal peptide site and a 3' Sal I restriction site. The cDNA was digested with Xba I and Sal I and ligated downstream of the CMV promoter and upstream of the TEV cleavage site.

Production of Mammalian RANKL and TNF-α Proteins

Suspension-adapted 293-Freestyle cells (Life Technologies) were maintained in serum-free Freestyle 293 expression medium (Life Technologies) according to the manufacturer's protocol. For transfection, DNA was prepared with an endotoxin-free maxiprep kit (Qiagen). Cells were seeded at a density of $0.5\times10^6$/ml in 200 ml of medium 24 hours before transfection. On the day of transfection, DNA and polyethylenimine (33) were mixed at a ratio of 1:3 (htRANKL or TNF-α, 200 pg:600 µg) or 1:2 (scRANKL variants, 200 µg:400 µg) in opti-mem (Life Technologies), incubated for 15 min at room temperature, and added directly to the cells. Cell culture medium was harvested four and seven days after transfection, filtered through a 0.22-µm filter, and equilibrated by the addition of 0.1 volume of 10× phosphate-buffered saline (PBS, Gibco) and 10 mM imidazole. The protein was captured on Ni-NTA Superflow resin (Qiagen) and washed with 10 mM imidazole in PBS. Protein was eluted in steps from 25 to 500 mM imidazole. Fractions containing purified protein were identified by coomassie stained SDS-polyacrylamide gel electrophoresis (SDS-PAGE). Protein-containing fractions were pooled and concentrated with a disposable YM30 centricon (Millipore). All proteins were sterile-filtered for use in cell culture. Only lipopolysaccharide (LPS)-free plastics and reagents were used for all purifications.

SPR Measurements

All SPR experiments were performed on a Biacore T-100 (GE Healthcare) with CM5 sensor chips and HBS-EP buffer (10 mM HEPES (pH 7.4), 150 mM NaCl, 3 mM EDTA, and 0.05% v/v Surfactant P20). To confirm receptor binding to scRANKL variants, 4,000 response units (RU) of wild-type (WT) scRANKL or variant scRANKL were coupled to individual lanes, leaving one reference flow cell uncoupled. Monomeric RANK (20 µM) was flowed over until saturation. Total RUs bound at equilibrium were calculated with BIAEvaluation software. Experiments to determine kinetic affinity constants of RANKL variants for RANK or OPG were performed and analyzed as previously described (9).

Generation of Osteoclasts from Primary Bone Marrow-Derived Macrophages

Long bones isolated from eight week-old mice were flushed, and the marrow was subjected to red blood cell lysis. The remainder of the whole marrow was cultured on petri dishes or bone powder as previously described (34), maintained at 37° C. and 6% $CO_2$ in α-MEM medium containing 10% heat-inactivated f et al bovine serum (FBS), penicillin (100 U/ml), streptomycin (100 µg/ml), (α-10 medium) supplemented with 1:10 CMG [conditioned medium supernatant containing recombinant M-CSF (macrophage colony-stimulating factor)](35). Osteoclasts were differentiated in α-10 medium with 1:50 CMG and the relevant RANKL variant.

Detection of Osteoclast Formation

Cells were fixed in 4% paraformaldehyde in PBS for 15 min and stained for tartrate-resistant acid phosphatase (TRAP) with a specific kit (Sigma). Additionally, osteoclasts were quantified by a solution assay of TRAP enzyme activity. Cells were fixed and lysed in 90 mM citrate buffer (pH 5.2), 80 mM sodium tartrate, 0.1% Triton-X-100 for 10 min at room temperature. Colorimetric nitrophenylphosphate (a substrate of TRAP) was added and visualized after 15 min by the addition of sodium hydroxide. Data were acquired with the 405-nM absorbance filter on a Bio-rad plate reader. Because of the limited range of the TRAP solution assay, a more quantitative assessment of TRAP activity was performed with the fluorescent phosphatase substrate ELF-97 (Molecular Probes). Fixed cells were incubated with 100 µM ELF-97 in 90 mM citrate buffer (pH 4.8), 80 mM sodium tartrate for 15 min at room temperature. The reaction was stopped by the addition of sodium hydroxide, and fluorescence was visualized with the 345/530 excitation/emission filter on a Spectramax M2 plate reader.

Multi-Angle Light Scattering (MALS) Analysis

Purified RANKL proteins were applied to a Wyatt WTC-030S5 size-exclusion column mounted on a Waters HPLC system attached to a multi-angle light scattering (MALS) device. The light detectors, a Dawn HELEOS-II 18-angle light scattering detector and an Optilab rEX refractive index, were previously calibrated against monomeric bovine serum albumin. MALS was monitored during the experiments, and the resulting data were analyzed with associated software. For each experiment, 250 µg of sample was applied at a concentration of 1 mg/ml in running buffer [25 mM hepes (pH 7.4), 150 mM NaCl, 0.01% sodium azide) at 20° C. and a flow rate of 0.5 ml per minute.

Chemical Cross-Linking

Purified WT-RANKL protein (500 ng) was incubated with varying concentrations (0 to 500 µM) of the chemical cross-linker bis-(sulfosuccinimidyl)-suberate ($BS^3$, Pierce) in PBS at room temperature for 30 min, at which time the reaction was stopped by the addition of 10 mM Tris-HCl (pH 7.0). Samples were boiled under reducing conditions and loaded onto SDS-PAGE gels (10%) alongside 500 ng of scRANKL protein. Bands were stained with the coomassie derivative Imperial protein stain (Pierce) and visualized with the Odyssey scanner (Licor).

Identification of RANKL Mutants that Did not Bind to RANK

RANKL residues forming salt bridges or hydrogen bonds with RANK were targeted for site-directed mutagenesis with PISA software based on the RANK-RANKL co-crystal structure (9). Loops at the RANK-RANKL binding interface were disrupted by amino acid insertion. Mutations were introduced into the expression construct, pGEX-GST-RANKL, by PCR with Phusion™ polymerase (NEB). The constructs were verified by nucleic acid sequencing. Escherichia coli strain BL21-CodonPlus (DE3)-RIL competent cells (Agilent Technologies) were transformed with the mutant RANKL-encoding constructs to generate proteins. Correctly folded soluble proteins were purified from cell lysates on glutathione sepharose (8).

Bio-Layer Interferometry (BLI)

All BLI experiments were performed on an Octet RED™ system (ForteBio). Glutathione-S-transferase (GST)-RANKL fusion proteins were biotinylated with NHS-PEG4-biotin (Pierce) according to the manufacturer's protocol, and excess biotin was removed by desalting over Zeba™ Spin Columns (7-kD molecular mass cutoff, Pierce). Biotinylated proteins were adsorbed onto super-streptavidin sensor pins (ForteBio). Binding of RANK-Fc or OPG-Fc was measured in HBS-EP containing 1% BSA. Because of the dimeric nature of Fc-tagged receptors, only apparent $K_D$ values were observed.

Quantitative Real-Time PCR Analysis

To quantitate the abundances of mRNAs for markers of osteoclast formation, total RNA was isolated from cultured cells with the Qiagen RNeasy™ miniprep kit according to the manufacturer's protocol. Equal amounts of RNA were used to perform reverse transcription with Bio-rad iScript™, and quantitative real-time PCR analysis was performed with a SsoFast EvaGreen™ qPCR kit (Bio-Rad) with a 7500 fast machine (ABI). Cyclophilin was used as the housekeeping control gene. Data were analyzed according to the ΔΔCt method, and expressed relative to a control containing no RANKL addition (labeled BMM). The primers used were as follows: Cathepsin K (Forward: 5'-ATGTGGGTGTT-CAAGTTTCTGC-3' (SEQ ID NO:28), Reverse: 5'-CCACAAGATTCTGGGGACTC-3'), SEQ ID NO:29); NFATcl (Forward: 5'-CCCGTCACATTCTGGTCCAT-3', SEQ ID NO:30); Reverse: 5'-CAAGTAACCGTGTAGCTGCACAA-3' (SEQ ID NO:31), TRAP (Forward: 5'-CAGCTCCCTAGAAGATG-GATTCAT-3', SEQ ID NO:32, Reverse: 5'GTCAG-GAGTGGGAGCCATATG (SEQ ID NO:33), 33 (Forward: 5'-TTCGACTACGGCCAGATGATT-3', SEQ ID NO:34) Reverse: 5'-GGAGAAAGACAGGTCCATCAAGT-3' (SEQ ID NO:35) and Cyclophilin (Forward: 5' AGCATA-CAGGTCCTGGCATC-3', SEQ ID NO:36); Reverse: 5-TT-CACCTTCCCAAAGACCAC-3'; SEQ ID NO:37).

Western Blotting

Cells were washed three times in ice-cold PBS and lysed with RIPA buffer (Millipore) supplemented with protease and phosphatase inhibitor cocktail (Pierce). After 10 min of incubation on ice, cell lysates were cleared of debris by centrifugation for 15 min at 21,000 g. Forty to fifty micrograms of protein were resolved by 10% SDS-PAGE, transferred onto polyvinylidene difluoride (PVDF) membranes, and incubated with primary antibody overnight. After extensive washing and incubation with near-infrared-labeled secondary antibody, membranes were visualized with the Odyssey scanner (Licor). Primary antibodies to detect phosphorylated or total NF-κB or p38 MAPK proteins were obtained from Cell Signaling; antibody against actin was from Sigma; and fluorescently labeled secondary antibodies were obtained from Rockland.

YSD of RANKL and Flow Cytometric Staining with Monomeric RANK or OPG

The cDNA encoding WT-SM RANKL was subcloned into the pYD1 yeast display vector (Life Technologies) at the Nhe I and Xho I restriction sites to generate the yeast mating protein Aga2p fused to the RANKL N-terminus and having a V5-epitope tag at the C-terminus. EBY100 yeast cells were transformed with the pYD1-RANKL construct using the lithium acetate/single-stranded DNA method as described (36) and colonies were selected in tryptophan-deficient, glucose-based medium at 30° C. Display of RANKL protein was induced by inoculating into galactose-based selective medium and incubating at 30° C. with shaking for 24 to 48 hours. Surface expression of RANKL was detected with a fluorescein isothiocyanate (FITC)-conjugated anti-V5 antibody (Invitrogen). After incubation with RANK-Fc or OPG-Fc for 10 min at room temperature and washing with ice-cold PBS, receptor binding was detected with an allophycocyanin (APC)-conjugated anti-human Fc antibody (Molecular Probes). All experiments were performed with LSR II or Canto II flow cytometers (BD Biosciences) and data were analyzed with the FlowJo™ software package (Tree Star, Inc.). Alternatively, RANK-6×His or OPG-6×His proteins were detected with APC-labeled anti-6×His antibody (MBL International).

Generation of RANKL Library and Selection

Primers annealing immediately 5' or 3' to the cDNA sequence encoding RANKL in the pYD1 vector were designed and used in error-prone PCR amplification (Gene Morph II, Agilent). Lower and higher mutation rates were accomplished by manipulating the amount of starting template and the number of amplification cycles. The resulting product was further amplified with the high-fidelity Phusion polymerase (Finnzymes). Simultaneously, the pYD1 vector backbone was amplified with primers that extended outward from the regions surrounding RANKL-V5, leaving 24 base pairs of overlap between the vector backbone and the amplified mutant RANKL-V5 insert. These purified PCR products were used in the transformation of EBY100 cells according to established protocols (36), which yielded a library of approximately $1 \times 10^6$ transformants. Selections were made with magnetic assisted cell sorting (MACS, Miltenyi). Approximately $1 \times 10^7$ cells were induced from either the low or high mutation rate libraries, and both were first sorted for the expression of the V5 C-terminal tag, which indicated proper folding of the full-length protein. This was performed by incubating the cells with FITC-labeled anti-V5 antibody and selecting cells with anti-FITC microbeads for cell separation. After growth of the selected clones, cells were again induced to display RANKL protein, incubated with OPG-Fc, and washed, and those clones that did not bind to OPG were collected as the flow-through on a Protein A magnetic bead column. These cells were then labeled with RANK-Fc, and this time those clones that retained binding to the Protein A column were collected. After sorting, cells were allowed to multiply in selective medium, and this strategy was repeated twice to yield clones termed "LM3S" and "HM3S". Approximately 200 individual colonies were isolated from the libraries and stained with OPG-Fc. Those clones with little to no detectable staining were then assessed for their ability to bind to RANK-Fc. DNA was extracted from the top scoring clones of interest with a yeast miniprep kit (Zymoprep) and used to transform chemically competent DH5α E. coli (Invitrogen) for sequencing. Individual point mutations were then added to the cDNA encoding RANKL by site-directed mutagenesis, and subsequent combinations were cloned in a similar fashion. A second round of error-prone PCR used the identical primers and protocol described earlier, but used as the starting template either of the F164Y/Q236H/F269Y or K194N/Q236H/F269Y triple mutants. Clones were selected over three rounds of sorting with three sequentially lower amounts of monomeric RANK-6×His and anti-6×His microbeads. Finally, the resulting library was incubated with RANK-6×His at room temperature for 10 min and then tested for the ability to outcompete the presence of unlabeled OPG at room temperature for 5 min. Residual RANK binding was detected with APC-labeled anti-6×His antibody. In the course of sorting, the K194E mutation was identified and used to replace the K194N mutation, which introduced a potential N-linked glycosylation site at the interface with RANK or OPG.

Assessment of Cell Viability with the MTT Assay

Cells were seeded in 96-well plates either in αMEM alone, WT htRANKL (200 ng/ml) alone or in combination with single-block, RANK$^{high}$ (2,000 ng/ml), or only single-block, RANK$^{high}$. After 3 days, a 1:10 dilution of MTT reagent (3-[4,5-dimethylthiazol-2-yl]-2,5-diphenyltetrazolium bromide, Sigma-Aldrich) was added (final concentration of 0.5 mg/ml) to the culture medium and incubated at 37° C. After 3 hours, 150 µl of 0.04 N HCl in isopropanol was added to each well to stop the reaction, and MTT absorbance was determined at an OD of 595 nm.

Co-Culture Assays

Calvarial osteoblasts were isolated and expanded in number as previously described (37). Briefly, osteoblasts were isolated from the calvaria of three day-old pups by 3×20-min treatments with collagenase. Cells were expanded in number in α-MEM medium, and then were lifted and plated together with bone marrow-derived macrophages in a 96-well plate. Cells were co-cultured in the presence of 10 nM 1,25-Vitamin D3 in α-MEM medium with the indicated concentrations of single-block, RANK$^{high}$ scRANKL. On day 7, cells were treated with 0.1% collagenase for 15 min to remove osteoblasts, and then were fixed for TRAP staining.

Intraperitoneal Injection of Mice with RANKL

Eight week-old female Balb/c mice were purchased from NCI Frederick, housed in the animal facility at Washington University School of Medicine, and maintained according to the guidelines set by the Association for Assessment and Accreditation of Laboratory Animal Care. All animal studies were approved by the Animal Studies Committee of Washington University School of Medicine. PBS, WT-SM RANKL (0.5 mg/kg), or WT-SM RANKL and single-block, RANK$^{high}$ scRANKL (0.5 mg/kg) were injected intraperitoneally into the mice at 0, 24, and 48 hours, as previously described (38). Mice were sacrificed 1.5 hours after the third injection, and serum was collected by cardiac puncture. Serum concentrations of CTx were determined by ELISA according to the manufacturer's protocol (Immunodiagnostics Systems).

Example 10. Biological Sequences

The biological sequences for various TNFsf monomers, wild type scTNFsfL, scTNFsfL, peptide linkers, and DNA primers. National Center for Biotechnology Information (NCBI) database identifiers for certain sequences are also provided. These sequences, as well as related sequences of allelic variants, can be downloaded from the National Center for Biotechnology Information (NCBI) database on the world wide web at "ncbi.nlm.nih.gov/pubmed" using these identifiers and associated links.

TABLE 5

Biological sequences

| SEQ ID NO: | Sequence | Comments |
|---|---|---|
| 1 | MRRASRDYGKYLRSSEEMGSGPGVPHEGPLHPAPSAPA PAPPPAASRSMFLALLGLGLGQVVCSIALFLYFRAQMD PNRISEDSTHCFYRILRLHENADLQDSTLESEDTLPDSCR RMKQAFQGAVQKELQHIVGPQRFSGAPAMMEGSWLD VAQRGKPEAQPFAHLTINAASIPSGSHKVTLSSWYHDR GWAKISNMTLSNGKLRVNQDGFYYLYANICFRHHETS GSVPTDYLQLMVYVVKTSIKIPSSHNLMKGGSTKNWS GNSEFHFYSINVGGFFKLRAGEEISIQVSNPSLLDPDQDA TYFGAFKVQDID | Mouse wt RANKL monomer NCBI NM_011613.3 |
| 2 | MRRASRDYTKYLRGSEEMGGGPGAPHEGPLHAPPPPA PHQPPAASRSMFVALLGLGLGQVVCSVALFFYFRAQM DPNRISEDGTHCIYRILRLHENADFQDTTLESQDTKLIPD SCRRIKQAFQGAVQKELQHIVGSQHIRAEKAMVDGSW LDLAKRSKLEAQPFAHLTINATDIPSGSHKVSLSSWYHD RGWAKISNMTFSNGKLIVNQDGFYYLYANICFRHHETS GDLATEYLQLMVYVTKTSIKIPSSHTLMKGGSTKYWSG NSEFHFYSINVGGFFKLRSGEEISIEVSNPSLLDPDQDAT YFGAFKVRDID | Human wt RANKL monomer NCBI AF019047.1 |
| 3 | MSTESMIRDVELAEEALPQKMGGFQNSRRCLCLSLFSF LLVAGATTLFCLLNFGVIGPQRDEKFPNGLPLISSMAQT LTLRSSSQNSSDKPVAHVVANHQVEEQLEWLSQRANA LLANGMDLKDNQLVVPADGLYLVYSQVLFKGQGCPD YVLLTHTVSRFAISYQEKVNLLSAVKSPCPKDTPEGAEL KPWYEPIYLGGVFQLEKGDQLSAEVNLPKYLDFAESGQ VYFGVIAL | Mouse wt TNF monomer NCBI NM_013693.3 |
| 4 | MSTESMIRDVELAEEALPKKTGGPQGSRRCLFLSLFSFL IVAGATTLFCLLHFGVIGPQREEFPRDLSLISPLAQAVRS SSRTPSDKPVAHVVANPQAEGQLQWLNRRANALLANG VELRDNQLVVPSEGLYLIYSQVLFKGQGCPSTHVLLTH TISRIAVSYQTKVNLLSAIKSPCQRETPEGAEAKPWYEPI YLGGVFQLEKGDRLSAEINRPDYLDFAESGQVYFGIIAL | Human wt TNF monomer NCBI NM_000594.3 |
| 5 | MPSSGALKDLSFSQHFRMMVICIVLLQVLLQAVSVAVT YMYFTNEMKQLQDNYSKIGLACFSKTDEDFWDSTDGE ILNRPCLQVKRQLYQLIEEVTLRTFQDTISTVPEKQLSTP PLPRGGRPQKVAAHITGITRRSNSALIPISKDGKTLGQKI ESWESSRKGHSFLNHVLFRNGELVIEQEGLYYIYSQTYF RFQEAEDASKMVSKDKVRTKQLVQYIYKYTSYPDPIVL MKSARNSCWSRDAEYGLYSIYQGGLFELKKNDRIFVSV TNEHLMDLDQEASFFGAFLIN | Mouse wt TRAIL monomer NCBI NM_009425.2 |

TABLE 5-continued

Biological sequences

| SEQ ID NO: | Sequence | Comments |
|---|---|---|
| 6 | MAMMEVQGGPSLGQTCVLIVIFTVLLQSLCVAVTYVY FTNELKQMQDKYSKSGIACFLKEDDSYWDPNDEESMN SPCWQVKWQLRQLVRKMILRTSEETISTVQEKQQNISP LVRERGPQRVAAHITGTRGRSNTLSSPNSKNEKALGRKI NSWESSRSGHSFLSNLHLRNGELVIHEKGFYYIYSQTYF RFQEEIKENTKNDKQMVQYIYKYTSYPDPILLMKSARN SCWSKDAEYGLYSIYQGGIFELKENDRIFVSVTNEHLID MDHEASFFGAFLVG | Human wt TRAIL monomer NCBI NM_003810.3 |
| 7 | QPFAHLTINAASIPSGSHKVTLSSWYHDRGWAKISNMT LSNGKLRVNQDGFYYLYANISFRHHETSGSVPTDYLQL MVYVVKTSEKIPSSHNLMKGGSTKNWSGNSEFHFYSIN VGGFFKLRAGEEISIQVSNPSLLDPDQDATYFGAFKVQD ID GGSGGGSGGGSG QPFAHLTINAASIPSGSHKVTLSSWYHDRGWAKISNMT LSNGKLRVNQDGFYYLYANISFRHHETSGSVPTDYLQL MVYVVKTSEKIPSSHNLMKGGSTKNWSGNSEFHFYSIN VGGFFKLRAGEEISIQVSNPSLLDPDQDATYFGAFKVQD ID GGSGGGSGGGSG QPFAHLTINAASIPSGSHKVTLSSWYHDRGWAKISNMT LSNGKLRVNQDGFYYLYANISFRHHETSGSVPTDYLQL MVYVVKTSEKIPSSHNLMKGGSTKNWSGNSEFHFYSIN VGGFFKLRAGEEISIQVSNPSLLDPDQDATYFGAFKVQD ID SSGRENLYFQ | Mouse WT Single Chain RANKL peptide sequence with solubility mutations (C220S/I246E) (mature; no signal peptide and no Hisx6 tag) |
| 8 | QPFAHLTINAASIPSGSHKVTLSSWYHDRGWAKISNMT LSNGKLRVNQDGFYYLYANISFRHNETSGSVPTDYLQL MVYVVKTSEKIPSSHNLMKGGSTKNWSGNSEFHFYSIN VGGFFKLRAGEEISIQVSNPSLLDPDQDATYFGAFKVQD ID GGSGGGSGGGSG QPFAHLTINRASIPSGSHKVTLSSWYHDRAWAKISNMT LSNGKLRVNQDGFYYLYANISFRHHETSGSVPTDYLQL MVYVVKTSEKIPSSHNLMKGGSTKNWSGNSEFHFYSIN VGGFFKLRAGEEISIQVSNPSLLDPDQDATYFGAFKVQD ID GGSGGGSGGGSG QPFAHLTINRASIPSGSHKVTLSSWYHDRAWAKISNMT LSNGKLRVNQDGFYYLYANISFRHHETSGSVPTDYLQL MVYVVKTSEKRPSSHNLMKGGSTKNWSGNSEFHFYSI NVGGFFKLRAGEEISIQVSNPSLLDPDQDATYFGAFKVQ DID SSGRENLYFQ | Mouse Single Block, RANKL<sup>High</sup> peptide sequence with solubility mutations (C220S/I246E) (mature; no signal peptide and no Hisx6 tag) Set 1 mutations in Table 4. Linker length predicted to restrict folding to Left-hand only. |
| 9 | QPFAHLTINRASIPSGSHKVTLSSWYHDRAWAKISNMT LSNGKLRVNQDGFYYLYANISFRHHETSGSVPTDYLQL MVYVVKTSEKRSSHNLMKGGSTKNWSGNSEFHFYSI NVGGFFKLRAGEEISIQVSNPSLLDPDQDATYFGAFKVQ DID GGSGGGSGGGSG QPFAHLTINAASIPSGSHKVTLSSWYHDRGWAKISNMT LSNGKLRVNQDGFYYLYANISFRHNETSGSVPTDYLQL MVYVVKTSEKRPSSHNLMKGGSTKNWSGNSEFHFYSI NVGGFFKLRAGEEISIQVSNPSLLDPDQDATYFGAFKVQ DID SSGRENLYFQ | Mouse Double Block, RANKL<sup>High</sup> peptide sequence with solubility mutations (C220S/I246E) (mature; no signal peptide and no Hisx6 tag) Set 1 mutations in Table 4. Linker length predicted to restrict folding to Left-hand only. |
| 10 | QPFAHLTINAASIPSGSHKVTLSSWYHDRGWAKISNMT LSNGKLRVNQDGFYYLYANISFRGGSHHETSGSVPTDY LHLMVYVVKTSEKIPSSHNLMKGGSTKNWSGNSEFHF YSINVGGFFKLRAGEEISIQVSNPSLLDPDQDATYFGAF KVQDID GGSGGGSGGGSG QPFAHLTINAASIPSGSHKVTLSSWYHDRGWAEISNMT LSNGKLRVNQDGFYYLYANISFRHHETSGSVPTDYLHL MVYVVKTSEKIPSSHNLMKGGSTKNWSGNSEYYFYSI NVGGFFKLRAGEEISIQVSNPSLLDPDQDATYFGAFKVQ DID GGSGGGSGGGSG QPFAHLTINAASIPSGSHKVTLSSWYHDRGWAEISNMT | Mouse Single Block, RANKL<sup>High</sup> peptide sequence with solubility mutations (C220S/I246E) (mature; no signal peptide and no Hisx6 tag) Set 2 mutations in Table 4. |

TABLE 5-continued

Biological sequences

| SEQ ID NO: | Sequence | Comments |
|---|---|---|
| | LSNGKLRVNQDGFYYLYANISFRHHETSGSVPTDYLHL MVYVVKTSEKIPSSHNLMKGGSTKNWSGNSEYYFYSI NVGGFFKLRAGEEISIQVSNPSLLDPDQDATYFGAFKVQ DID SSGRENLYFQ | |
| 11 | QPFAHLTINAASIPSGSHKVTLSSWYHDRGWAKISNMT LSNGKLRVNQDGFYYLYANISFRGGSHHETSGSVPTDY LHLMVYVVKTSEKIPSSHNLMKGGSTKNWSGNSEFHF YSINVGGFFKLRAGEEISIQVSNPSLLDPDQDATYFGAF KVQDID GGSGGGSGGGSG QPFAHLTINAASIPSGSHKVTLSSWYHDRGWAKISNMT LSNGKLRVNQDGFYYLYANISFRGGSHHETSGSVPTDY LHLMVYVVKTSEKIPSSHNLMKGGSTKNWSGNSEFHF YSINVGGFFKLRAGEEISIQVSNPSLLDPDQDATYFGAF KVQDID GGSGGGSGGGSG QPFAHLTINAASIPSGSHKVTLSSWYHDRGWAEISNMT LSNGKLRVNQDGFYYLYANISFRHHETSGSVPTDYLHL MVYVVKTSEKIPSSHNLMKGGSTKNWSGNSEYYFYSI NVGGFFKLRAGEEISIQVSNPSLLDPDQDATYFGAFKVQ DID SSGRENLYFQ | Mouse Double Block, RANKL$^{High}$ peptide sequence with solubility mutations (C220S/I246E) (mature; no signal peptide and no Hisx6 tag) Set 2 mutations in Table 4. |
| 12 | AQPFAHLTINATDIPSGSHKVSLSSWYHDRGWAKISNM TFSNGKLIVNQDGFYYLYANISFRHHETSGDLATEYLQ LMVYVTKTSEKIPSSHTLMKGGSTKYWSGNSEFHFYSI NVGGFFKLRSGEEISIEVSNPSLLDPDQDATYFGAFKVR DID GGSGGGSGGGSG AQPFAHLTINATDIPSGSHKVSLSSWYHDRGWAKISNM TFSNGKLIVNQDGFYYLYANISFRHHETSGDLATEYLQ LMVYVTKTSEKIPSSHTLMKGGSTKYWSGNSEFHFYSI NVGGFFKLRSGEEISIEVSNPSLLDPDQDATYFGAFKVR DID GGSGGGSGGGSG AQPFAHLTINATDIPSGSHKVSLSSWYHDRGWAKISNM TFSNGKLIVNQDGFYYLYANISFRHHETSGDLATEYLQ LMVYVTKTSEKIPSSHTLMKGGSTKYWSGNSEFHFYSI NVGGFFKLRSGEEISIEVSNPSLLDPDQDATYFGAFKVR DID | Human WT Single Chain RANKL peptide sequence with solubility mutations (C221S/I247E) (mature; no signal peptide) |
| 13 | AQPFAHLTINATDIPSGSHKVSLSSWYHDRGWAKISNM TFSNGKLIVNQDGFYYLYANISFRHNETSGDLATEYLQ LMVYVTKTSEKIPSSHTLMKGGSTKYWSGNSEFHFYSI NVGGFFKLRSGEEISIEVSNPSLLDPDQDATYFGAFKVR DID GGSGGGSGGGSG AQPFAHLTINRTDIPSGSHKVSLSSWYHDRAWAKISNM TFSNGKLIVNQDGFYYLYANISFRHHETSGDLATEYLQ LMVYVTKTSEKIPSSHTLMKGGSTKYWSGNSEFHFYSI NVGGFFKLRSGEEISIEVSNPSLLDPDQDATYFGAFKVR DID GGSGGGSGGGSG AQPFAHLTINRTDIPSGSHKVSLSSWYHDRAWAKISNM TFSNGKLIVNQDGFYYLYANISFRHHETSGDLATEYLQ LMVYVTKTSEKRPSSHTLMKGGSTKYWSGNSEFHFYSI NVGGFFKLRSGEEISIEVSNPSLLDPDQDATYFGAFKVR DID | Human Single Block, RANKL$^{High}$ peptide sequence with solubility mutations (C221S/I247E) (mature; no signal peptide) Set 6 mutations in Table 4. Linker length predicted to restrict folding to Left-hand only. |
| 14 | AQPFAHLTINATDIPSGSHKVSLSSWYHDRGWAKISNM TFSNGKLIVNQDGFYYLYANISFRHNETSGDLATEYLQ LMVYVTKTSEKRPSSHTLMKGGSTKYWSGNSEFHFYSI NVGGFFKLRSGEEISIEVSNPSLLDPDQDATYFGAFKVR DID GGSGGGSGGGSG AQPFAHLTINRTDIPSGSHKVSLSSWYHDRGWAKISNM TFSNGKLIVNQDGFYYLYANISFRHNETSGDLATEYLQ LMVYVTKTSEKIPSSHTLMKGGSTKYWSGNSEFHFYSI NVGGFFKLRSGEEISIEVSNPSLLDPDQDATYFGAFKVR DID GGSGGGSGGGSG AQPFAHLTINRTDIPSGSHKVSLSSWYHDRAWAKISNM | Human Double Block, RANKL$^{High}$ peptide sequence with solubility mutations (C221S/I247E) (mature; no signal peptide) Set 6 mutations in Table 4. Linker length predicted to restrict folding to Left-hand only. |

TABLE 5-continued

Biological sequences

| SEQ ID NO: | Sequence | Comments |
|---|---|---|
| | TFSNGKLIVNQDGFYYLYANISFRHHETSGDLATEYLQ LMVYVTKTSEKRPSSHTLMKGGSTKYWSGNSEFHFYSI NVGGFFKLRSGEEISIEVSNPSLLDPD QDATYFGAFKVRDID | |
| 15 | AQPFAHLTINATDIPSGSHKVSLSSWYHDRGWAKISNM TFSNGKLIVNQDGFYYLYANISFRGGSHHETSGDLATE YLHLMVYVTKTSEKIPSSHTLMKGGSTKYWSGNSEFH FYSINVGGFFKLRSGEEISIEVSNPSLLDPDQDATYFGAF KVRDID GGSGGGSGGGSG AQPFAHLTINATDIPSGSHKVSLSSWYHDRGWAEISNM TFSNGKLIVNQDGFYYLYANISFRHHETSGDLATEYLH LMVYVTKTSEKIPSSHTLMKGGSTKYWSGNSEYYFYSI NVGGFFKLRSGEEISIEVSNPSLLDPDQDATYFGAFKVR DID GGSGGGSGGGSG AQPFAHLTINATDIPSGSHKVSLSSWYHDRGWAEISNM TFSNGKLIVNQDGFYYLYANISFRHHETSGDLATEYLQ LMVYVTKTSEKIPSSHTLMKGGSTKYWSGNSEYYFYSI NVGGFFKLRSGEEISIEVSNPSLLDP | Human Single Block, RANKL$^{High}$ peptide sequence with solubility mutations (C221S/I247E) (mature; no signal peptide) Set 7 mutations in Table 4. |
| 16 | AQPFAHLTINATDIPSGSHKVSLSSWYHDRGWAKISNM TFSNGKLIVNQDGFYYLYANISFRGGSHHETSGDLATE YLHLMVYVTKTSEKIPSSHTLMKGGSTKYWSGNSEFH FYSINVGGFFKLRSGEEISIEVSNPSLLDPDQDATYFGAF KVRDID GGSGGGSGGGSG AQPFAHLTINATDIPSGSHKVSLSSWYHDRGWAKISNM TFSNGKLIVNQDGFYYLYANISFRGGSHHETSGDLATE YLHLMVYVTKTSEKIPSSHTLMKGGSTKYWSGNSEFH FYSINVGGFFKLRSGEEISIEVSNPSLLDPDQDATYFGAF KVRDID GGSGGGSGGGSG AQPFAHLTINATDIPSGSHKVSLSSWYHDRGWAEISNM TFSNGKLIVNQDGFYYLYANISFRHHETSGDLATEYLH LMVYVTKTSEKIPSSHTLMKGGSTKYWSGNSEYYFYSI NVGGFFKLRSGEEISIEVSNPSLLDPDQDATYFGAFKVR DID | Human Double Block, RANKL$^{High}$ peptide sequence with solubility mutations (C221S/I247E) (mature; no signal peptide) Set 7 mutations in Table 4. |
| 17 | SDKPVAHVVANPQAEGQLQWLNRRANALLANGVELR DNQLVVPSEGLYLIYSQVLFKGQGCPSTHVLLTHTISRI AVSYQTKVNLLSAIKSPCQRETPEGAEAKPWYEPIYLG GVFQLEKGDRLSAEINRPDYLDFAESGQVYFGIIAL GGSGGGSGGGSG SDKPVAHVVANPQAEGQLQWLNRRANALLANGVELR DNQLVVPSEGLYLIYSQVLFKGQGCPSTHVLLTHTISRI AVSYQTKVNLLSAIKSPCQRETPEGAEAKPWYEPIYLG GVFQLEKGDRLSAEINRPDYLDFAESGQVYFGIIAL GGSGGGSGGGSG SDKPVAHVVANPQAEGQLQWLNRRANALLANGVELR DNQLVVPSEGLYLIYSQVLFKGQGCPSTHVLLTHTISRI AVSYQTKVNLLSAIKSPCQRETPEGAEAKPWYEPIYLG GVFQLEKGDRLSAEINRPDYLDFAESGQVYFGIIAL | Human WT Single Chain TNF peptide sequence (mature; no signal peptide). |
| 18 | SDKPVAHVVANPQAEGQLQWLNRRANALLANGVELR DNQLVVPSEGLYLIYSQVLFKGQGCPSTHVLLTHTISRI AVSQQTKVNLLSAIKSPCQRETPEGAEAKPWYEPIYLG GVFQLEKGDRLSAEINRPDYLDFAESGQVYFGIIAL GGSGGGSGGGSG SDKPVAHVVANPQAEGQLQWLNRRANALLANGVELR DNQLVVPSEGLYLIYSQVLFKGQGCPSTHVLLTHTISRI AVTYQTKVNLLSAIKSPCQRETPEGAEAKPWYEPIYLG GVFQLEKGDRLSAEINRPDYLDFAESGQVYFGIIAL GGSGGGSGGGSG SDKPVAHVVANPQAEGQLQWLNRRANALLANGVELR DNQLVVPSEGLYLIYSQVLFKGQGCPSTHVLLTHTISRI AVTYQTKVNLLSAIKSPCQRETPEGAEAKPWYEPIYLG GVFQLEKGDRLSAEINRPDYLDFAESGQVYFGIIAL | Human Single Block, TNF$^{High}$ peptide sequence (mature; no signal peptide) Set 16 mutations in Table 4. |
| 19 | SDKPVAHVVANPQAEGQLQWLNRRANALLANGVELR DNQLVVPSEGLYLIYSQVLFKGQGCPSTHVLLTHTISRI AVSQQTKVNLLSAIKSPCQRETPEGAEAKPWYEPIYLG GVFQLEKGDRLSAEINRPDYLDFAESGQVYFGIIAL | Human Double Block, TNF$^{High}$ peptide sequence (mature; no signal peptide) Set 16 mutations in Table 4. |

TABLE 5-continued

Biological sequences

| SEQ ID NO: | Sequence | Comments |
|---|---|---|
|  | GGSGGGSGGGSG<br>SDKPVAHVVANPQAEGQLQWLNRRANALLANGVELR<br>DNQLVVPSEGLYLIYSQVLFKGQGCPSTHVLLTHTISRI<br>AVSQQTKVNLLSAIKSPCQRETPEGAEAKPWYEPIYLG<br>GVFQLEKGDRLSAEINRPDYLDFAESGQVYFGIIAL<br>GGSGGGSGGGSG<br>SDKPVAHVVANPQAEGQLQWTNRFANALLANGVELR<br>DNQLVVPSEGLYLIYSQVLFKGQGCPSTHVLLTHTISRI<br>AVTYQTKVNLLSAIKSPCQRETPEGAEAKPWYEPIYLG<br>GVFQLEKGDRLSAEINRPDYLDFAESGQVYFGIIAL |  |
| 20 | SDKPVAHVVANPQAEGQLQWLNRRANALLANGVELR<br>DNQLVVPSEGLYLIYSQVLFKGQGCPSTHVLLTHTISRI<br>AVSYQTKVNLLSAIKSPCQRETPEGAEAKPWYEPIYLG<br>GVFQLEKGDRLSAEINRPDYLVFAESGQVYFGIIAL<br>GGSGGGSGGGSG<br>SDKPVAHVVANPQAEGQLQWTNRFANALLANGVELR<br>DNQLVVPSEGLYLIYSQVLFKGQGCPSTHVLLTHTISRI<br>AVSYQTKVNLLSAIKSPCQRETPEGAEAKPWYEPIYLG<br>GVFQLEKGDRLSAEINRPDYLDFAESGQVYFGIIAL<br>GGSGGGSGGGSG<br>SDKPVAHVVANPQAEGQLQWTNRFANALLANGVELR<br>DNQLVVPSEGLYLIYSQVLFKGQGCPSTHVLLTHTISRI<br>AVSYQTKVNLLSAIKSPCQRETPEGAEAKPWYEPIYLG<br>GVFQLEKGDRLSAEINRPDYLDFAESGQVYFGIIAL | Human Single Block, TNF$^{High}$ peptide sequence (mature; no signal peptide) Set 17 mutations in Table 4. |
| 21 | SDKPVAHVVANPQAEGQLQWLNRRANALLANGVELR<br>DNQLVVPSEGLYLIYSQVLFKGQGCPSTHVLLTHTISRI<br>AVSYQTKVNLLSAIKSPCQRETPEGAEAKPWYEPIYLG<br>GVFQLEKGDRLSAEINRPDYLVFAESGQVYFGIIAL<br>GGSGGGSGGGSG<br>SDKPVAHVVANPQAEGQLQWLNRRANALLANGVELR<br>DNQLVVPSEGLYLIYSQVLFKGQGCPSTHVLLTHTISRI<br>AVSYQTKVNLLSAIKSPCQRETPEGAEAKPWYEPIYLG<br>GVFQLEKGDRLSAEINRPDYLVFAESGQVYFGIIAL<br>GGSGGGSGGGSG<br>DKPVAHVVANPQAEGQLQWTNRFANALLANGVELRD<br>NQLVVPSEGLYLIYSQVLFKGQGCPSTHVLLTHTISRIA<br>VSYQTKVNLLSAIKSPCQRETPEGAEAKPWYEPIYLGG<br>VFQLEKGDRLSAEINRPDYLDFAESGQVYFGIIAL | Human Double Block, TNF$^{High}$ peptide sequence (mature; no signal peptide) Set 17 mutations in Table 4. |
| 22 | PQRVAAHITGTRGRSNTLSSPNSKNEKALGRKINSWESS<br>RSGHSFLSNLHLRNGELVIHEKGFYYIYSQTYFRFQEEI<br>KENTKNDKQMVQYIYKYTSYPDPILLMKSARNSCWSK<br>DAEYGLYSIYQGGIFELKENDRIFVSVTNEHLIDMDHEA<br>SFFGAFLVG<br>GGSGGGSGGGSG<br>PQRVAAHITGTRGRSNTLSSPNSKNEKALGRKINSWESS<br>RSGHSFLSNLHLRNGELVIHEKGFYYIYSQTYFRFQEEI<br>KENTKNDKQMVQYIYKYTSYPDPILLMKSARNSCWSK<br>DAEYGLYSIYQGGIFELKENDRIFVSVTNEHLIDMDHEA<br>SFFGAFLVG<br>GGSGGGSGGGSG<br>PQRVAAHITGTRGRSNTLSSPNSKNEKALGRKINSWESS<br>RSGHSFLSNLHLRNGELVIHEKGFYYIYSQTYFRFQEEI<br>KENTKNDKQMVQYIYKYTSYPDPILLMKSARNSCWSK<br>DAEYGLYSIYQGGIFELKENDRIFVSVTNEHLIDMDHEA<br>SFFGAFLVG | Human WT Single Chain TRAIL peptide sequence (mature; no signal peptide). |
| 23 | PQRVAAHITGTRGRSNTLSSPNSKNEKALGRKINSWESS<br>RSGHSFLSNLHLRNGELVIHEKGFYYIYSQTAFRFSEEIK<br>ENTKNDKQMVQYIYKYTSYPDPILLMKSARNSCWSKD<br>AEYGLYSIYQGGIFELKENDRIFVSVTNEHLIDMDHEAS<br>FFGAFLVG<br>GGSGGGSGGGSG<br>PQRVAAHITGTRGRSNTLSSPNSKNEKALGRKINSWESS<br>RSGHSFLSNLHLRNGELVIHEKGFYYIYSQTYFRFQEEI<br>KENTKNDKQMVQYIYKYTSYPDPILLMKSARNSCWSK<br>DAEYGLYSIYQGGIFELKENDRIFVSVTNEHLIDMHHEA<br>SFFGAFLVG<br>GGSGGGSGGGSG<br>PQRVAAHITGTRGRSNTLSSPNSKNEKALGRKINSWESS<br>RSGHSFLSNLHLRNGELVIHEKGFYYIYSQTYFRFQEEI<br>KEVTRNDKQMVQYIYKWTDYPDPILLMKSARNSCWS | Human Single Block, TRAIL$^{High}$ peptide sequence (mature; no signal peptide) Set 23 mutations in Table 4. Linker length predicted to restrict folding to Left-hand only. |

TABLE 5-continued

Biological sequences

| SEQ ID NO: | Sequence | Comments |
|---|---|---|
| | KDAEYGLYSIYQGGIFELKENDRIFVSVTNEHLIDMHHE ASFFGAFLVG | |
| 24 | PQRVAAHITGTRGRSNTLSSPNSKNEKALGRKINSWESS RSGHSFLSNLHLRNGELVIHEKGFYYIYSQTAFRFSEEIK ENTKNDKQMVQYIYKYTSYPDPILLMKSARNSCWSKD AEYGLYSIYQGGIFELKENDRIFVSVTNEHLIDMDHEAS FFGAFLVG GGSGGGSGGGSG PQRVAAHITGTRGRSNTLSSPNSKNEKALGRKINSWESS RSGHSFLSNLHLRNGELVIHEKGFYYIYSQTYFRFQEEI KEVTRNDKQMVQYIYKWTDYPDPILLMKSARNSCWS KDAEYGLYSIYQGGIFELKENDRIFVSVTNEHLIDMHHE ASFFGAFLVG GGSGGGSGGGSG PQRVAAHITGTRGRSNTLSSPNSKNEKALGRKINSWESS RSGHSFLSNLHLRNGELVIHEKGFYYIYSQTAFRFSEEIK EVTRNDKQMVQYIYKWTDYPDPILLMKSARNSCWSK DAEYGLYSIYQGGIFELKENDRIFVSVTNEHLIDMDHEA SFFGAFLVG | Human Double Block, TRAIL$^{High}$ peptide sequence (mature; no signal peptide) Set 23 mutations in Table 4. Linker length predicted to restrict folding to Left-hand only. |
| 25 | MGILPSPGMPALLSLVSLLSVLLMGCVA | signal peptide from pHLsec |
| 26 | SSGRENLYFQGHHHHHH | tobacco etch virus (TEV) protease cleavage site and a 6x-histidine tag |
| 27 | SSGRENLYFQ | TEV cleavage product of SEQ ID NO: 27 |
| 28 | ATGTGGGTGTTCAAGTTTCTGC | Cathepsin K primer (forward) |
| 29 | CCACAAGATTCTGGGGACTC | Cathepsin K primer (reverse) |
| 30 | CCCGTCACATTCTGGTCCAT | NFATc1 primer (forward) |
| 31 | CAAGTAACCGTGTAGCTGCACAA | NFATc1 primer (reverse) |
| 32 | CAGCTCCCTAGAAGATGGATTCAT | TRAP primer (forward) |
| 33 | GTCAGGAGTGGGAGCCATATG | TRAP primer (reverse) |
| 34 | TTCGACTACGGCCAGATGATT | β3 primer (forward) |
| 35 | GGAGAAAGACAGGTCCATCAAGT | β3 primer (reverse) |
| 36 | AGCATACAGGTCCTGGCATC | Cyclophilin primer (forward) |
| 37 | TTCACCTTCCCAAAGACCAC | Cyclophilin primer (reverse) |
| 38 | GGSG | Peptide linker |
| 39 | GGGS | Peptide linker |
| 40 | GGGGS | Peptide linker |
| 41 | GSAT | Peptide linker |
| 42 | PQRVAAHITGTRGRSNTLSSPNSKNEKALGRKINSWESS RSGHSFLSNLHLRNGELVIHEKGFYYIYSQTNFKFREEI KERTHNDKQMVQYIYKYTDYPDPILLMKSARNSCWSK DAEYGLYSIYQGGIFELKENDRIFVSVTNERLLQMDHE ASFFGAFLVG GGSGGGSGGGSG PQRVAAHITGTRRRSNTLSSPNSKNEKALGRKINSWESS RRGHSFLSNLHLRNGELVIHEKGFYYIYSQTYFRFQEEI KERTHNDKQMVQYIYKYTDYPDPILLMKSARNSCWSK DAEYGLYSIYQGGIFELKENDRIFVSVTNEHLIDMDHEA SFFGAFLVG GGSGGGSGGGSG PQRVAAHITGTRRRSNTLSSPNSKNEKALGRKINSWESS RRGHSFLSNLHLRNGELVIHEKGFYYIYSQTYFRFQEEI | Human Single Block, TRAIL$^{High}$ peptide sequence (mature; no signal peptide) Set 24 mutations in Table 4. Linker length predicted to restrict folding to Left-hand only. |

TABLE 5-continued

Biological sequences

| SEQ ID NO: | Sequence | Comments |
|---|---|---|
| | KENTKNDKQMVQYIYKYTSYPDPILLMKSARNSCWSK<br>DAEYGLYSIYQGGIFELKENDRIFVSVTNEHLIDMDHEA<br>SFFGAFLVG | |
| 43 | QRVAAHITGTRGRSNTLSSPNSKNEKALGRKINSWESS<br>RSGHSFLSNLHLRNGELVIHEKGFYYIYSQTNFKFREEI<br>KERTHNDKQMVQYIYKYTDYPDPILLMKSARNSCWSK<br>DAEYGLYSIYQGGIFELKENDRIFVSVTNERLLQMDHE<br>ASFFGAFLVG<br>GGSGGGSGGGSG<br>QRVAAHITGTRRRSNTLSSPNSKNEKALGRKINSWESS<br>RRGHSFLSNLHLRNGELVIHEKGFYYIYSQTYFRFQEEI<br>KENTKNDKQMVQYIYKYTSYPDPILLMKSARNSCWSK<br>DAEYGLYSIYQGGIFELKENDRIFVSVTNEHLIDMDHEA<br>SFFGAFLVG<br>GGSGGGSGGGSG<br>QRVAAHITGTRGRSNTLSSPNSKNEKALGRKINSWESS<br>RSGHSFLSNLHLRNGELVIHEKGFYYIYSQTNFKFREEI<br>KENTKNDKQMVQYIYKYTSYPDPILLMKSARNSCWSK<br>DAEYGLYSIYQGGIFELKENDRIFVSVTERLLQMDHEA<br>SFFGAFLVG | Human Double Block,<br>TRAIL$^{High}$ peptide sequence (mature; no signal peptide)<br>Set 24 mutations in Table 4.<br>Linker length predicted to restrict folding to Left-hand only. |
| 44 | FRGGSHHET | Sequence generated by an insertion of GGS after R222 in strand C of RANKL |

In certain scTNFsfL presented in Table 5, the monomers and peptide linkers are shown on separate lines. In certain instances, portions of a TEV cleavage site are shown on a separate line. Mutations in certain TNFsf monomers are shown in boldface and are underlined.

REFERENCES

1. Croft, M., W. Duan, H. Choi, S.-Y. Eun, S. Madireddi, and A. Mehta. 2012. TNF superfamily in inflammatory disease: translating basic insights. *Trends Immunol.* 33: 144-152.
2. Vinay, D. S., and B. S. Kwon. 2011. The tumour necrosis factor/TNF receptor superfamily: therapeutic targets in autoimmune diseases. *Clin. Exp. Immunol.* 164: 145-157.
3. Tansey, M. G., and D. E. Szymkowski. 2009. The TNF superfamily in 2009: new pathways, new indications, and new drugs. *Drug Discov. Today* 14: 1082-1088.
4. Kong, Y. Y., H. Yoshida, I. Sarosi, H. L. Tan, E. Timms, C. Capparelli, S. Morony, A. J. Oliveira-dos-Santos, G. Van, A. Itie, W. Khoo, A. Wakeham, C. R. Dunstan, D. L. Lacey, T. W. Mak, W. J. Boyle, and J. M. Penninger. 1999. OPGL is a key regulator of osteoclastogenesis, lymphocyte development and lymph-node organogenesis. *Nature* 397: 315-323.
5. Kim, N., P. R. Odgren, D. K. Kim, S. C. Marks, and Y. Choi. 2000. Diverse roles of the tumor necrosis factor family member TRANCE in skel et al physiology revealed by TRANCE deficiency and partial rescue by a lymphocyte-expressed TRANCE transgene. *Proc Natl Acad Sci USA* 97: 10905-10910.
6. Burgess, T. L., Y. Qian, S. Kaufman, B. D. Ring, G. Van, C. Capparelli, M. Kelley, H. Hsu, W. J. Boyle, C. R. Dunstan, S. Hu, and D. L. Lacey. 1999. The ligand for osteoprotegerin (OPGL) directly activates mature osteoclasts. *J. Cell Biol.* 145: 527-538.
7. Lacey, D. L., E. Timms, H. L. Tan, M. J. Kelley, C. R. Dunstan, T. Burgess, R. Elliott, A. Colombero, G. Elliott, S. Scully, H. Hsu, J. Sullivan, N. Hawkins, E. Davy, C. Capparelli, A. Eli, Y. X. Qian, S. Kaufman, I. Sarosi, V. Shalhoub, G. Senaldi, J. Guo, J. Delaney, and W. J. Boyle. 1998. Osteoprotegerin ligand is a cytokine that regulates osteoclast differentiation and activation. *Cell* 93: 165-176.
8. Lam, J., C. A. Nelson, F. P. Ross, S. L. Teitelbaum, and D. H. Fremont. 2001. Crystal structure of the TRANCE/RANKL cytokine reveals determinants of receptor-ligand specificity. *J. Clin. Invest.* 108: 971-979.
9. Nelson, C. A., J. T. Warren, M. W.-H. Wang, S. L. Teitelbaum, and D. H. Fremont. 2012. RANKL employs distinct binding modes to engage RANK and the osteoprotegerin decoy receptor. *Structure/Folding and Design* 20: 1971-1982.
10. Liu, C., T. S. Walter, P. Huang, S. Zhang, X. Zhu, Y. Wu, L. R. Wedderburn, P. Tang, R. J. Owens, D. I. Stuart, J. Ren, and B. Gao. 2010. Structural and functional insights of RANKL-RANK interaction and signaling. *The Journal of Immunology* 184: 6910-6919.
11. Ta, H. M., G. T. T. Nguyen, H. M. Jin, J. Choi, H. Park, N. Kim, H.-Y. Hwang, and K. K. Kim. 2010. Structure-based development of a receptor activator of nuclear factor-kappaB ligand (RANKL) inhibitor peptide and molecular basis for osteopetrosis. *Proceedings of the National Academy of Sciences* 107: 20281-20286.
12. Lacey, D. L., W. J. Boyle, W. S. Simonet, P. J. Kostenuik, W. C. Dougall, J. K. Sullivan, J. San Martin, and R. Dansey. 2012. Bench to bedside: elucidation of the OPG-RANK-RANKL pathway and the development of denosumab. *Nat Rev Drug Discov* 11: 401-419.
13. Krippner-Heidenreich, A., I. Grunwald, G. Zimmermann, M. Kuihnle, J. Gerspach, T. Sterns, S. D. Shnyder, J. H. Gill, D. N. Männel, K. Pfizenmaier, and P. Scheurich. 2008. Single-chain TNF, a TNF derivative with enhanced stability and antitumoral activity. *J. Immunol.* 180: 8176-8183.
14. Boschert, V., A. Krippner-Heidenreich, M. Branschadel, J. Tepperink, A. Aird, and P. Scheurich. 2010. Single chain TNF derivatives with individually mutated receptor binding sites reveal differential stoichiometry of ligand receptor complex formation for TNFR1 and TNFR2. *Cell. Signal.* 22: 1088-1096.

15. Schneider, B., S. Munkel, A. Krippner-Heidenreich, I. Grunwald, W. S. Wels, H. Wajant, K. Pfizenmaier, and J. Gerspach. 2010. Potent antitumoral activity of TRAIL through generation of tumor-targeted single-chain fusion proteins. *Cell Death and Disease* 1: e68.

16. Spitzer, D., J. E. McDunn, S. Plambeck-Suess, P. S. Goedegebuure, R. S. Hotchkiss, and W. G. Hawkins. 2010. A genetically encoded multifunctional TRAIL trimer facilitates cell-specific targeting and tumor cell killing. *Molecular Cancer Therapeutics* 9: 2142-2151.

17. Gai, S. A., and K. D. Wittrup. 2007. Yeast surface display for protein engineering and characterization. *Curr. Opin. Struct. Biol.* 17: 467-473.

18. Yasuda, H., N. Shima, N. Nakagawa, S. I. Mochizuki, K. Yano, N. Fujise, Y. Sato, M. Goto, K. Yamaguchi, M. Kuriyama, T. Kanno, A. Murakami, E. Tsuda, T. Morinaga, and K. Higashio. 1998. Identity of osteoclastogenesis inhibitory factor (OCIF) and osteoprotegerin (OPG): a mechanism by which OPG/OCIF inhibits osteoclastogenesis in vitro. *Endocrinology* 139: 1329-1337.

19. Simonet, W. S., D. L. Lacey, C. R. Dunstan, M. Kelley, M. S. Chang, R. Liithy, H. Q. Nguyen, S. Wooden, L. Bennett, T. Boone, G. Shimamoto, M. DeRose, R. Elliott, A. Colombero, H. L. Tan, G. Trail, J. Sullivan, E. Davy, N. Bucay, L. Renshaw-Gegg, T. M. Hughes, D. Hill, W. Pattison, P. Campbell, S. Sander, G. Van, J. Tarpley, P. Derby, R. Lee, and W. J. Boyle. 1997. Osteoprotegerin: a novel secreted protein involved in the regulation of bone density. *Cell* 89: 309-319.

20. Schneeweis, L. A., D. Willard, and M. E. Milla. 2005. Functional dissection of osteoprotegerin and its interaction with receptor activator of NF-kappaB ligand. *J. Biol. Chem.* 280: 41155-41164.

21. Hehlgans, T., and K. Pfeffer. 2005. The intriguing biology of the tumour necrosis factor/tumour necrosis factor receptor superfamily: players, rules and the games. *Immunology* 115: 1-20.

22. Peschon, J. J., D. S. Torrance, K. L. Stocking, M. B. Glaccum, C. Otten, C. R. Willis, K. Charrier, P. J. Morrissey, C. B. Ware, and K. M. Mohler. 1998. TNF receptor-deficient mice reveal divergent roles for p55 and p75 in several models of inflammation. *J. Immunol.* 160: 943-952.

23. Mewar, D., and A. G. Wilson. 2011. Treatment of rheumatoid arthritis with tumour necrosis factor inhibitors. *Br. J. Pharmacol.* 162: 785-791.

24. Van Hauwermeiren, F., R. E. Vandenbroucke, and C. Libert. 2011. Treatment of TNF mediated diseases by selective inhibition of soluble TNF or TNFR1. *Cytokine Growth Factor Rev.* 22: 311-319.

25. Keystone, E. C. 2011. Does anti-tumor necrosis factor-α therapy affect risk of serious infection and cancer in patients with rheumatoid arthritis?: a review of longterm data. *J. Rheumatol.* 38: 1552-1562.

26. Bongartz, T., A. J. Sutton, M. J. Sweeting, I. Buchan, E. L. Matteson, and V. Montori. 2006. Anti-TNF antibody therapy in rheumatoid arthritis and the risk of serious infections and malignancies: systematic review and meta-analysis of rare harmful effects in randomized controlled trials. *JAMA* 295: 2275-2285.

27. Bluml, S., C. Scheinecker, J. S. Smolen, and K. Redlich. 2012. Targeting TNF receptors in rheumatoid arthritis. *International Immunology* 24: 275-281.

28. Kollias, G., and D. Kontoyiannis. 2002. Role of TNF/TNFR in autoimmunity: specific TNF receptor blockade may be advantageous to anti-TNF treatments. *Cytokine Growth Factor Rev.* 13: 315-321.

29. Hymowitz, S. G., and A. M. de Vos PhD. 2005. Structures of TNF Receptors and Their Interactions With Ligands. In *Death Receptors in Cancer Therapy* W. El-Deiry, ed. Humana Press. 65-81.

30. Mukai, Y., T. Nakamura, M. Yoshikawa, Y. Yoshioka, S.-I. Tsunoda, S. Nakagawa, Y. Yamagata, and Y. Tsutsumi. 2010. Solution of the structure of the TNF-TNFR2 complex. *Sci Signal* 3: ra83.

31. Steed, P. M., M. G. Tansey, J. Zalevsky, E. A. Zhukovsky, J. R. Desjarlais, D. E. Szymkowski, C. Abbott, D. Carmichael, C. Chan, L. Cherry, P. Cheung, A. J. Chirino, H. H. Chung, S. K. Doberstein, A. Eivazi, A. V. Filikov, S. X. Gao, R. S. Hubert, M. Hwang, L. Hyun, S. Kashi, A. Kim, E. Kim, J. Kung, S. P. Martinez, U. S. Muchhal, D.-H. T. Nguyen, C. O'Brien, D. O'Keefe, K. Singer, O. Vafa, J. Vielmetter, S. C. Yoder, and B. I. Dahiyat. 2003. Inactivation of TNF signaling by rationally designed dominant-negative TNF variants. *Science* 301: 1895-1898.

32. Mancia, F., S. D. Patel, M. W. Rajala, P. E. Scherer, A. Nemes, I. Schieren, W. A. Hendrickson, and L. Shapiro. 2004. Optimization of protein production in mammalian cells with a coexpressed fluorescent marker. *Structure/Folding and Design* 12: 1355-1360.

33. Aricescu, A. R., W. Lu, and E. Y. Jones. 2006. A time- and cost-efficient system for high-level protein production in mammalian cells. *Acta Crystallogr. D Biol. Crystallogr.* 62: 1243-1250.

34. Izawa, T., W. Zou, J. C. Chappel, J. W. Ashley, X. Feng, and S. L. Teitelbaum. 2012. c-Src links a RANK/αvβ3 integrin complex to the osteoclast cytoskeleton. *Mol. Cell. Biol.* 32: 2943-2953.

35. Takeshita, S., K. Kaji, and A. Kudo. 2000. Identification and characterization of the new osteoclast progenitor with macrophage phenotypes being able to differentiate into mature osteoclasts. *J Bone Miner Res* 15: 1477-1488.

36. Gietz, R. D., and R. H. Schiestl. 2007. Large-scale high-efficiency yeast transformation using the LiAc/SS carrier DNA/PEG method. *Nat Protoc* 2: 38-41.

37. DeSelm, C. J., Y. Takahata, J. Warren, J. C. Chappel, T. Khan, X. Li, C. Liu, Y. Choi, Y. F. Kim, W. Zou, and S. L. Teitelbaum. 2012. IL-17 mediates estrogen-deficient osteoporosis in an Actl-dependent manner. *J. Cell. Biochem.* 113: 2895-2902.

38. Tomimori, Y., K. Mori, M. Koide, Y. Nakamichi, T. Ninomiya, N. Udagawa, and H. Yasuda. 2009. Evaluation of pharmaceuticals with a novel 50-hour animal model of bone loss. *J Bone Miner Res* 24: 1194-1205.

The breadth and scope of the present disclosure should not be limited by any of the above-described embodiments in the Examples, but should be defined only in accordance with the following claims and their equivalents.

The invention claimed is:

1. A recombinant single chain polypeptide comprising:

a first receptor activator of nuclear factor kappa-B ligand (RANKL) monomer comprising at least 85% sequence identity to residues 165 to 314 of SEQ ID NO: 2, a second RANKL monomer comprising at least 85% sequence identity to residues 165 to 314 of SEQ ID NO: 2, and a third RANKL monomer comprising at least 85% sequence identity to residues 165 to 314 of SEQ ID NO: 2;

wherein, the first RANKL monomer, the second RANKL monomer, and the third RANKL monomer are operably linked in the C to N direction with peptide linkers;

the recombinant single chain polypeptide forms a RANKL trimer, the RANKL trimer comprising:

(i) a first receptor binding site comprising a first gain of function variant selected from the group consisting of A172R, K195E, Q237H, Q237T, H271Y, F270Y, and combinations thereof, wherein the first gain of function variant increases binding avidity to receptor activator of nuclear factor kappa-B (RANK);

(ii) a second receptor binding site comprising a second gain of function variant selected from the group consisting of A172R, K195E, Q237H, Q237T, H271Y, F270Y, and combinations thereof, wherein the second gain of function variant increases binding avidity to a RANK; and (iii) a third receptor binding site comprising a loss of function variant, wherein the loss of function variant decreases binding avidity or blocks binding to RANK; and the RANKL trimer has a high avidity to RANK and a low avidity to osteoprotegerin (OPG).

2. The recombinant single chain polypeptide of claim 1, wherein the first, second, or third receptor binding site comprises a solubility mutation selected from the group consisting of I247Q, I247E, I247K, I247R, C221S, and combinations thereof.

3. A recombinant nucleic acid, encoding the recombinant single chain polypeptide of claim 1, wherein the recombinant nucleic acid is operably linked to a promoter or a nucleic acid encoding a signal peptide, wherein the signal peptide provides for secretion of the recombinant single chain polypeptide when expressed in a host cell.

4. An isolated host cell containing the recombinant nucleic acid of claim 3.

5. A composition comprising the recombinant single chain polypeptide of claim 1 and a pharmaceutically acceptable excipient.

* * * * *